US008603014B2

(12) United States Patent
Alleman et al.

(10) Patent No.: US 8,603,014 B2
(45) Date of Patent: *Dec. 10, 2013

(54) HANDS-FREE OPERATOR-INDEPENDENT TRANSCRANIAL ULTRASOUND APPARATUS AND METHODS

(75) Inventors: Anthony John Alleman, Sherwood, OR (US); William Barnard, Maple Valley, WA (US); Randal Lee Radford, Burien, WA (US)

(73) Assignee: Cerevast Therapeutics, Inc., Redmond, WA (US)

( * ) Notice: Subject to any disclaimer, the term of this patent is extended or adjusted under 35 U.S.C. 154(b) by 45 days.

This patent is subject to a terminal disclaimer.

(21) Appl. No.: 13/209,408

(22) Filed: Aug. 14, 2011

(65) Prior Publication Data

US 2012/0083718 A1 Apr. 5, 2012

Related U.S. Application Data

(60) Provisional application No. 61/453,767, filed on Mar. 17, 2011, provisional application No. 61/390,156, filed on Oct. 5, 2010.

(51) Int. Cl.
*A61H 1/00* (2006.01)
(52) U.S. Cl.
USPC .................................................... 601/2
(58) Field of Classification Search
USPC .................................................... 601/2
See application file for complete search history.

(56) References Cited

U.S. PATENT DOCUMENTS 6,132,437 A * 10/2000 Omurtag et al. ............. 606/130
2004/0024309 A1   2/2004 Ferre et al.
2004/0267482 A1 * 12/2004 Robertson et al. ........... 702/118
2005/0085748 A1 *  4/2005 Culp et al. ..................... 601/2
2006/0184070 A1   8/2006 Hansmann et al.

(Continued)

FOREIGN PATENT DOCUMENTS

WO   WO 2007/044469   4/2007

OTHER PUBLICATIONS

International Search Report and Written Opinion in technically-related International Patent Application PCT/US2012/027414; dated May 16, 2012; 13 pages.

(Continued)

*Primary Examiner* — Tse Chen
*Assistant Examiner* — Hien Nguyen
(74) *Attorney, Agent, or Firm* — Yakov Sidorin; Quarles & Brady LLP

(57) ABSTRACT

Disclosed is a "hands-free", autonomously operating, battery-powered apparatus with electronic programmable actuation circuitry for non-invasive ultrasonic treatment of ischemic stroke, microatheromas of the cerebral vasculature, intracranial hypertension, and other cerebrovascular pathologies such as hypoperfusion associated with migraine. The apparatus is provided with registration members to facilitate stereotactic placement of the headset on the skull with respect to target intracranial anatomy. Once fitted in place on the skull and activated, the device does not require clinical intervention during operation; does not need skilled technical adjustment of the waveform patterns; and achieves therapeutic results with power consumption of less than 400 mAmp-hr, thus permitting extended portable operation without external power and eliminating the need for assisted cooling. Using a device of the invention, transcranial ultrasound may be self-administered. The device has application in therapeutic methods, such as methods for treating stroke or migraine, for non-invasively augmenting drug action, and for release or dispersal of endogenous neurovascular mediators.

27 Claims, 37 Drawing Sheets

(56) References Cited

U.S. PATENT DOCUMENTS

| | | | |
|---|---|---|---|
| 2007/0049198 A1* | 3/2007 | Walsh et al. | 455/41.2 |
| 2007/0167765 A1* | 7/2007 | Unger et al. | 600/437 |
| 2010/0160780 A1* | 6/2010 | Swan et al. | 600/439 |
| 2011/0054282 A1* | 3/2011 | Nekoomaram et al. | 600/347 |
| 2011/0112405 A1* | 5/2011 | Barthe et al. | 600/459 |

OTHER PUBLICATIONS

International Preliminary Report on Patentability in technically-related International Patent Application PCT/US2012/027414; dated Mar. 8, 2013; 4 pages.

\* cited by examiner

HEMORRHAGE (PRIOR ART)

|  | tPA Only MRI | Ultrasound Plus tPA MRI |
|---|---|---|
| None | 7 | 1 |
| HT1 | 3 | 6 |
| HT2 | 2 | 2 |
| PH2 |  | 2 |
| HT1+SAH |  | 1 |
| PH2+SAH |  | 1 |
| PH1+HT1+VH |  | 1 |
| Total | 12 | 14 |

VH indicates ventricular hemorrhage. (from Daffershofer, 2005)

FOR HANDS-FREE OPERATION WITH AUTOMATED ACOUSTIC COUPLING SENSOR

CELLULAR MODEL OF COAGULATION CASCADE

After Monroe

SONOTHROMBOLYSIS*

| | | |
|---|---|---|
| r-tPA | 30% REC | 4.8% ICH |
| r-tPA + 2MHz US (Pr=20 - 200 KPa) | 49% REC | 4.8% ICH |

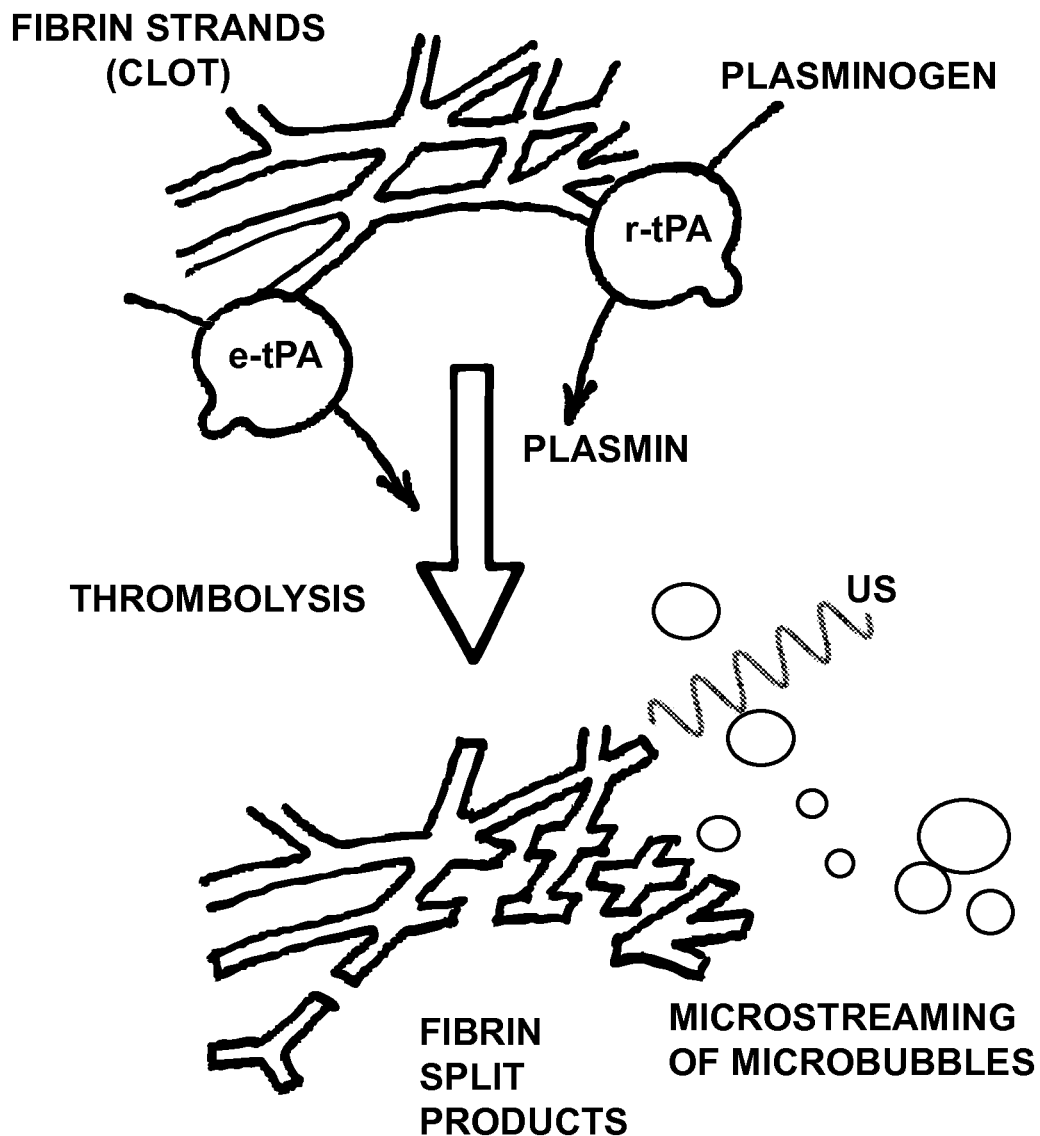

HANDS-FREE OPERATOR-INDEPENDENT TRANSCRANIAL ULTRASOUND APPARATUS AND METHODS

PRIORITY DOCUMENTS

This application claims the benefit of priority under 35 U.S.C. §119(e) from U.S. Provisional Patent Application Ser. No. 61/453,767, filed 17 Mar. 2011, and U.S. Provisional Patent Application Ser. No. 61/390,156, filed 5 Oct. 2010; all said priority documents are incorporated herein in entirety by reference.

FIELD OF THE INVENTION

This invention is related to methods for treating stroke and other neurovascular and vascular conditions and for improving drug activity and delivery using an autonomous, operator-independent, battery-powered ultrasound apparatus with electronic programmable actuation circuitry and stereotactic positioning features for non-invasive transcranial application of ultrasound.

BACKGROUND

Despite the high mortality and morbidity associated with ischemic strokes, which result in loss of blood flow to a part of the brain, current therapies are only partially effective and not effective at all unless given within a very short window following the stroke. After a stroke, brain cells die for lack of oxygen in a spreading penumbra downstream from the clot. Time is of the essence in starting therapy, but many strokes are silent, or go untreated for lack of facilities equipped to properly diagnose stroke and begin therapy. Recombinant tissue plasminogen activator (r-tPA) represents the current treatment paradigm for acute stroke. However, even if r-tPA is given promptly, within a generally recognized critical period of 3 hours following symptom onset, there is no improvement in overall outcomes according to some studies, and there is an increased risk of hemorrhagic conversion (to ICH, "intracranial hemorrhage") and early mortality.

Similarly, administration of heparin or other anticoagulants is generally ineffective in relieving stroke and may be associated with an unacceptably high incidence of ICH. Conservative therapy is just aspirin, but the condition remains the number two cause of death and disability worldwide.

Adjunct therapies have been tested. Surprisingly, ultrasonic imaging machines, including those designed for transcranial Doppler, were found by Alexandrov to potentiate recanalization following administration of r-tPA, and the improvement was associated with a significant decrease in functional impairment at 3 months post-stroke following combined treatment with r-tPA and Doppler ultrasound during a critical period of about 3 hours immediately following onset. However, as reported in U.S. Pat. No. 6,733,450 to Alexandrov, complete recanalization was achieved in only 30% of patients and no improvement was noted in 30% of patients treated with r-tPA and ultrasound in combination. 7.5% of patients developed intracerebral hemorrhage. There is room for further improvement.

Using transcranial color-coded doppler (TCCD) continuous monitoring without the use of r-tPA, Cintas reported a higher rate of partial recanalization in a study (n=6) reported in 2002 (Stroke 33:626-28). A focused 2 MHz transducer was used and the transducer was held in place on a metal frame following diagnostic sonography. A focused beam intensity of 415 mW/cm$^2$ was aimed at a 1 cm length of the MCA containing the occlusion, a treatment that requires a high level of skill and instrumentation to deliver.

Other innovations have been made by Lauer, Alexandrov, Holland, Culp, Unger, Voorhees, Vortman, Chopra, Baron, Furuhata, Horzewski, Hansmann, Smith, Browning, Daffertshoffer, and by others.

However, all studies to date have been problematic in one way or another. The device of the invention differs from the devices used in the earlier CLOTBUST studies (Alexandrov et al 2004a & 2004b) and in studies by Sharma et al (2008a & 2008b) and Cintas (2002) in that those studies used a single diagnostic transducer unit manually operated by a skilled sonographer to establish a preferred orientation, and the transducer unit was then typically locked into place using a cumbersome support frame. Alexandrov recently summarized the art in that, "One of major limitations of this technology that there are no reliable head frames for transducer fixation, and most studies are to be carried out hand-held" (Tsivgoulis 2007 J Clin Neurol 3:1-8). The head frames generally have a skeleton of surgical steel and are weighty and opaque to CT or MRI scanners.

Because the transducer units of the art must be carefully placed by sonographic imaging of the cerebral vasculature, generally with Doppler imaging, valuable time is lost. A solution to this problem as described here is to position a headset of the invention without diagnostic imaging as a guide, but instead using mechanical alignment guides by reference to external craniological landmarks and to use non-focused ultrasound transducers. Craniological landmarks are selected that define a reference plane tangential to the anterior and posterior cingulate processes, the reference plane with x, y and z coordinates, and thus the location of the cerebrovascular nexus where most strokes occur. The need for sonographer-controlled aiming is eliminated by preset angulation of each transducer relative to the external landmarks and the reference plane defined thereby.

Also consequent to the use of trained operators to set up devices for transcranial sonothrombolysis, there is in the art a general lack of consistency from operator to operator and from institution to institution. The reproducibility of transcranial ultrasound would be increased by provision for an apparatus that is configured to autonomously deliver a prescribed regimen of ultrasound with a fixed anatomical orientation. A solution to the problem of reproducibility, which avoids the need for a precise localization of a clot, is to provide transducers on a headset that is positioned as described above, so that the relationship of the transducer arrays to the cerebral vasculature is established by reference to external craniological landmarks, and to then insonate in a way that is generally safe; independent of the results of any diagnostic study.

In a preferred embodiment, the apparatus may be used where hemorrhage is present or is likely to occur, as is not infrequently the case in stroke and particular in stroke that has been treated with anticoagulants or thrombolytic drugs.

In another embodiment of the inventive apparatus, the autonomous insonation regime includes cyclical repetition of trains of pulses of ultrasound, where each cyclical repetition of pulse trains is a "metapulse" having a vectored and temporal distribution of individual pulse trains, with provision for alternating from transducer to transducer and limiting duty cycle so that no assisted cooling is required. The amplitude of ultrasound emitted by each transducer may be adjusted to compensate for differences due to transducer-to-transducer variability in manufacture, a distinct technological advance in the art.

Portability remains a problem. Several features of the apparatus of the invention operate in synergy to enable the device to be transported with the subject without interrupting insonation, so that the subject may be transported or even walk while wearing the apparatus. By providing a lightweight, portable power supply in a pocket-sized housing attached to the headset by a cable, the need for attachment to a stationary power supply is eliminated. Low power consumption for extended use is achieved by reducing the duty cycle of the insonation and by configuring emissions in the form of pulse trains having a pulse repetition frequency (PRF) and a metapulse cycle repetition frequency (MCRF), by using resonant circuit elements, lower driving voltage, and by operating so that assisted cooling is not required. Elimination of energy-consuming cooling means is made possible by alternating actuation of individual transducers so that heat may dissipate in spaces between transducers during pulse intervals by passive conductive and convective mechanisms, eliminating the need for assisted cooling, such as with fans or circulating coolant.

By making the headset from a lightweight and X-ray translucent material, and by configuring ultrasonic emissions from the headset transducer arrays for low power consumption, the apparatus becomes fully portable, may be transported with the patient, and operation of the apparatus need not be interrupted while the subject is, for example, inserted into a diagnostic machine for computerized tomography (CT). The option of beginning and continuing insonation while awaiting definitive diagnosis by angiographic CT is made possible by tethering the electronics and power supply away from the headset assembly at the end of a cable so that diagnostic imaging is not interfered with and by use of plastic structural members. Because transverse sections are commonly used in imaging to visualize the cerebral arterial nexii, in one embodiment the transducer array is mounted supracranially so that imaging may be performed without interference.

The option of portable extended delivery of transcranial ultrasound for sonothrombolysis has been a longstanding need but has not previously been realized. The apparatus of the invention is configured for continuous autonomous operation for 2 hrs, for 4 hours, for up to 12 hours, or for longer with intermittent operation, without operator intervention or recharge, and hence may be used non-invasively in stroke prophylaxis, as a follow-up to administration of thrombolytic drugs, and for other neurovascular conditions where persistent exposure to low amplitude ultrasound is desirable.

Tools for non-invasive sonothrombolysis, as known in the art, remain experimental, and have not yet resulted in changes to the basic standard of care for stroke or dramatically improved the prognosis. Recent clinical trials supplementing r-tPA with transcranial ultrasound resulted in an unacceptably high incidence of intracranial hemolysis (ICH) and the trials were stopped. Since then, no advance in the clinical use of transcranial sonothrombolysis has been reported.

Importantly, centralized stroke centers that specialize in stroke diagnosis and advanced treatment—absent sonothrombolysis—have improved mortality and morbidity following stroke by only 20% overall. Each year in the United States, 700,000 strokes occur and more than 150,000 deaths are caused by strokes. Following a stroke, life expectancy drops to 5 years or less for most victims. When r-tPA is given alone, reperfusion is not achieved in 74% of cases (according to del Zoppo et al, 1992, Ann Neurol 32:78-86). Thus there is a need for new solutions and improvements in therapy. The problems of existing invasive therapies, the risk of administration of r-tPA among them, continue to outweigh potential benefits in the estimation of many physicians, and there is a long-felt and unmet need for a therapy for stroke having improved efficacy; a need for a therapy that is non-invasive and safe; a need for a therapy that does not require trained sonographers to administer and instead relies on craniological landmarks to align a plurality of transducer arrays for insonation of the cerebral vasculature associated with most strokes; a need to begin treatment prior to a definitive diagnosis by CT or MRI; the need for reproducible therapy based on autonomous administration of a cyclical regime insonation at defined frequency, pulse repetition frequency (PRF), pulse train repetition frequency (PTRF), pulse duration, peak rarefaction pressure and beam centerline vector; and the need to begin treatment prior to administration of r-tPA, while not limited thereto.

Serendipitously, we have unexpectedly discovered that the device we have developed for stroke is also suitable more generally for non-invasive therapies in a variety of neurological and vascular conditions such as migraine, intracranial hypertension, hydrocephalus and even the common headache, which are also associated with significant loss of productivity and quality of life, and also may be used with negligible or minimal risk as an adjunct therapy in drug delivery and for release of mediators of physiological function such as endogenous tissue plasminogen activator, nitric oxide, and prostaglandins.

SUMMARY

In a first embodiment, the device is an improved headset assembly for non-invasive transcranial ultrasound independent of operator control or adjustment and eliminating the need for imaging-guided placement or diagnostic study. The headset assembly is attached by a cable to a lightweight portable controller unit and battery power supply, and is configured for operator independent, autonomous operation with low power consumption.

Mounted on the headset assembly are a plurality of ultrasound transducers for acoustically engaging a head of a wearer. The headset is configured to be mounted circumcranially, and is provided with a registration system for stereotactically positioning the transducer arrays in contact with acoustic "windows" through the skull and directing the transducers to emit ultrasound onto the cerebral arteries most commonly associated with stroke. Conserved external craniological landmarks are used to position the headset with respect to the target cerebral vasculature.

The apparatus is also useful for non-surgical application of ultrasound in ischemic stroke and, with modification, for other infarcted or embolic conditions.

Several problems in administering ultrasound transcranially have been identified and are addressed by this invention.

1. As disclosed here, stereotactic positioning using a combination of conserved external craniological landmarks eliminates the need for a trained sonographer and imaging transducer to properly position the headset on a head. A tightening mechanism is provided to ensure acoustic coupling. Optionally, the apparatus determines whether each transducer of the headset is acoustically coupled to the head and alerts the user if repositioning is needed.

2. By combining this self-positioning feature with autonomous administration of an ultrasonic pulse train in a predetermined pattern or patterns that conforms to safe limits as experimentally established, the device can be used prior to obtaining a diagnosis, thus gaining valuable time and reducing morbidity and mortality where stroke is suspected. Autonomous operation is expected to substantially improve consistency and reproducibility of ultrasonic exposure; in contrast investigative efforts to date have relied on manual application by sonographers having varying technique and adapting various makes of diagnostic equipment not intended for therapeutic application.

3. Early studies also demonstrated that appropriate selection of a pulse modulation rate was important in improving user comfort, because users with sensitive hearing may demodulate the pulse frequency and experience an uncomfortable auditory sensation.

4. Unlike previous studies, a sharp increase in ICH conversion is not seen when used as a co-therapy with r-tPA. Limits on frequency, pulse repetition frequency, pulse interval and amplitude are built into the device so that the device is intended to be operated without need for operator adjustment, i.e. literally in a "hands-free" mode, and may be operated "blindly" (i.e., without the need to first make a definitive diagnosis using invasive imaging modalities such as contrast-enhanced CT or MRI). The device thus solves one of the most difficult of the problems that has slowed application of transcranial ultrasound, the inability to begin therapy until a diagnosis is in hand because of otherwise unacceptable risks. The evidence of risks can be readily seen for example by study of the literature (Daffershoffer et al 2005 Stroke 36:1441), where individuals receiving ultrasound in combination with r-tPA experienced unacceptable complications. Since the devices of the invention do not require Doppler imaging capability, there is no need for higher intensity beams to be directed against or with the direction of blood flow in the vessels of the Circle of Willis in order for insonation to be effective.

According to one aspect of the invention, we have shown that pulse emissions driven by a voltage ($V_{p\text{-}p}$) configured to deliver an attenuated peak rarefaction pressure $P_{r,A}$ at depth $z_{sp}$ not to exceed 300 KPa and not to exceed a physiologically compatible thermal index are useful and safe, overcoming a technical hurdle encountered in the prior art.

5. In response to a need to develop a pattern or patterns of modulated ultrasonic waveforms that would be safe and could be built into operation of the device, disclosed here are suitable parameters for a cyclical regimen of ultrasound having defined frequency, pulse repetition frequency (PRF), pulse duration, peak rarefaction pressure; beam centerline vector, and metapulse cycle repetition frequency (MCRF), where each cyclical repetition of pulse trains is a "metapulse" or "super-nudge" having a vectored distribution of individual pulse trains. Also disclosed is the use of a plurality of independently actuated transducers for insonation using modulated, unfocused ultrasound from a multiplicity of directions, so as to improve therapeutic outcomes within an acceptable window of safety. Inadvertent use in hemorrhagic stroke is inevitable even with diagnostic imaging prior to treatment (transformation to hemorrhage may be insidious and can occur at any time during ischemic stroke—before or after initiation of treatment), and the device is also expected not to increase risk of bleeding, a complication in about 6.8% of individuals with stroke who receive the standard of care (0.9 mg/kg of r-tPA by IV bolus, followed by 0.1 mg/kg by IV drip).

6. There is a need to extend the window where r-tPA may be effectively used to mitigate the effects of stroke. The window as currently established is 3 hr post onset of stroke.

7. Problematically, variations in transducer output due to manufacturing variance can result in substantial inconsistencies in the insonation energy that is delivered transcranially. Advantageously, the transducer-to-transducer variability inherent in the manufacture of piezoelectric crystals is compensated by digitally varying boost voltage applied to each transducer individually according to calibration data stored with the apparatus. 8. Headsets 8. There is a need to build a device so that all functions except the on-off switch are automatic, and a device that functions autonomously, so that therapy may be administered by technicians and first responders without special training, or may be self-administered intermittently as needed, prophylactically, without requirement for physician intervention or oversight.

9. Over time, the devices of the invention may lead to methods of therapy that are not adjunct therapies to administration of r-tPA, which is the current standard of care. In addition to improved plasminogen activators in clinical development, various clotting cascade inhibitors are also under study, and will benefit from the improved acoustic streaming environment provided around the clot by co-therapy with ultrasound in the absence or presence of microbubbles.

10. Ultrasound is also known to increase endogenous release of nitric oxide (NO), and the device of the present invention achieves this safely so that it can be routinely applied, for example in treatment of migraine, where there is a hypoperfusion component. Other therapies are also envisaged, such as for headache, intracranial hypertension, and the more rare condition of hydrocephalus, which must be drained by surgical implantation of a cannula, or headache, all of which may benefit from non-invasive transcranial ultrasound therapy administered by a device configured with a built-in safe operating window for hands-free, operator-independent use, and may be operated by unskilled persons (and thus permit self-administration of ultrasound).

11. In one embodiment, the remote control unit is supplied with only an on-off/pause switch and a status indicator. The unit may be configured to automatically verify that the transducer arrays are acoustically coupled to the skull. The power supply is lightweight, typically less than 1 kg, and the entire controller assembly is pocket sized and is attached to the headset by a flexible cable, thus reducing the weight worn on the head to under 500 grams so that the user may be ambulatory during operation of the apparatus or may be transported without strain or discomfort.

According to one aspect of the invention, we have shown that pulse emissions driven by a voltage ($V_{p\text{-}p}$) configured to deliver an attenuated peak rarefaction pressure $P_{r,A}$ at depth $z_{sp}$ not to exceed 300 KPa and not to exceed a physiologically compatible thermal index are useful and safe, overcoming a technical hurdle encountered in the prior art.

In another embodiment, the invention includes an apparatus for non-invasive therapeutic application of transcranial ultrasound, which comprises: a) an adjustably tightenable circumcranial headset assembly configured with registration surfaces for engaging at least three external craniological landmarks of a skull so as to stereotactically position the headset assembly on the skull with respect to an intracranial target or targets; b) a plurality of transducer arrays, each transducer array comprising a plurality of non-focused ultrasound transducers, where the transducers are mounted on the headset so as to be stereotactically directed at the target or targets without need for diagnostic imaging guidance; and c) operatively attached to the headset, an electronic circuit with microcontroller, clock, memory, instruction set, a portable power and voltage supply, and on/off control for actuating the plurality of transducers in a repeating cycle, each cycle a metapulse comprising a plurality of trains of pulses, each train of pulses emitted intermittently and alternately at low duty cycle from selected transducers in a programmed sequence, whereby the skull is insonated with a stereotemporally modulated pattern of ultrasound without operator intervention and with low power consumption, the low duty cycle eliminating the need for assisted cooling.

In a preferred embodiment, the at least three external craniological landmarks are nasion, Rt otobasion superius, and Lt otobasion superius, the craniological landmarks forming an Isosceles triangle which defines a foundational reference plane containing the sphenoid shelf and the Circle of Willis of the skull, the triangle having a base, an apex, and a midline, the triangle and reference plane for stereotactically positioning the headset and for stereotactically aligning the nonfocused ultrasound transducers to insonate the vasculature of the Circle of Willis, the branches and junctions of the internal carotid and basilar arteries conjoined thereto, and the cerebral arteries projecting therefrom, thereby directing the insonation to the vasculature without need for diagnostic imaging guidance; and further where the plurality of transducer arrays comprise arrays selected from i) a right temporal transducer array and a left temporal transducer array or ii) a right temporal transducer array, a left temporal array, and an occipital transducer array, and where each transducer of the plurality of transducer arrays is independently controllable.

In a yet more preferred embodiment, the headset assembly may comprise a) an anterior headframe member configured for spanning ear to ear across the brow of the skull; the anterior headframe member generally "U-shaped" in form, with a first end and a second end contralaterally disposed thereon; b) a posterior headband member configured for spanning ear to ear under the occipital protuberance of the skull, the posterior headband having two ends, where each end is configured for inserted into one apposing end of the anterior headframe member, the anterior headframe member further comprising a tensioning mechanism for engaging the ends of the posterior headband member and tightening the headset circumcranially around the skull; and c) a nasion registration bracket or brace disposed anteriorly at a midpoint on the anterior headframe member and a nasion registration pad pendant therefrom, the nasion registration pad for engaging the nasion craniological landmark and offsetting the midpoint of the anterior headframe member by a height $h_1$; d) a pair of otobasion superius registration members slideably disposed contralaterally on the anterior headframe member, each otobasion superius registration member with a registration surface configured for engaging one each of the Rt otobasion superius craniological landmark and the Lt otobasion superius craniological landmark; and further where the headset is obliquely inclined relative to the foundational reference plane by the height $h_1$ anteriorly so that the anterior headframe member is raised above the eyes of the head, has clearance around the ears of the head, and where the posterior headband member is obliquely inclined below the reference plane by a height $h_2$, thereby engaging the underside of the occipital protuberance of the skull when stereotactically positioned thereon.

In one embodiment, each registration surface of the otobasion superius registration member is an earpiece, and the Rt earpiece is fixedly mounted in relation to the Rt temporal transducer array and the Lt earpiece is fixedly mounted in relation to the Lt temporal transducer array, the earpieces each having dimensions for stereotactically positioning each temporal transducer array in acoustic contact with a temporal acoustic window when the nasion registration pad is seated on the nasion and each earpiece is seated on one the otobasion superius, thus forming a tripod defining the foundational reference plane. A simple embodiment is thus a stereotactic registration system where the headset rests on the ears and nose in the manner of a pair of eyeglasses, having a nosepiece and a pair of earpieces for stereotactically positioning the transducers.

In selected embodiments, the posterior headband may include an occipital transducer array, the occipital transducer array disposed on the posterior headband to as to be proximate to the occipital acoustic window under the occipital prominence when the posterior headband is circumcranially tightened around the skull. Advantageously, the apparatus can thus be installed by persons with little skill or training.

The apparatus of the invention finds use in non-invasively reversing, controlling or preventing ischemic stroke of the cerebral vasculature; in non-invasively reversing, controlling or preventing atheroma of the cerebral vasculature; in non-invasively reversing, controlling or preventing headache, migraine, or hydrocephaly; in combination with recombinant tPA in treatment of stroke; in non-invasively dispersing or generating an endogenous mediator of a physiological state; and surprisingly may be used non-invasively outside a 3 hour window post onset of stroke. Surprisingly, the apparatus is also effective when used for migraine.

More generally, the apparatus of the invention functions as an automaton, without the need for operator invention once emplaced on a head of a wearer and actuated. The apparatus may thus be used for self-administered transcranial ultrasound. These and other aspects of the invention are described and illustrated in more detail below.

BRIEF DESCRIPTION OF THE DRAWINGS

The teachings of the present invention can be readily understood by considering the following detailed description in conjunction with the accompanying drawings, in which.

Landmarks for positioning a headset may be selected from nasion, Lt otobasion superius (LtOBS), Rt otobasion superius (RtOBS), tragion, mandibular condyle, zygomatic arch, prosthion, or occipital prominence, while not limited thereto. At least three are selected to define a triangle. As a matter of convenient field use by untrained operators, the nasion/LtOBS/RtOBS triad has proven well suited. Mounting assemblies on the headset are configured with surfaces for engaging the landmarks of the head and stereotactically orienting the transducer arrays with respect to temporal and occipital acoustic windows into the cerebral arteries of said cranium so that the device may be used without further adjustment that would require an imaging modality such as transcranial Doppler, which is not readily available to first responders, for example.

Figure 6A:
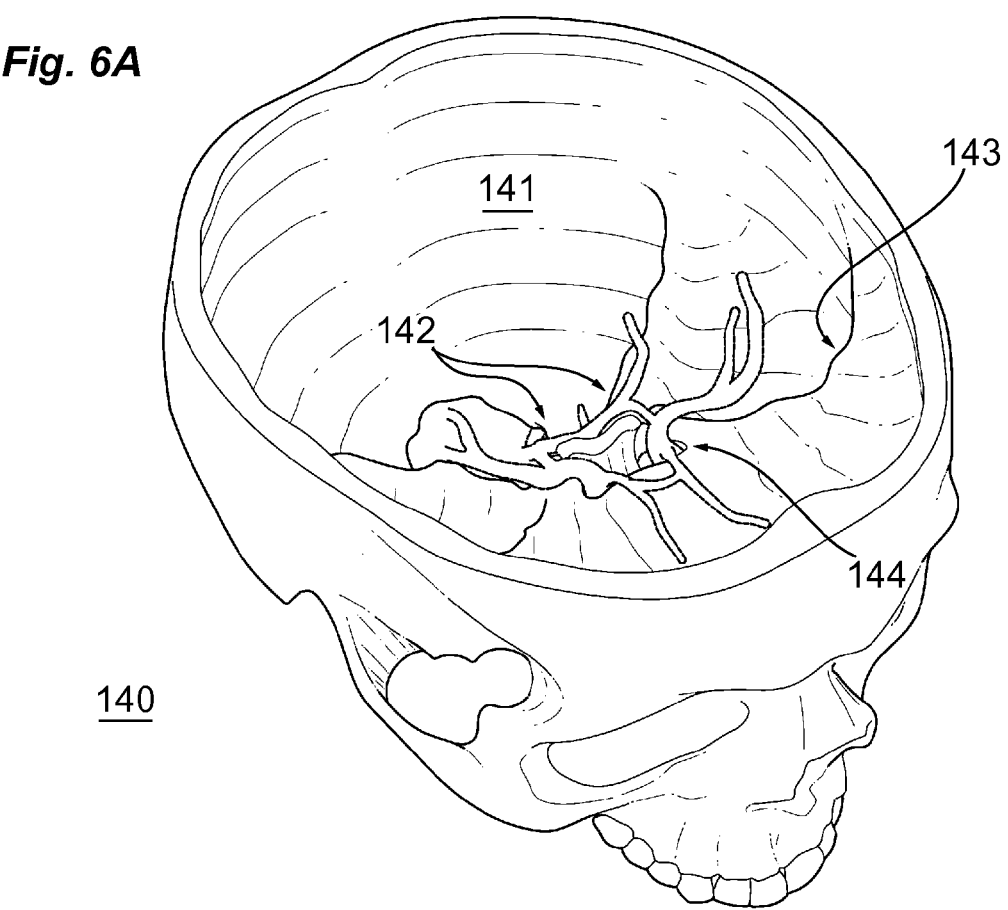
Figure 6B:
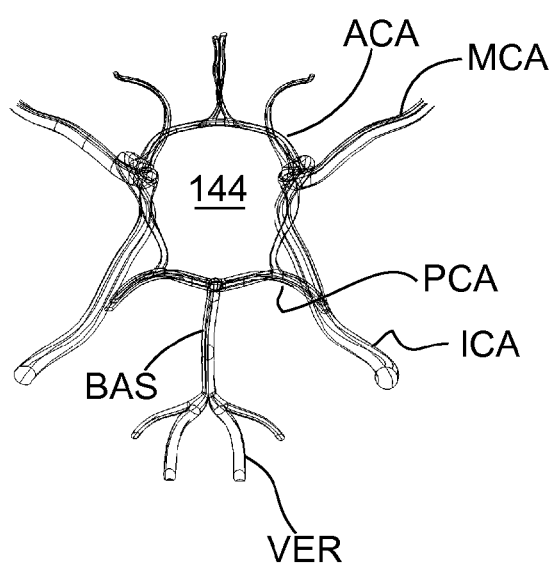
Figure 6C:
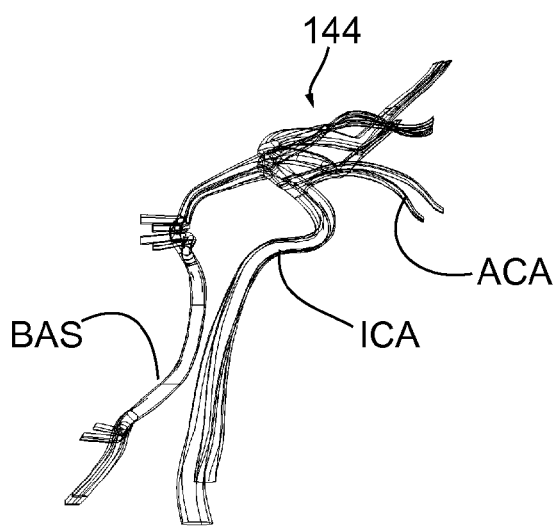

FIG. 6A is an exposed view of the cranial bones forming the sphenoid shelf and of the associated cerebral arteries. FIGS. 6B and 6C are views of the major cerebral arteries (superior and lateral views respectively) and the Circle of Willis, which can be seen resting tangential to the anterior and posterior clinoid processes and projecting in plane from the shelf or ledge formed by the greater and lesser wings of the sphenoid bone, an anatomical feature termed herein the "sphenoid shelf", which forms the base of the anterior fossae and overlies and is generally co-planar with the orbital tracts. These vascular structures are of particular interest as intracranial targets for treatment of ischemic stroke.

Figure 7A:
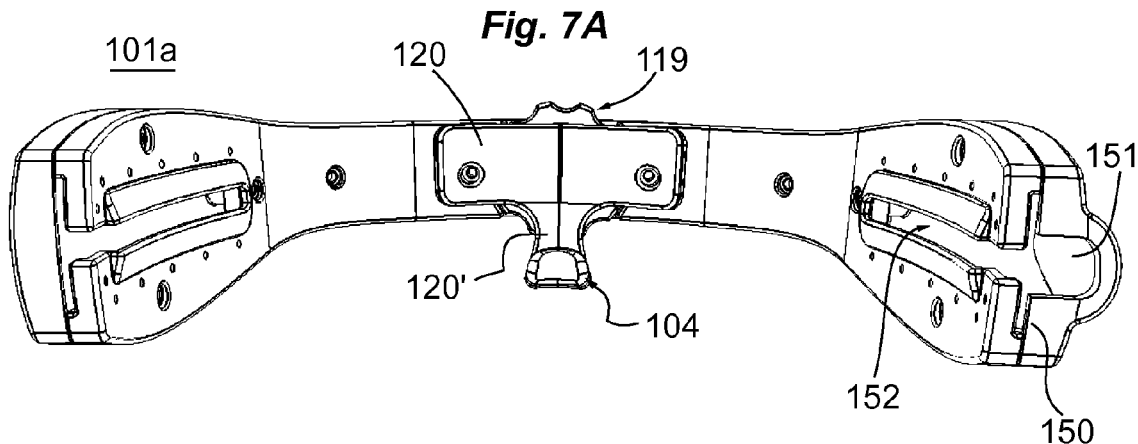

FIG. 7A shows an internal view of the headset with nasion registration bracket and pad for aligning the transducer arrays with the nasion and sphenoid shelf.

Figure 7B:
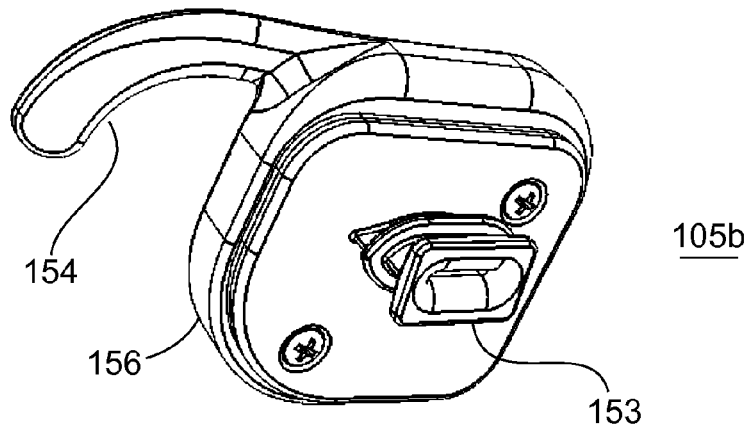

FIGS. 7B and C are external views of the temporal transducer array subassemblies.

Figure 7C:
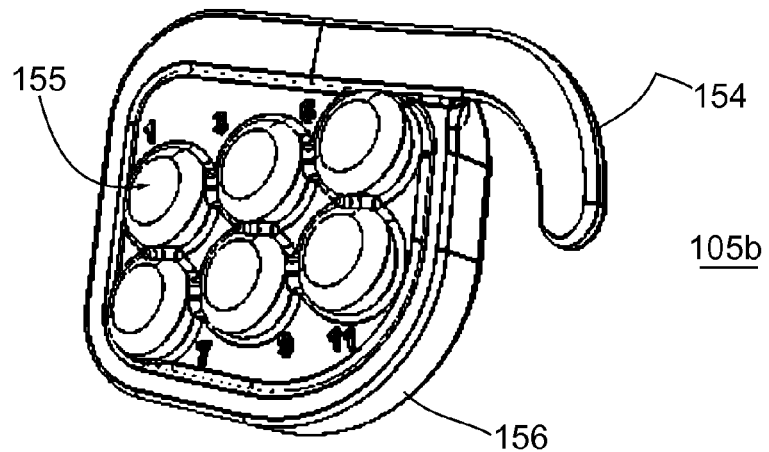
Figure 7D:
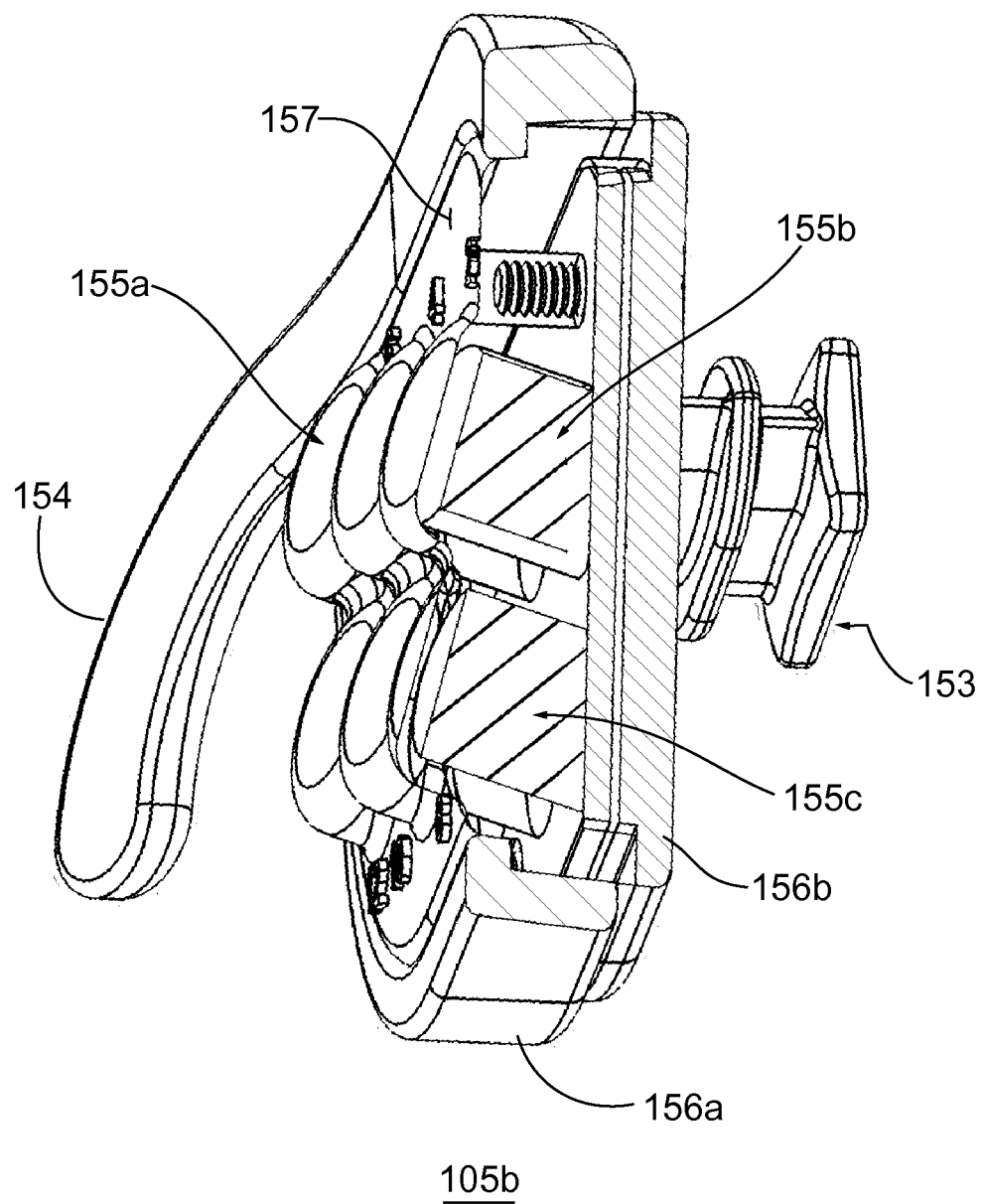

FIG. 7D is a cutaway view showing detailed structure of the temporal transducer array and housing.

Figure 8A:
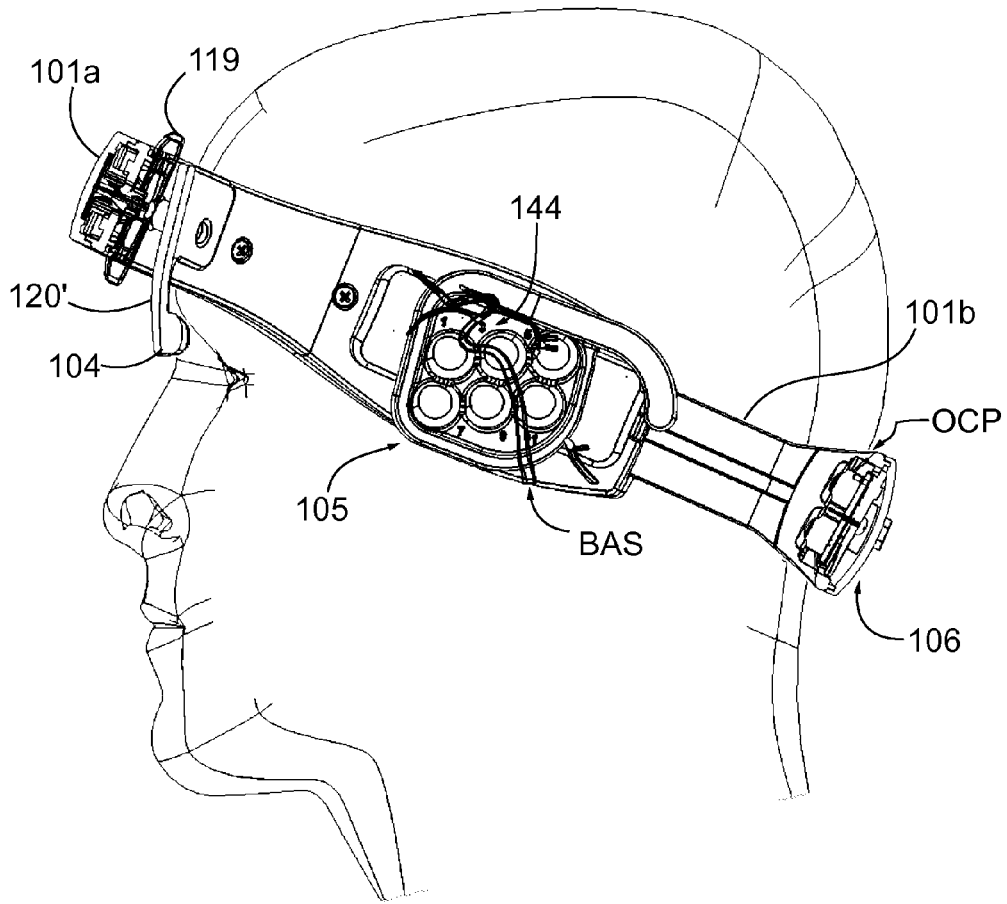

FIG. 8A depicts a temporal transducer array as it interfaces with the temporal acoustic window on the ipsilateral side of the skull, as seen in an exposed view of the transducer arrays and central cerebral vasculature.

Figure 8B:
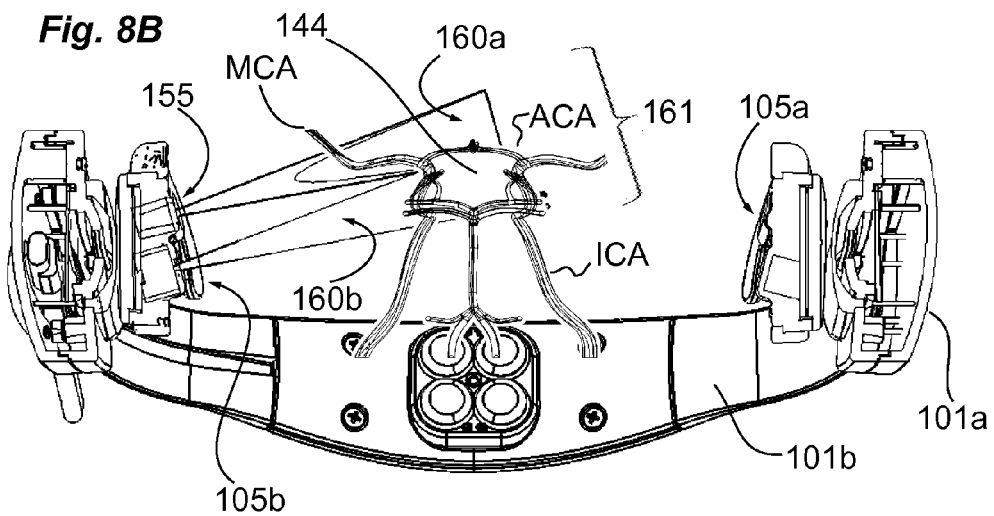

FIG. 8B is a cross-sectional exposed view showing how ultrasound beams of the temporal transducer array are directed at the cerebral vasculature. The cone is shown for purposes of representation and is not intended as a literal depiction of an acoustic wavefront emanating from a transducer.

Figure 9A:
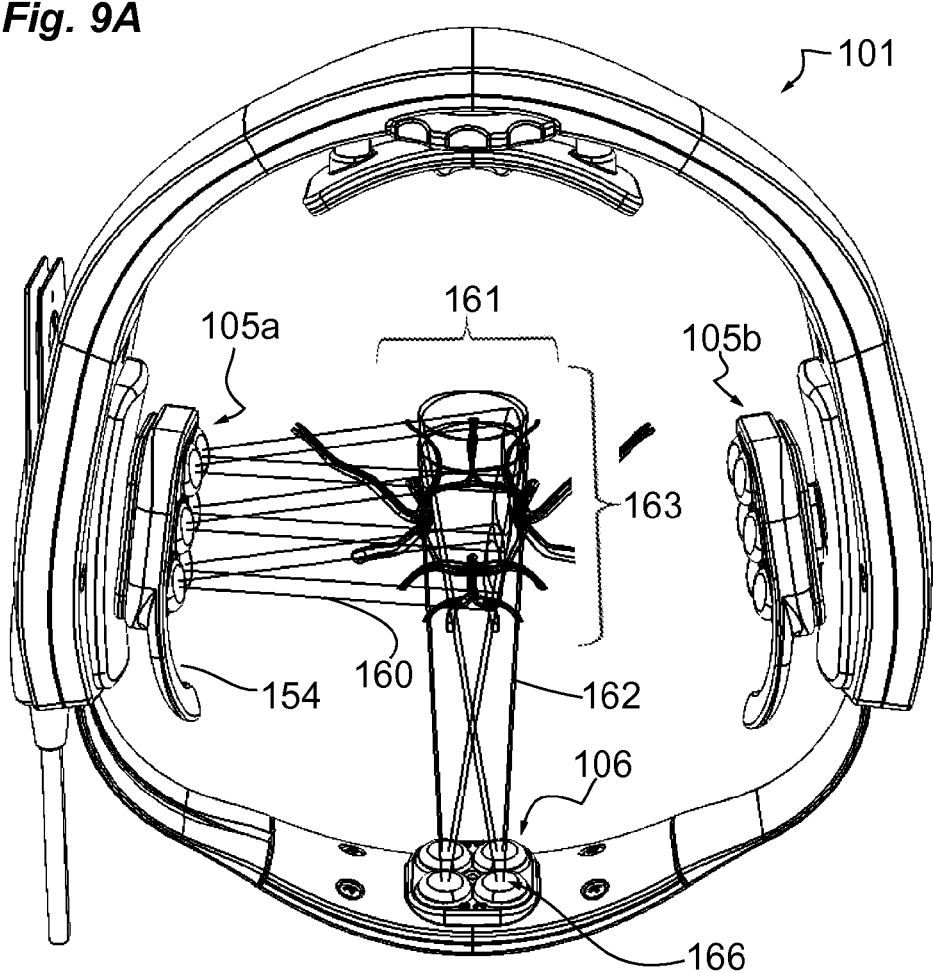

FIG. 9A depicts a superior view of the headset assembly, showing multiple temporal and occipital ultrasound beams figuratively as superimposed on the cerebral vasculature.

Figure 9B:
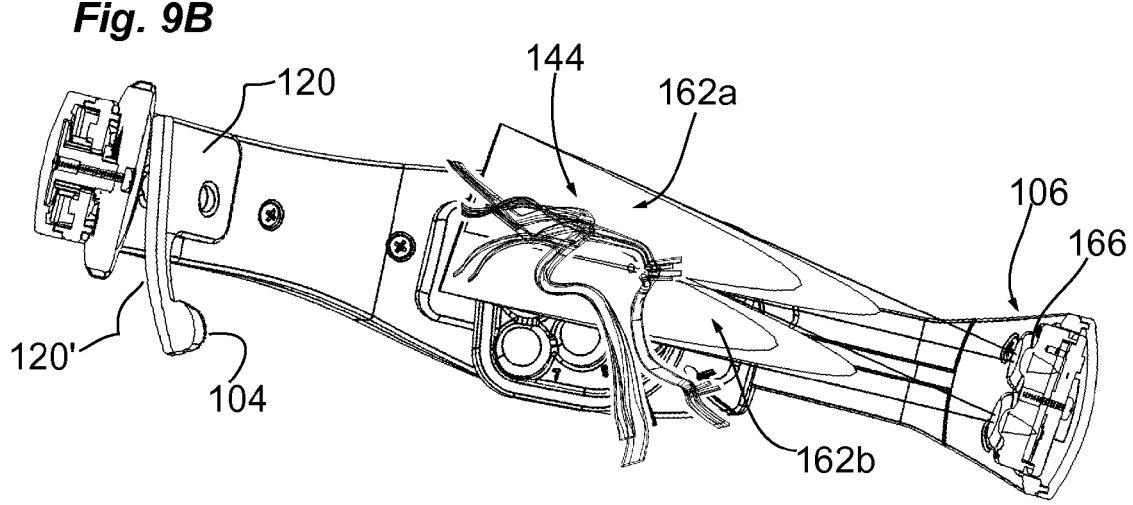

FIG. 9B is a cutaway view showing how ultrasound beams of the occipital transducer array are directed at the cerebral vasculature.

Figures 10A, 10B:
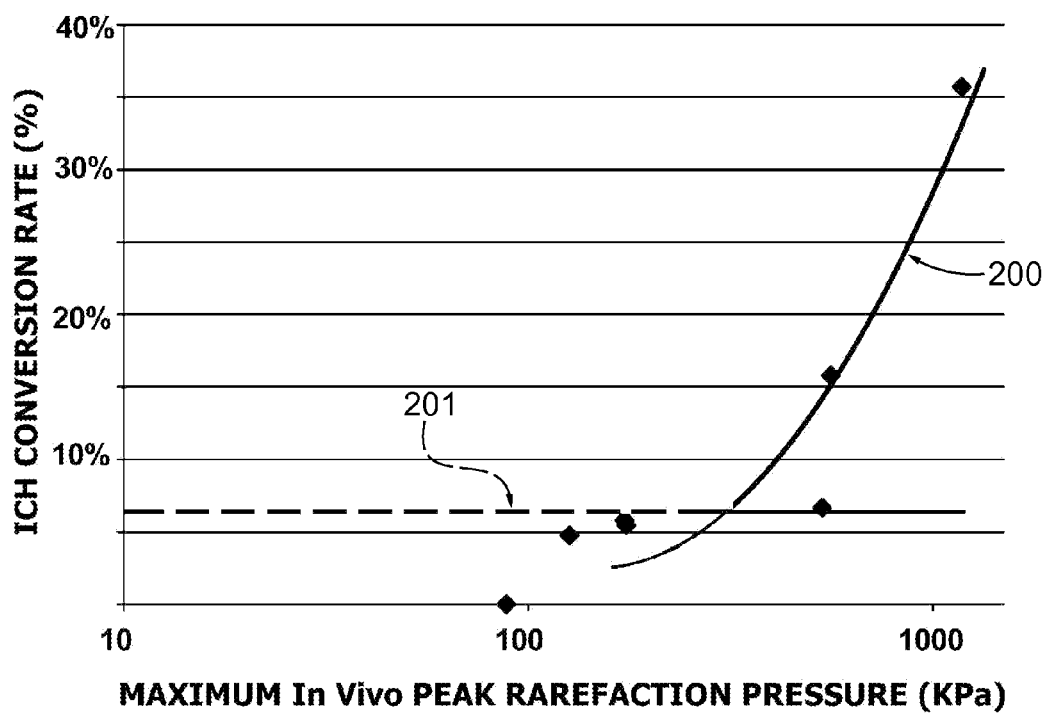

FIG. 10A is a table describing summary results of a Phase II human trial with a prior art device for administering transcranial ultrasound.

FIG. 10B plots the relationship between peak rarefaction pressure and ICH conversion (%) as determined here from analysis of data from clinical trials.

Figure 11A:
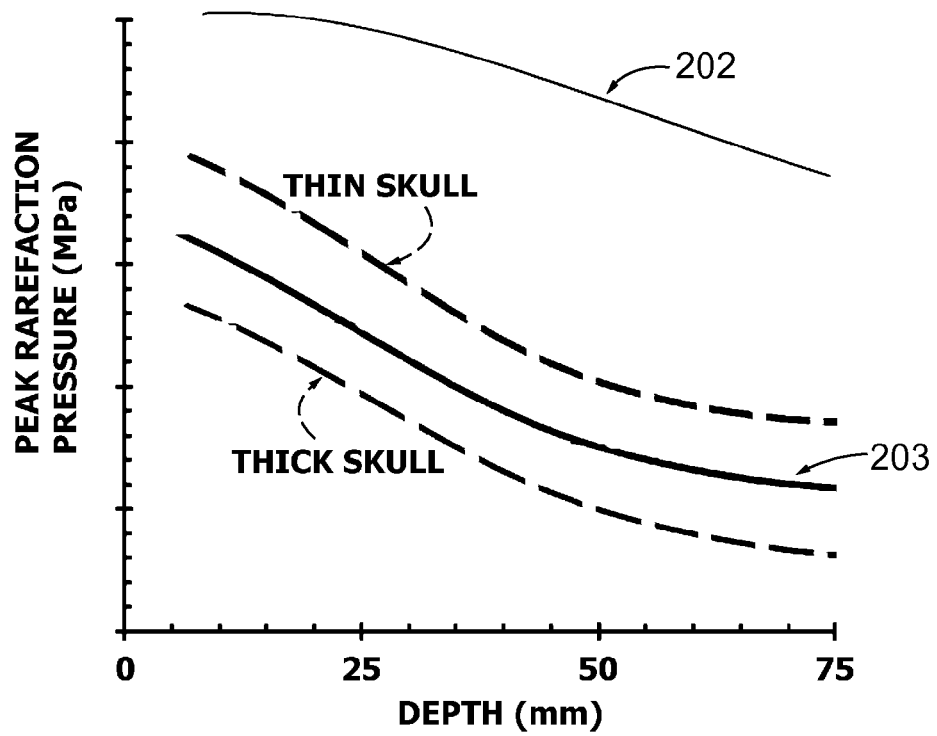

FIG. 11A is a plot of peak rarefaction pressure illustrating the effect of thick and thin skull phenotype on peak rarefaction pressure as a function of depth at 1 MHz.

Figure 11B:
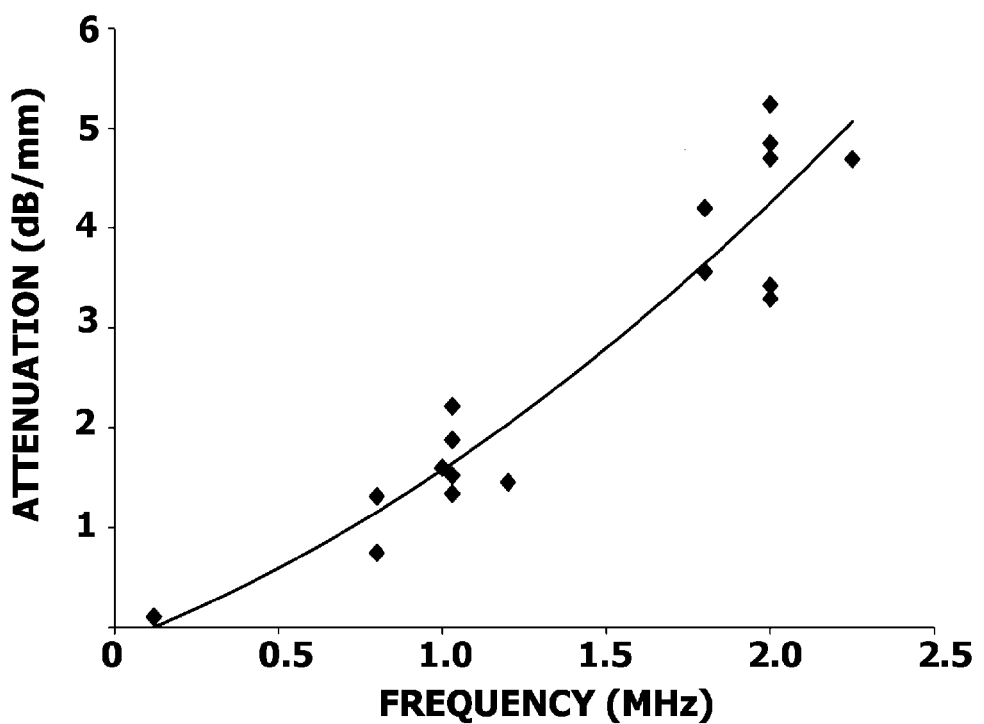

FIG. 11B is a curve fit for attenuation coefficient ($A_{Temp\text{-}BONE}$) versus frequency for temporal bone.

Figure 12A:
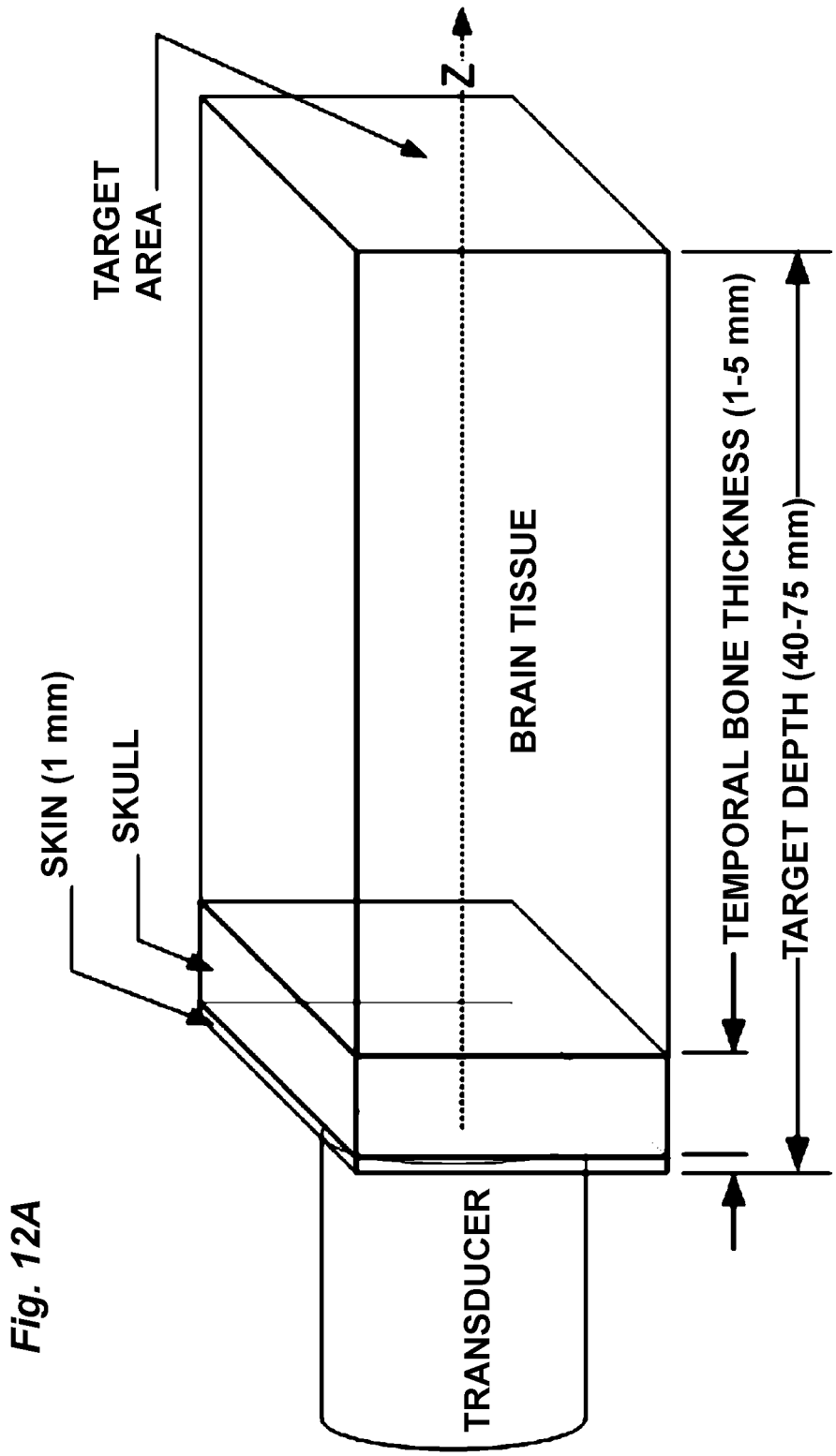
Figure 12B:
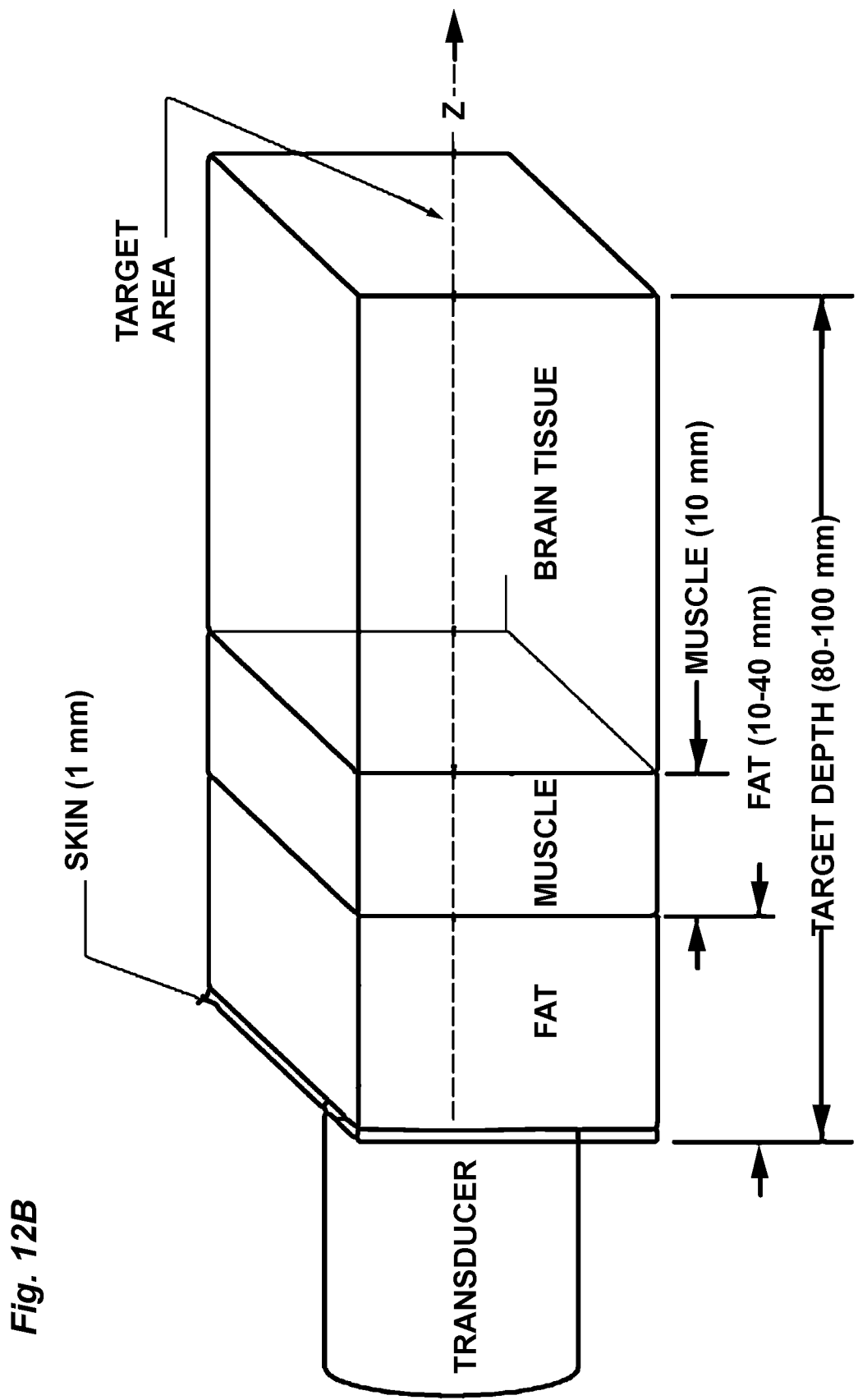

FIGS. 12A and 12B are renderings of physical models for analysis of attenuation profile as a function of depth for a trans-temporal transducer (FIG. 12A) and for a transducer apposing the occipital acoustic window (FIG. 12B).

Figure 13A:
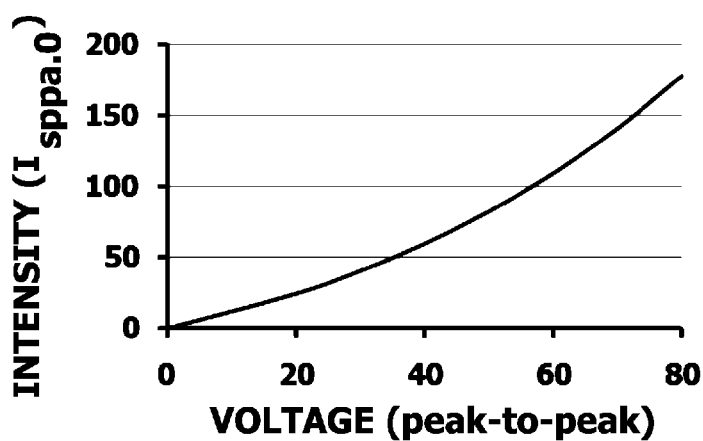

FIG. 13A is a plot of voltage ($V_{p\text{-}p}$) versus $I_{sppa.0}$ (W/cm$^2$), showing transducer output under tank conditions.

Figure 13B:
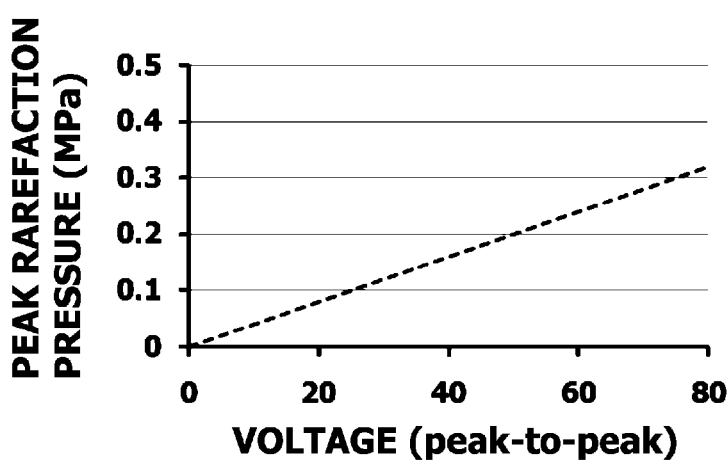

FIG. 13B is a plot of voltage ($V_{p\text{-}p}$) versus peak rarefaction pressure ($P_r$) at a $z_{sp}$ characteristic of the transducer in situ.

Figure 13C:
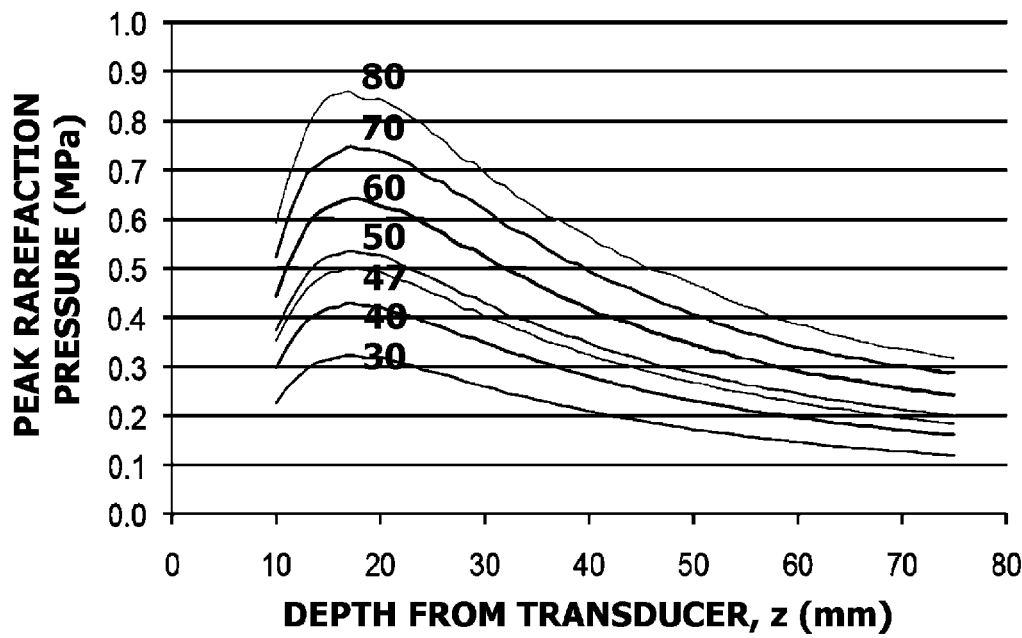

FIG. 13C shows peak rarefaction pressure as a function of depth for selected increments in transducer voltage ($V_{p\text{-}p}$) from 30 to 80 $V_{p\text{-}p}$.

Figure 14:
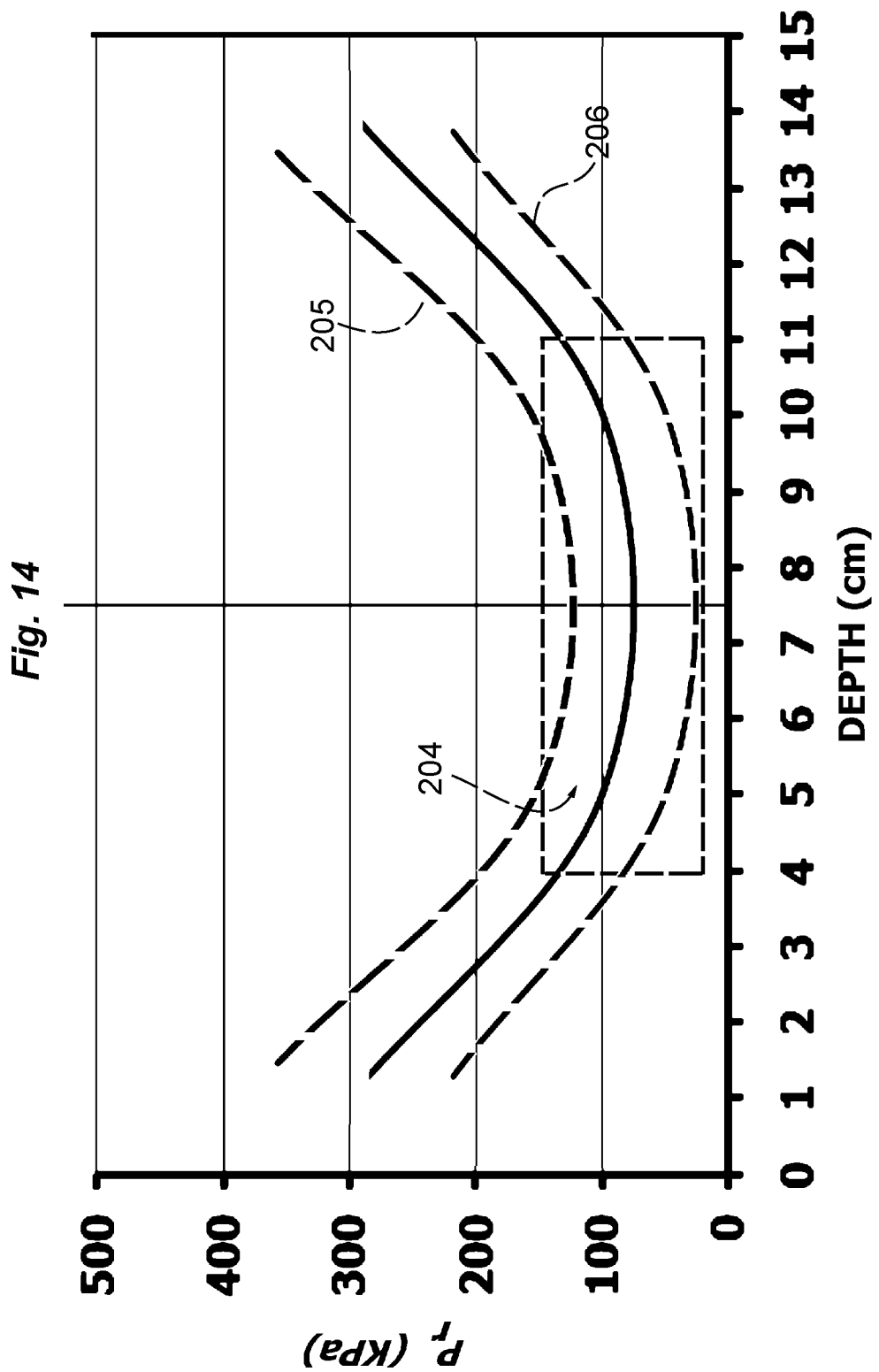

FIG. 14 plots temporal-to-temporal depth (i.e., from one side of the skull to the other) on the abscissa and attenuated peak rarefaction pressure on the ordinate. Three curves are shown: thin skull, mean skull, and thick skull variants.

Figure 15A:
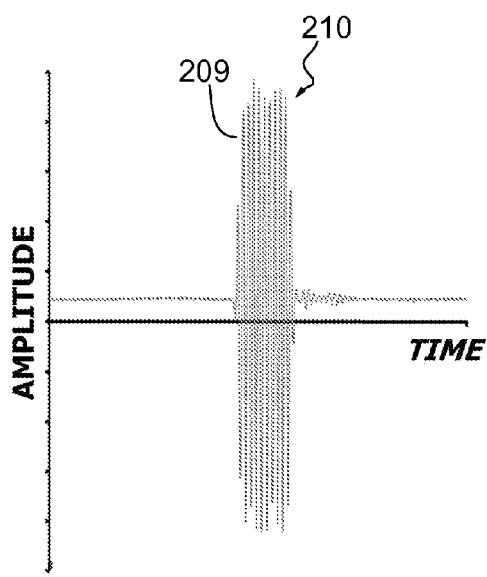
Figure 15B:
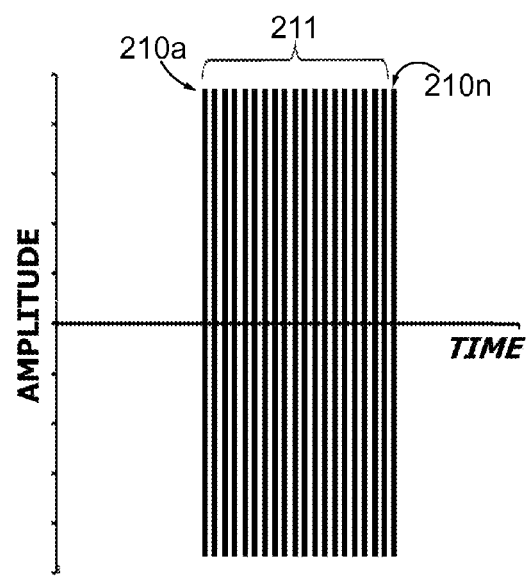
Figure 15C:
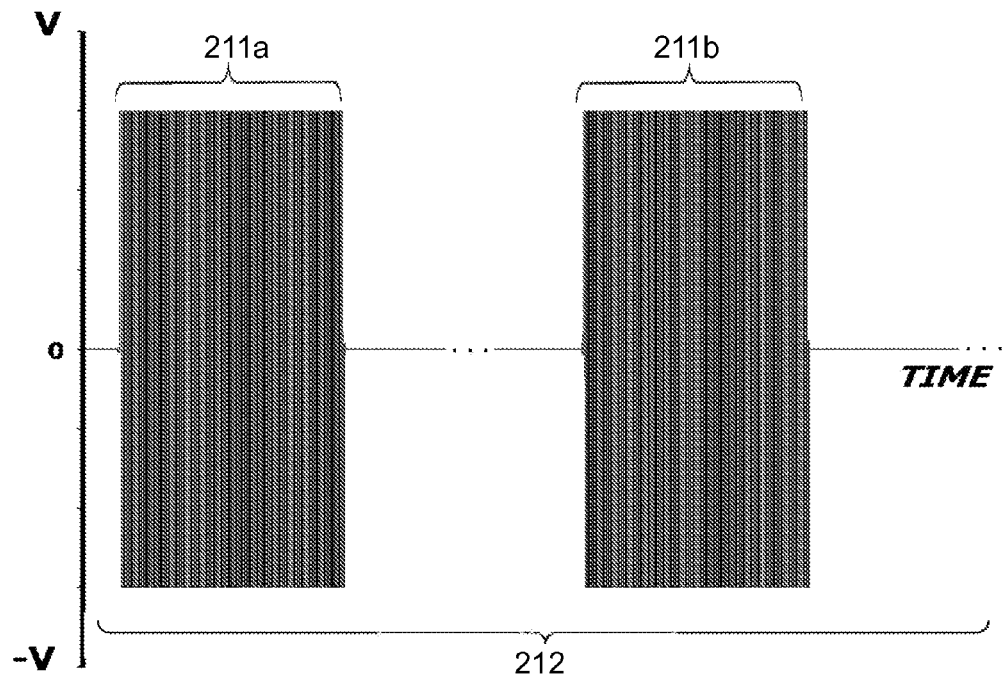

FIG. 15A illustrates a pulse consisting of about 12 sinusoidal sound waves. FIG. 15B illustrates a pulse train consisting of 20 pulses. FIG. 15C illustrates a pair of pulse trains, each pulse train consisting of multiple pulses in series.

Figure 16A:
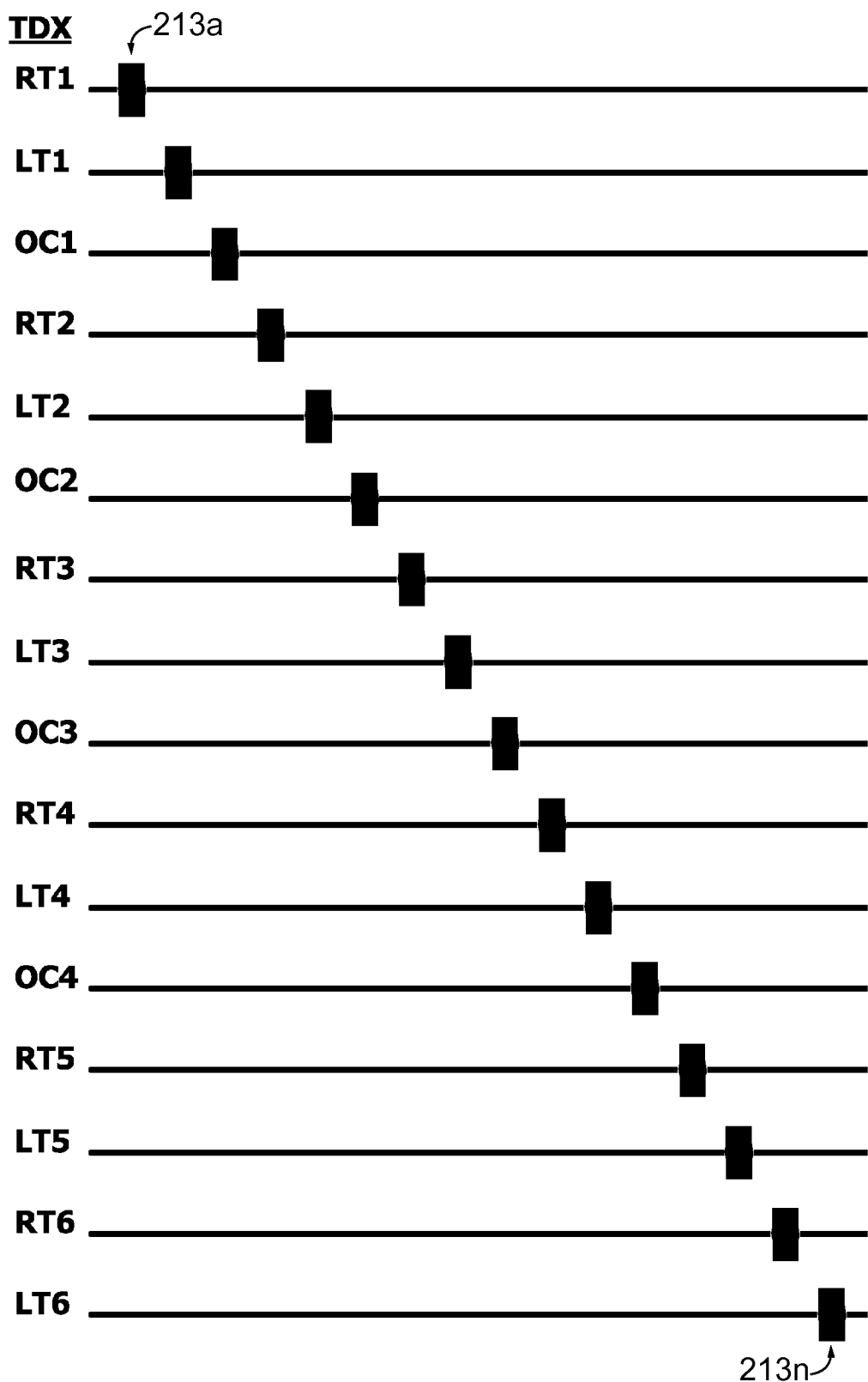

FIG. 16A is an example of a complete cycle involving sixteen ultrasonic transducers. Combining the traces, the figure represents a pattern of asynchronous ultrasonic pulse train emissions (i.e., a "metapulse cycle") from an array of sixteen transducer crystals, where each crystal is directed at a distinct anatomical target and is fired once per cycle in isolation.

Figure 16B:
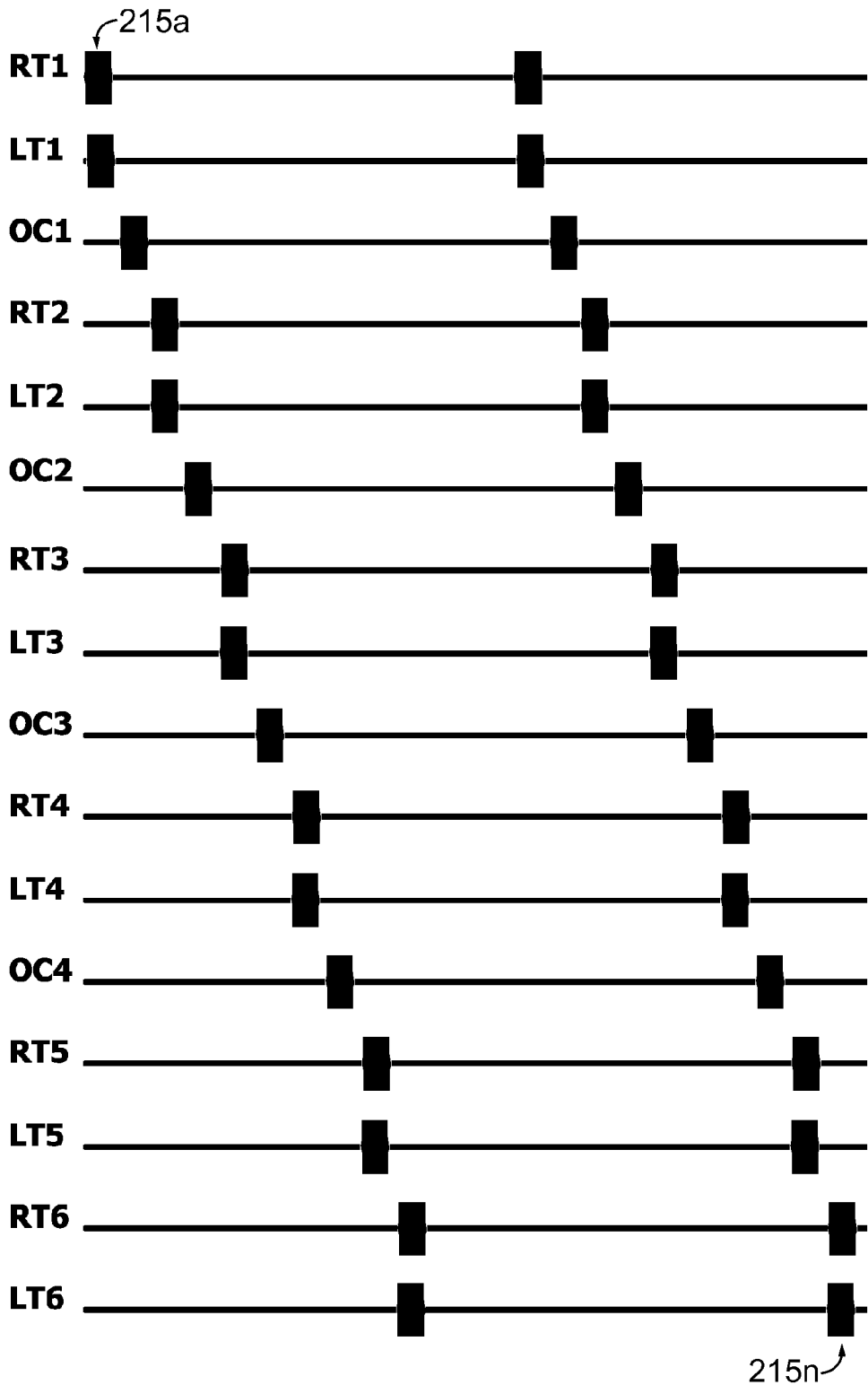

FIG. 16B is a second example of a metapulse cycle, here having duplex transducer firings.

Figure 16C:
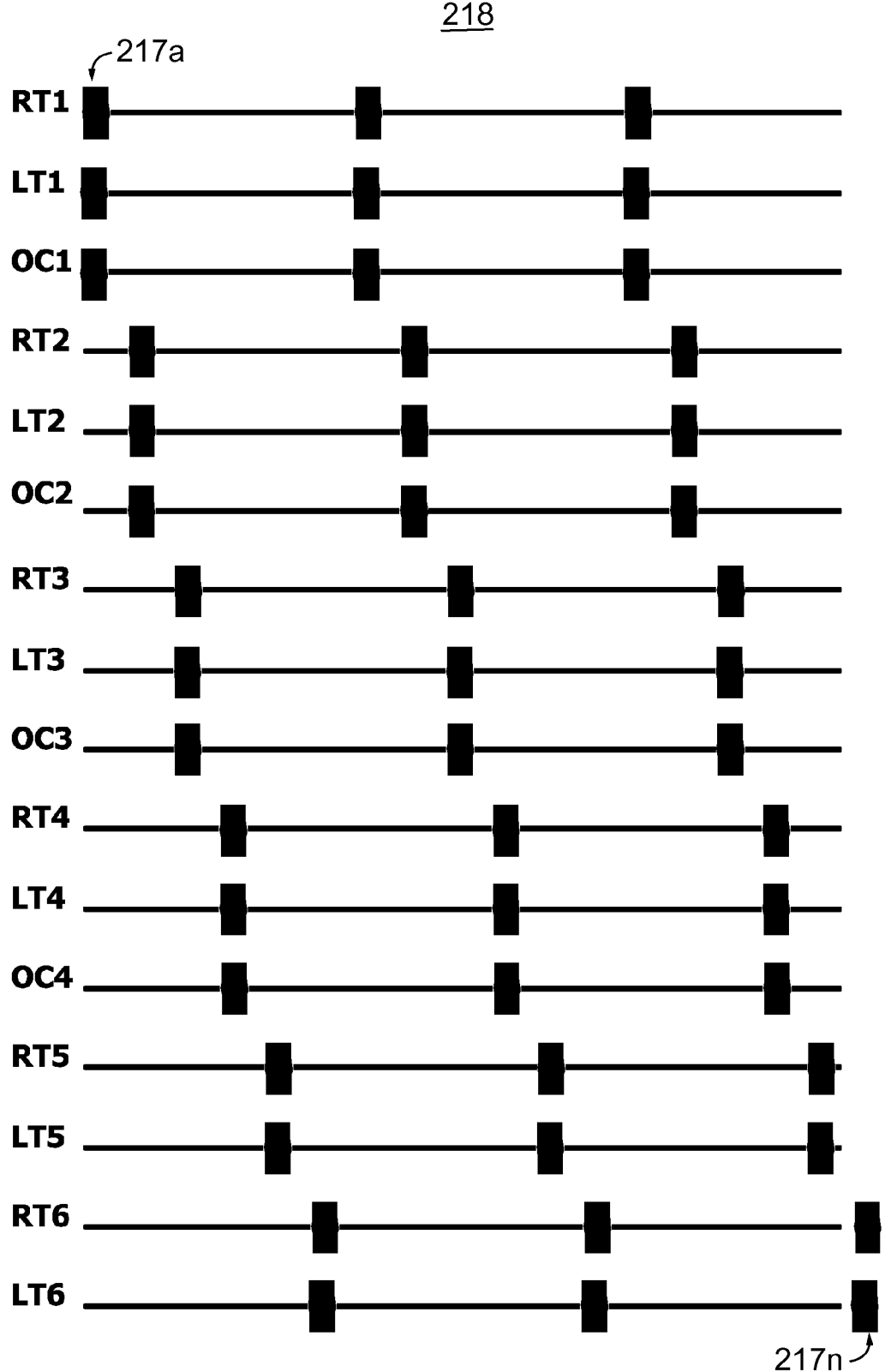

FIG. 16C is a third example of a metapulse insonation cycle, here having triplex simultaneous transducer firings.

Figure 17:
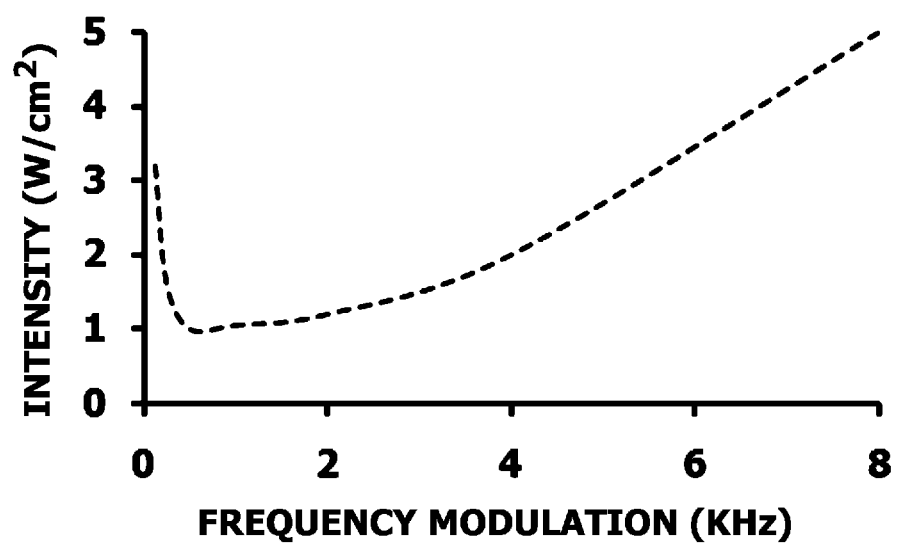

FIG. 17 quantifies the audible sensation of ultrasound exposure as a function of modulated pulse repetition frequency.

Figure 18:
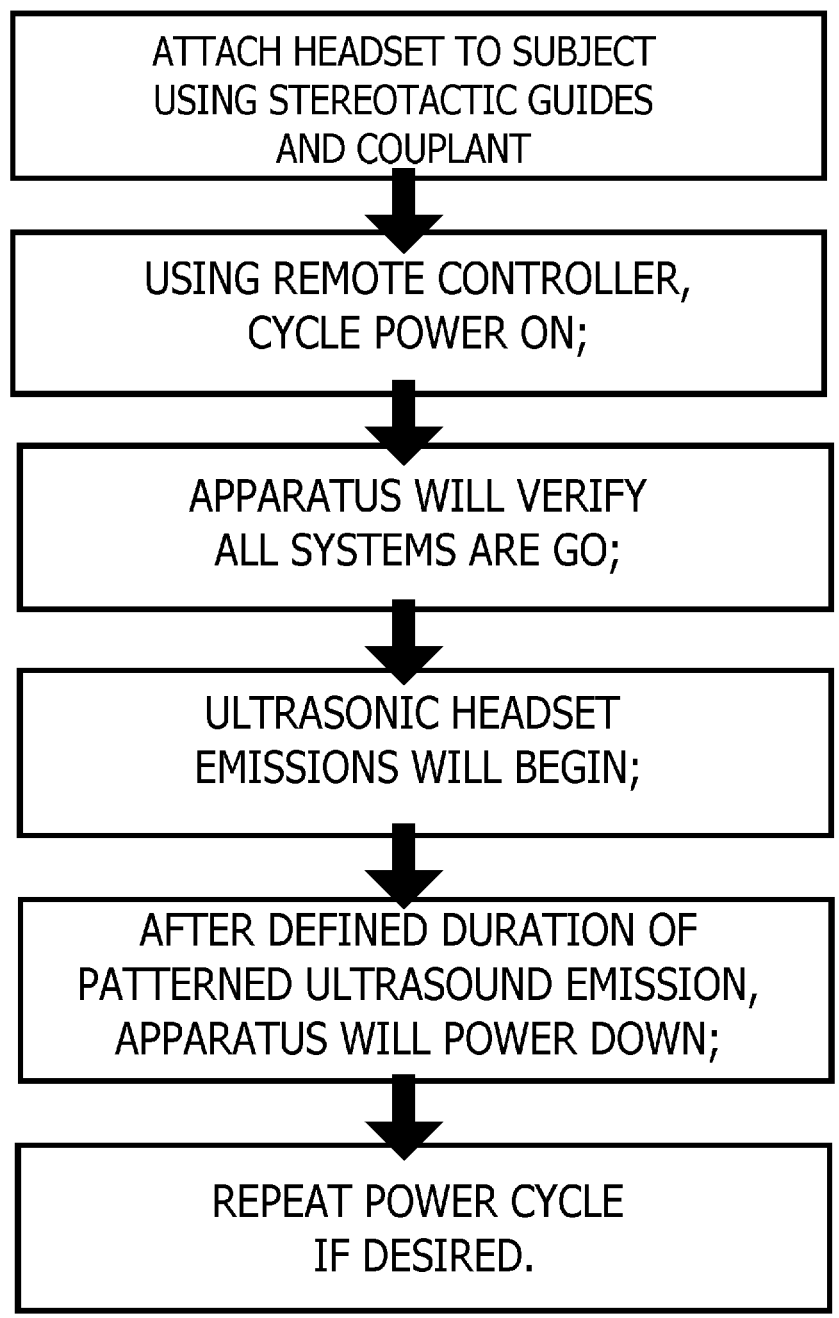

FIG. 18 is a flow diagram for autonomous "hands free" operation of the apparatus.

Figure 19:
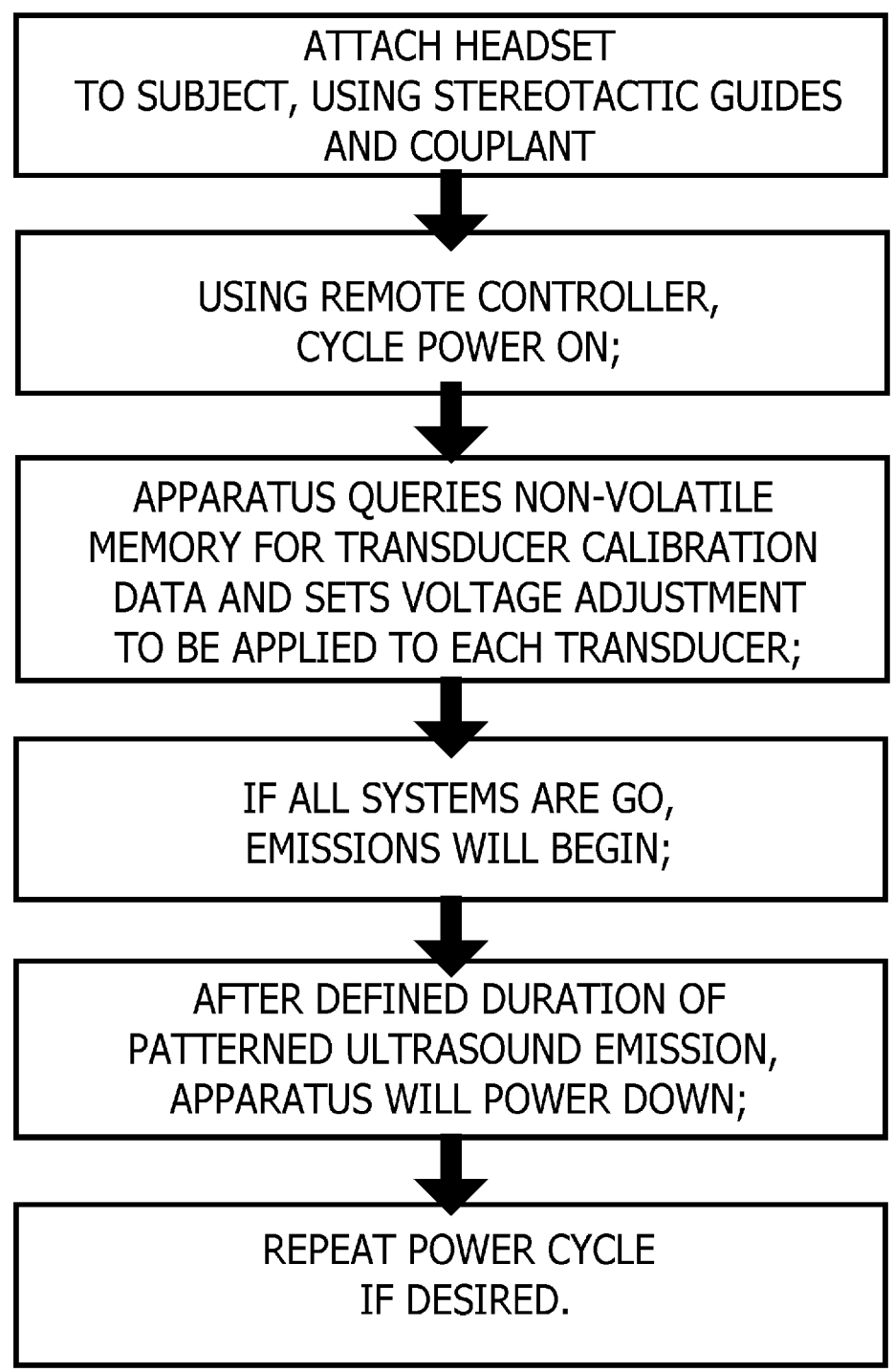

FIG. 19 describes the steps of a method for operation of the device for a defined insonation duration, where transducer voltage is adjusted to compensate for transducer-to-transducer variability.

Figure 20A:
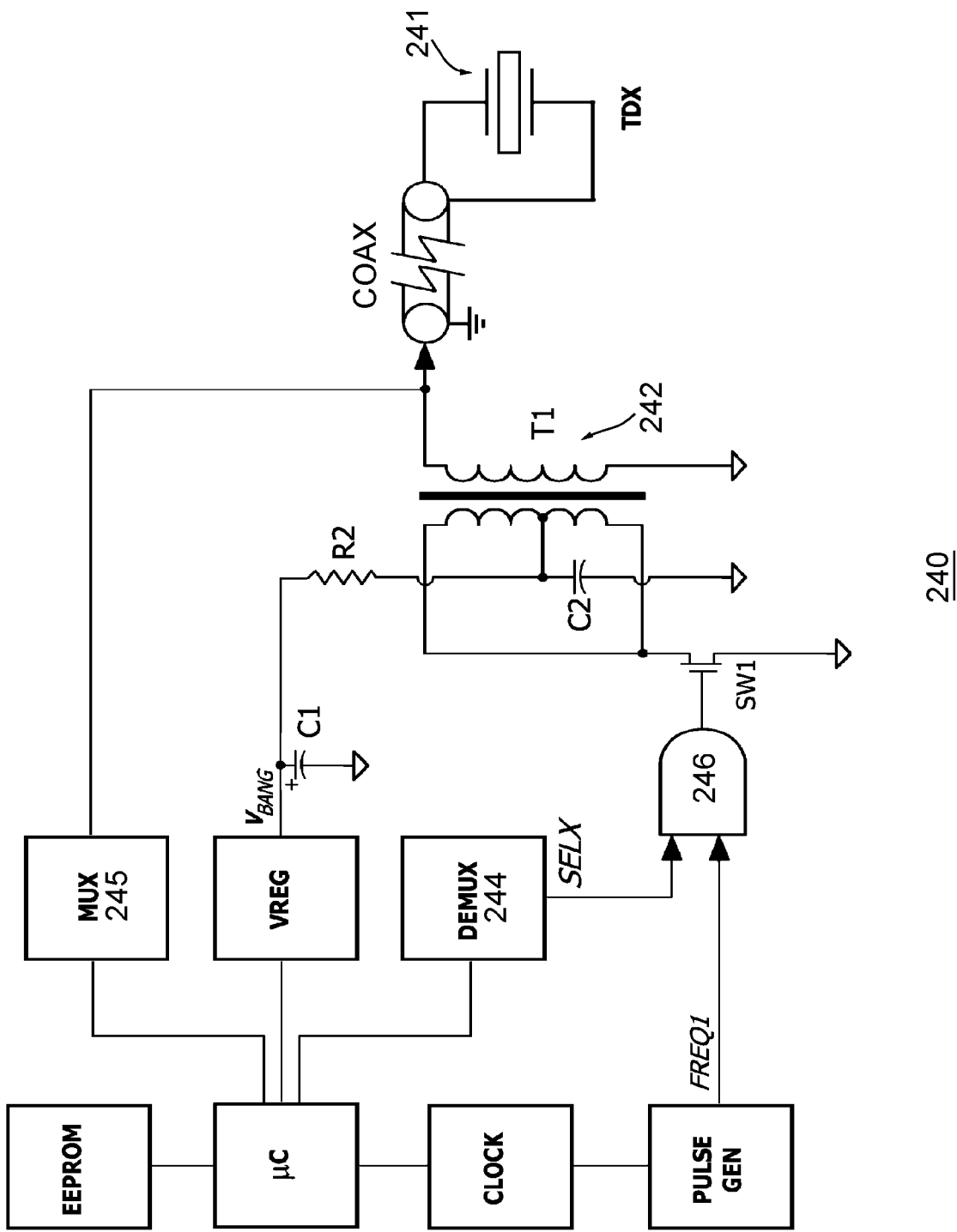

FIG. 20A is a block diagram of an energy efficient electronic circuit (240) for patterned ultrasonic insonation with adjustable amplitude.

Figure 20B:
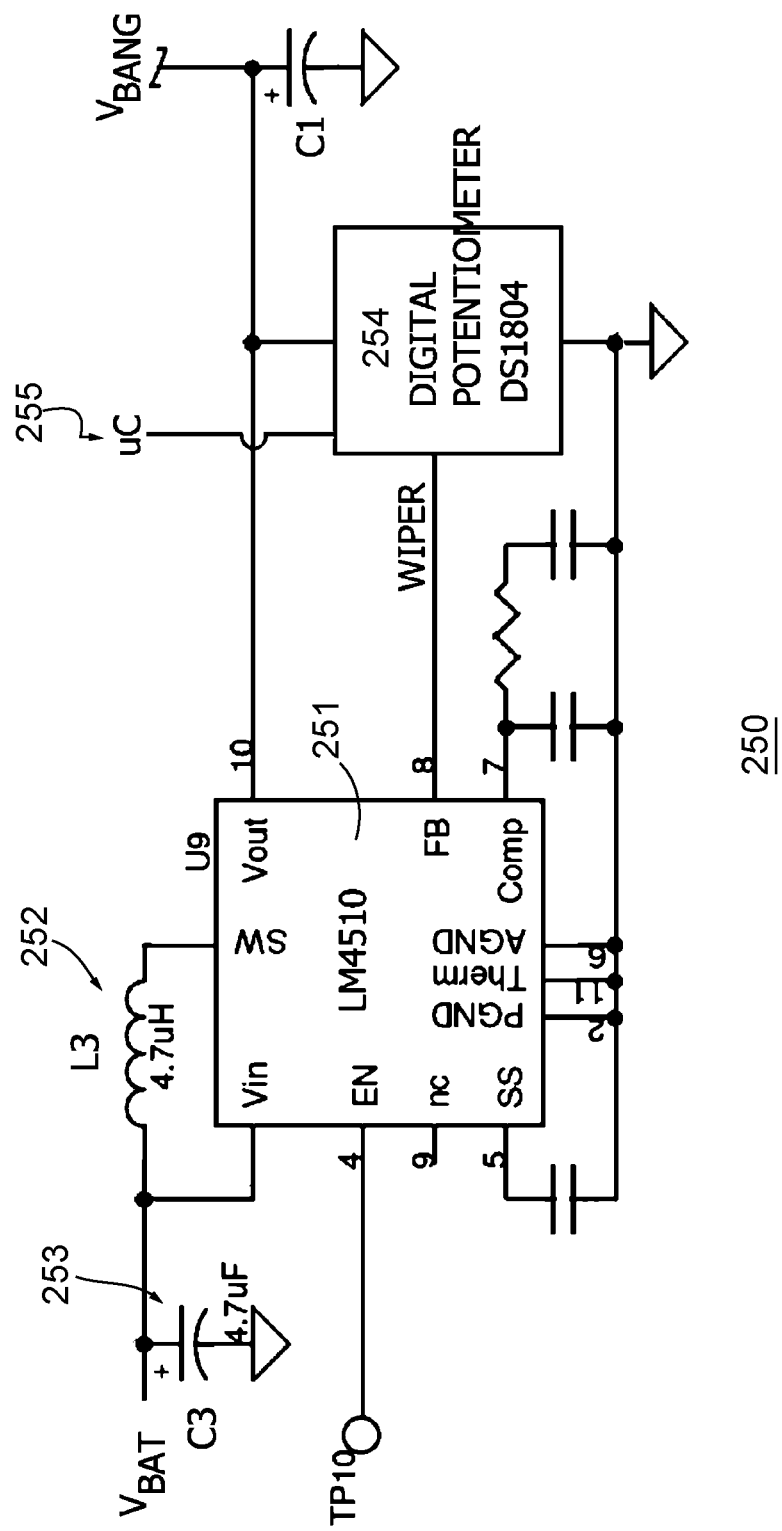

FIG. 20B is a schematic showing a transducer voltage regulation circuit (250) at the component level.

Figure 20C:
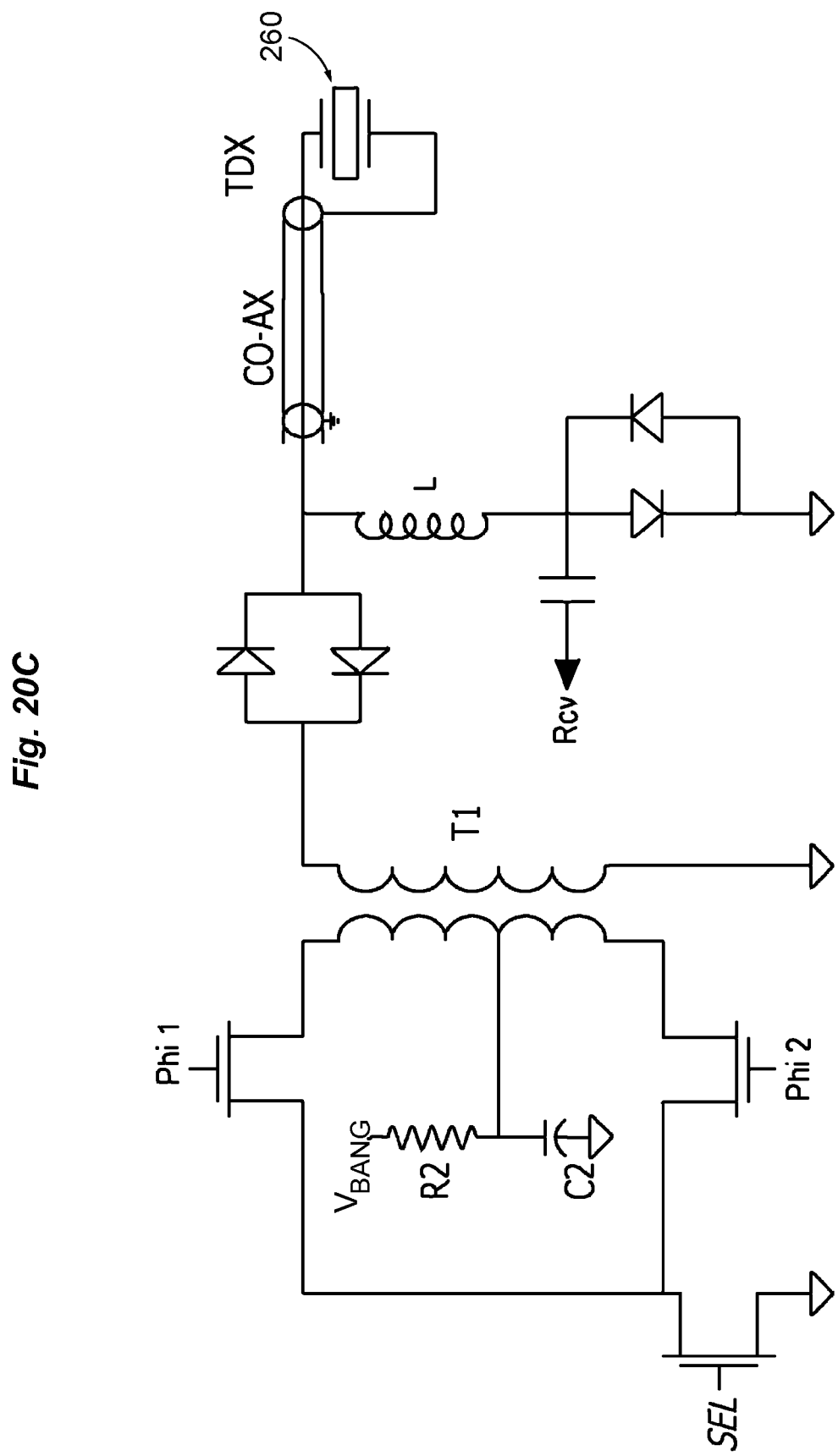

FIG. 20C is a schematic view of a simplified ultrasonic pulse generator circuit with a receive circuit.

Figure 20D:
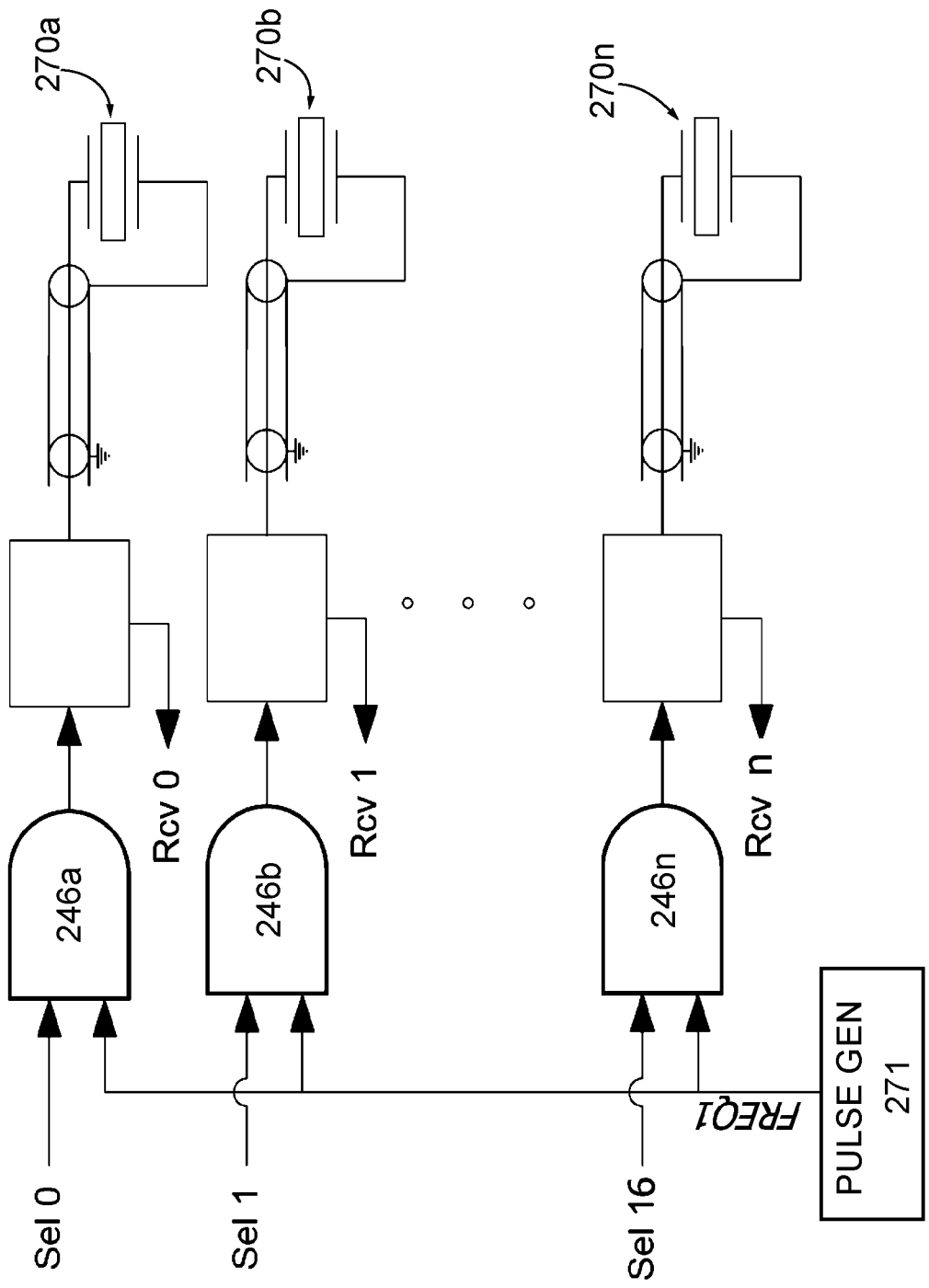

FIG. 20D illustrates multiplexed operation for sending and receiving signals to and from a transducer array.

Figure 21:
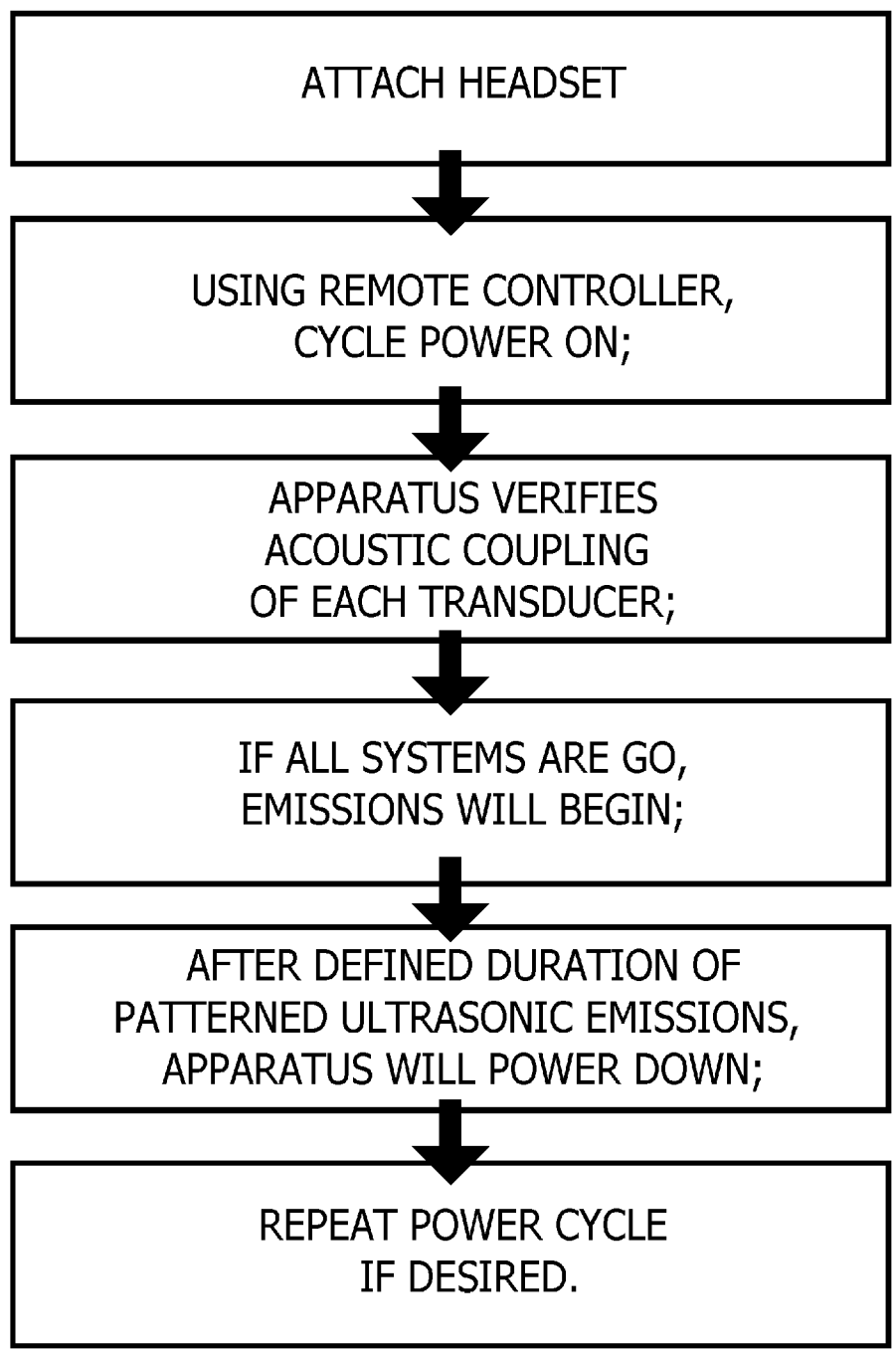

FIG. 21 is a block diagram for autonomous detection of acoustic coupling under each transducer.

Figure 22A:
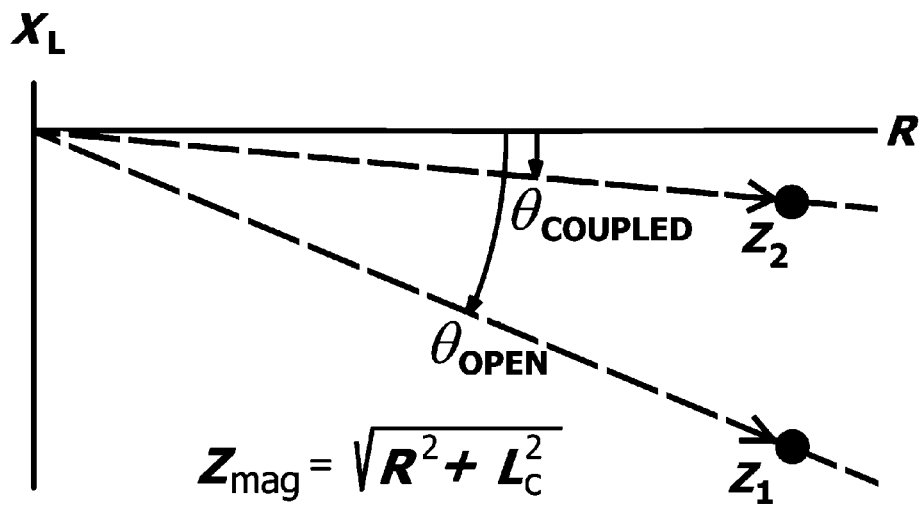
Figure 22B:
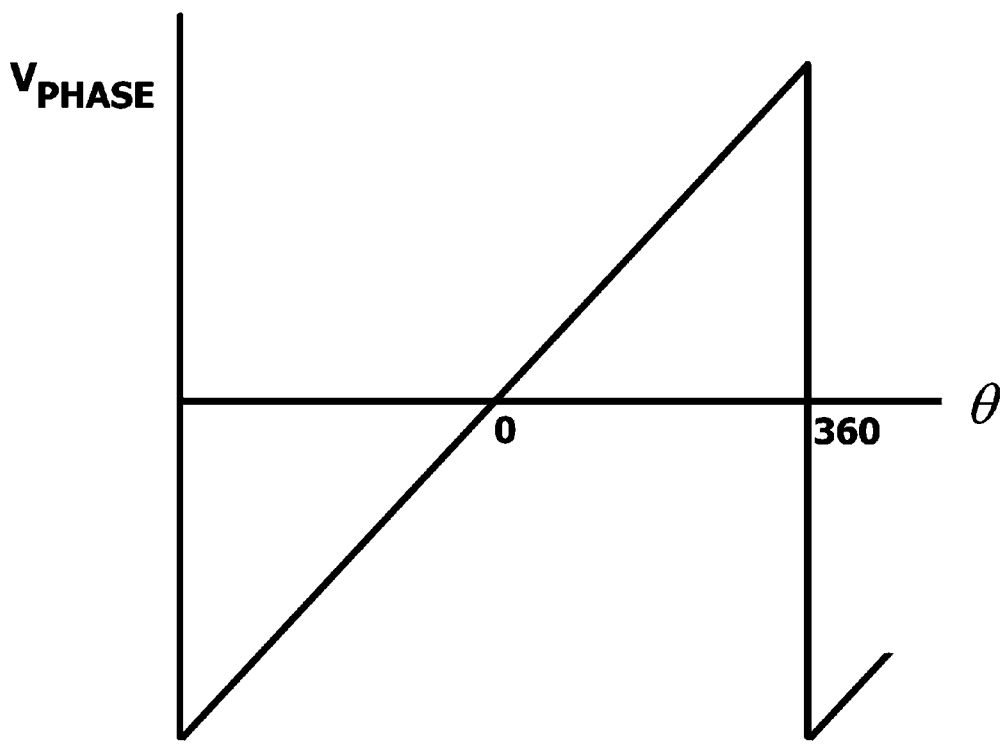

FIGS. 22A and B describe the use of phase angle to verify acoustic coupling. FIG. 22B plots voltage output corresponding to phase angle for a coupling verification circuit of FIG. 23.

Figure 23:
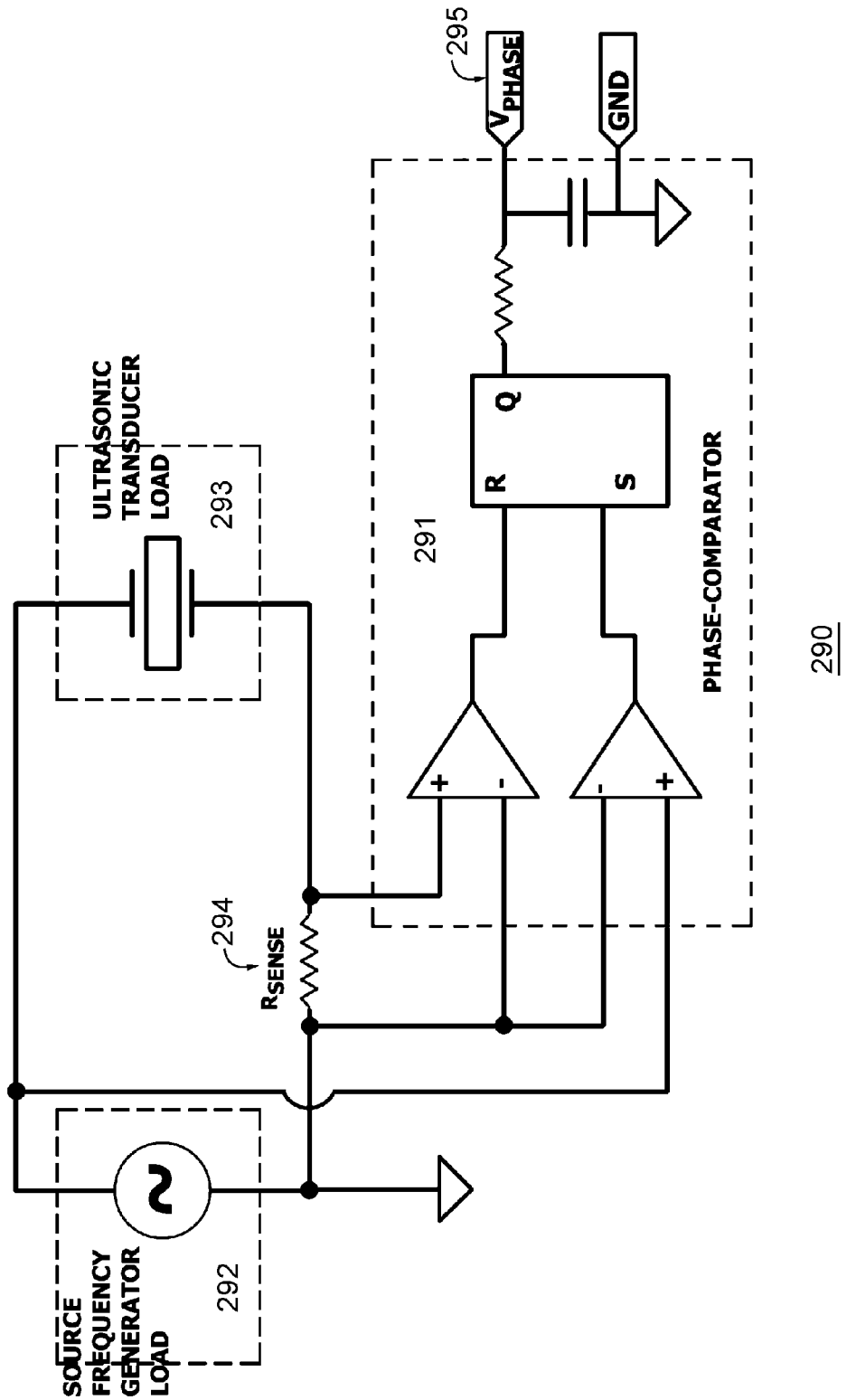

FIG. 23 illustrates schematically a coupling verification circuit (290) which relies on a voltage comparator having the output of FIG. 22B.

Figure 24:
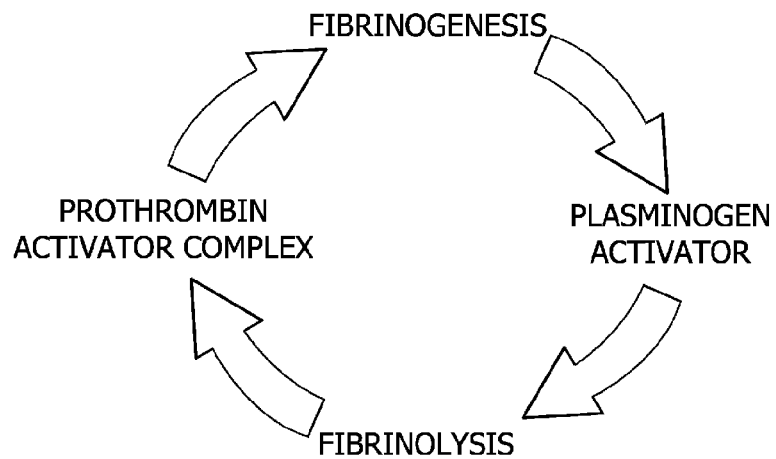

FIG. 24 depicts schematically the competing cycle of fibrinogenesis (coagulation) and fibrinolysis (thrombolysis).

Figure 25:
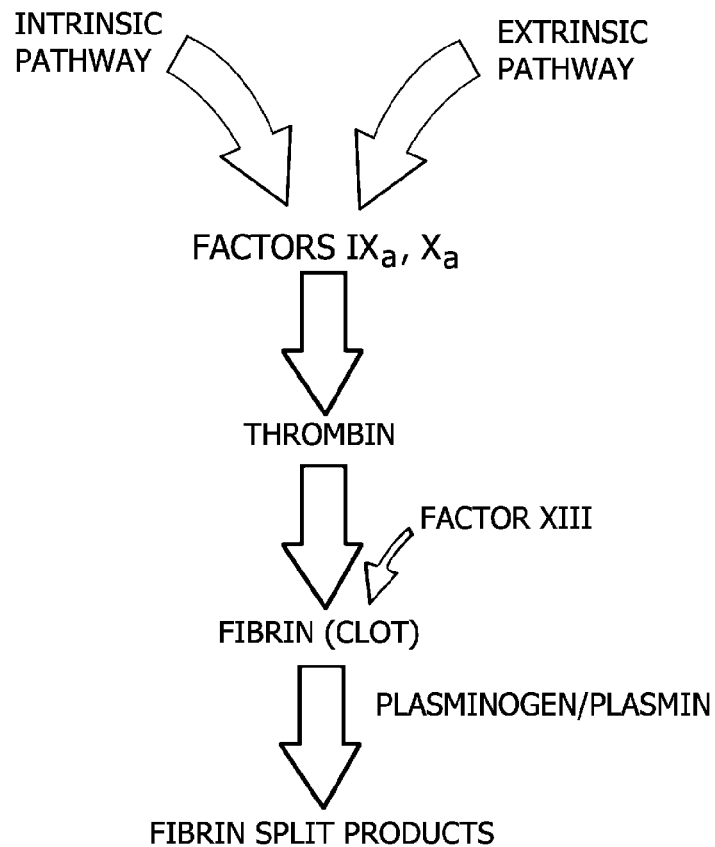

FIG. 25 is a schematic of the major limbs of the classical coagulation model.

Figure 26:
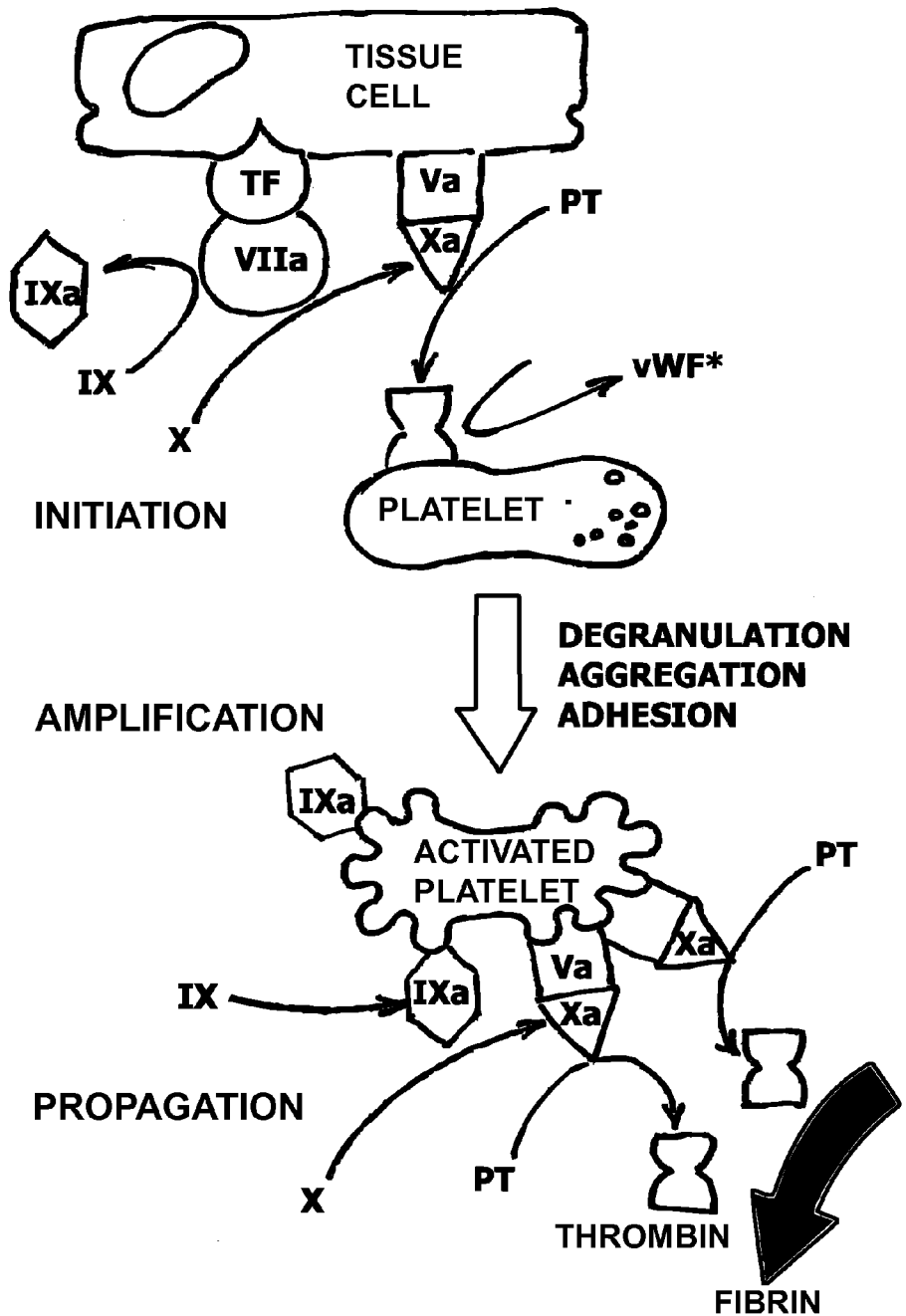

FIG. 26 is a schematic of the "cellular model" of coagulation (after Monroe 2001 Thromb Haemost 85:958-965).

Figure 27:
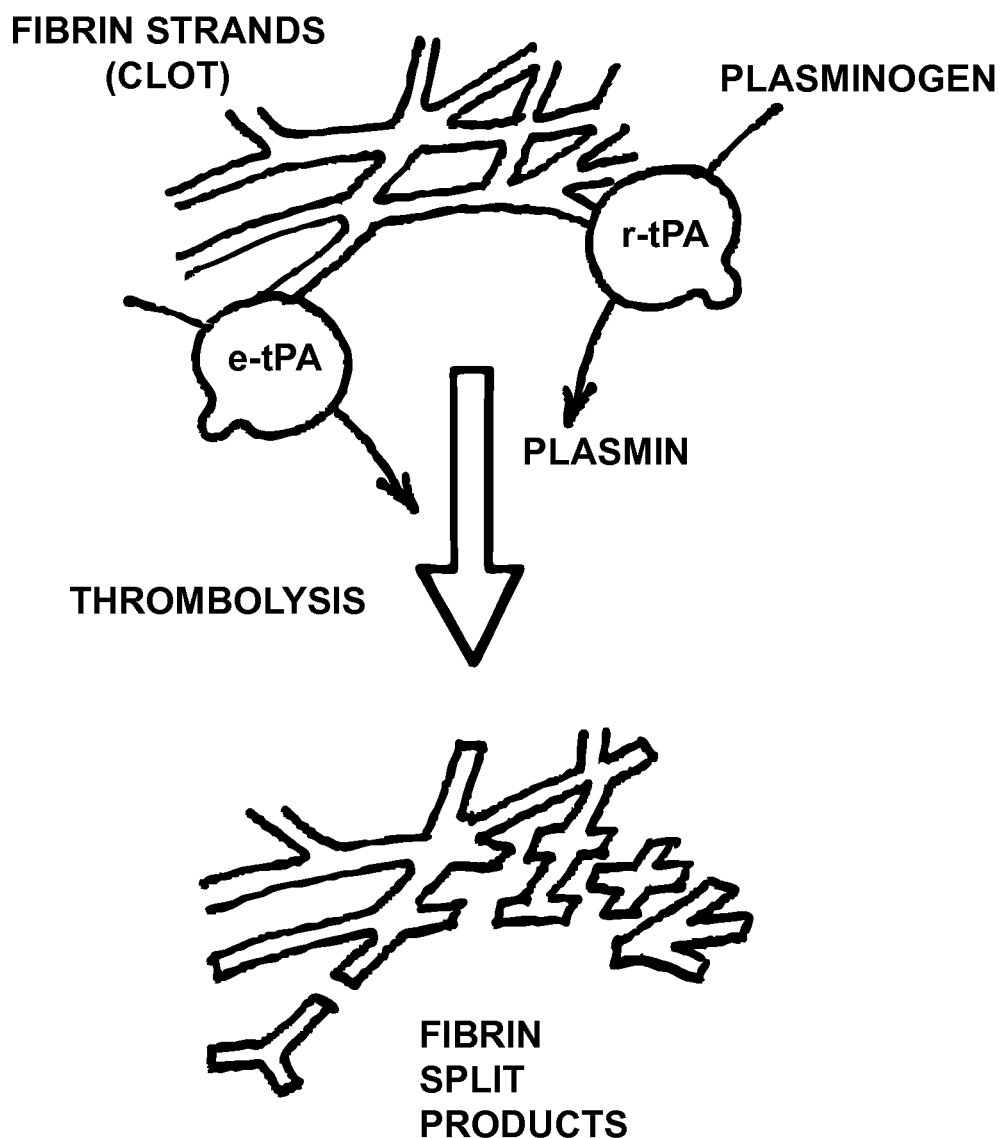

FIG. 27 depicts fibrinolysis involving endogenous (e-tPA) and/or exogenous (r-tPA) tissue plasminogen activator.

Figures 28A, 28B:
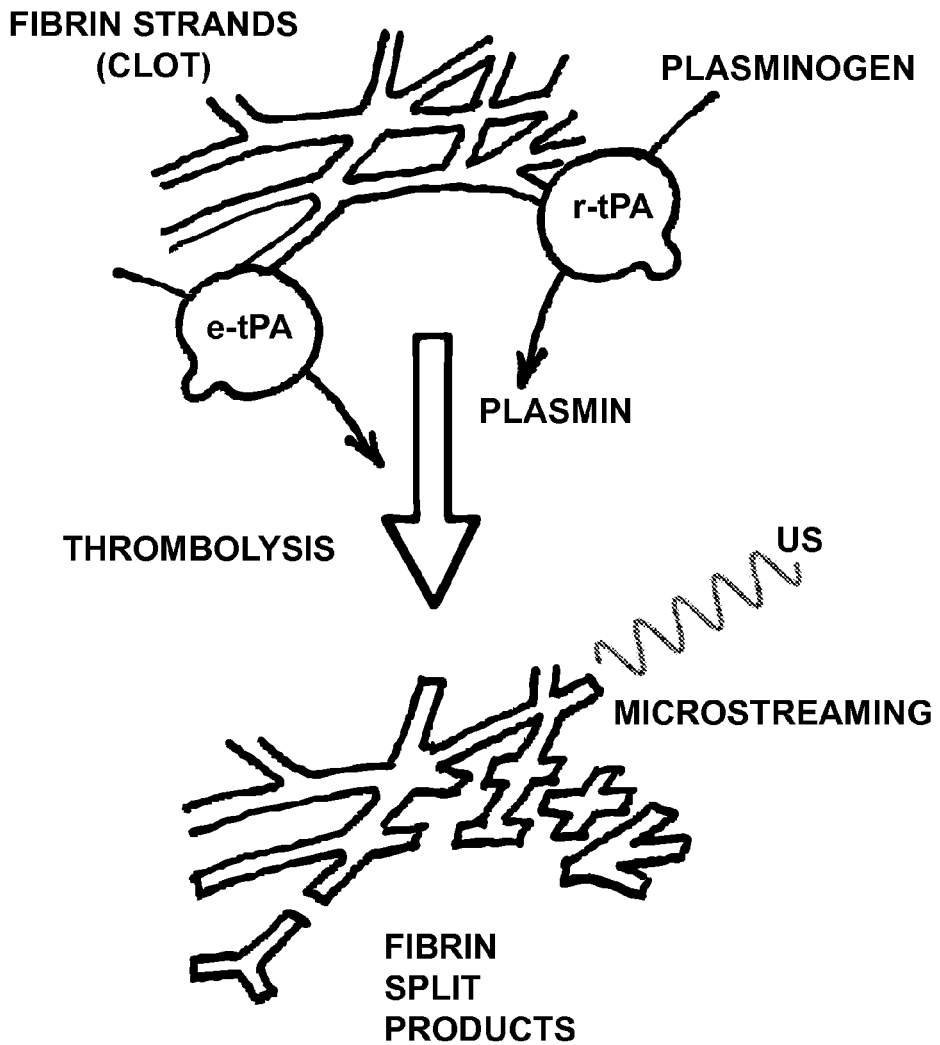

FIG. 28A depicts fibrinolysis with tPA and ultrasound. FIG. 28B tabulates prior art clinical results in achieving recanalization and the associated intracranial hemolysis (ICH) per Alexandrov (2004 NEJM 535:2170-78).

FIG. 29A depicts fibrinolysis with tPA, ultrasound and microbubbles. FIG. 29B tabulates prior art clinical results in achieving recanalization and the associated intracranial hemolysis per Molina (2005 Stroke 37:425-29).

Figure 30:
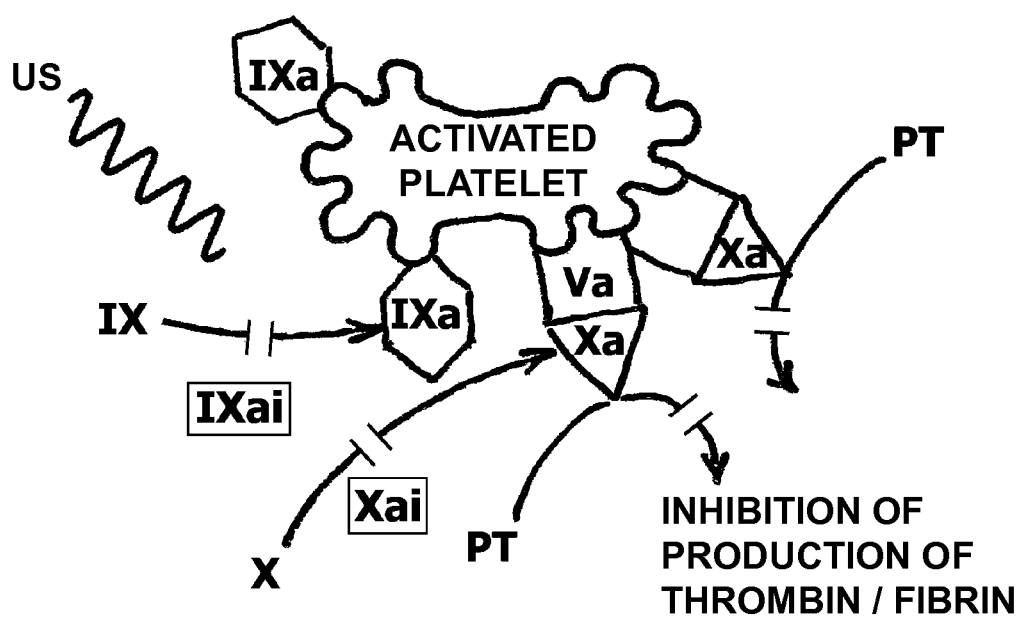

FIG. 30 depicts examples of alternate therapeutic interventions (||) to block or reverse thrombosis that are accelerated or enabled by ultrasound.

Figure 31A:
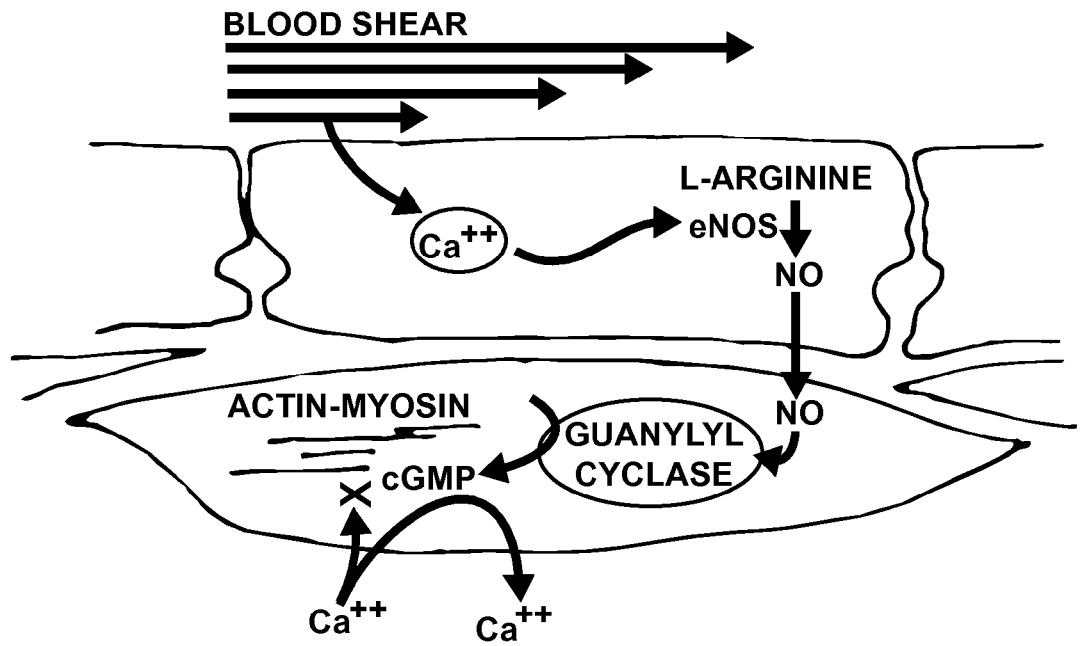
Figure 31B:
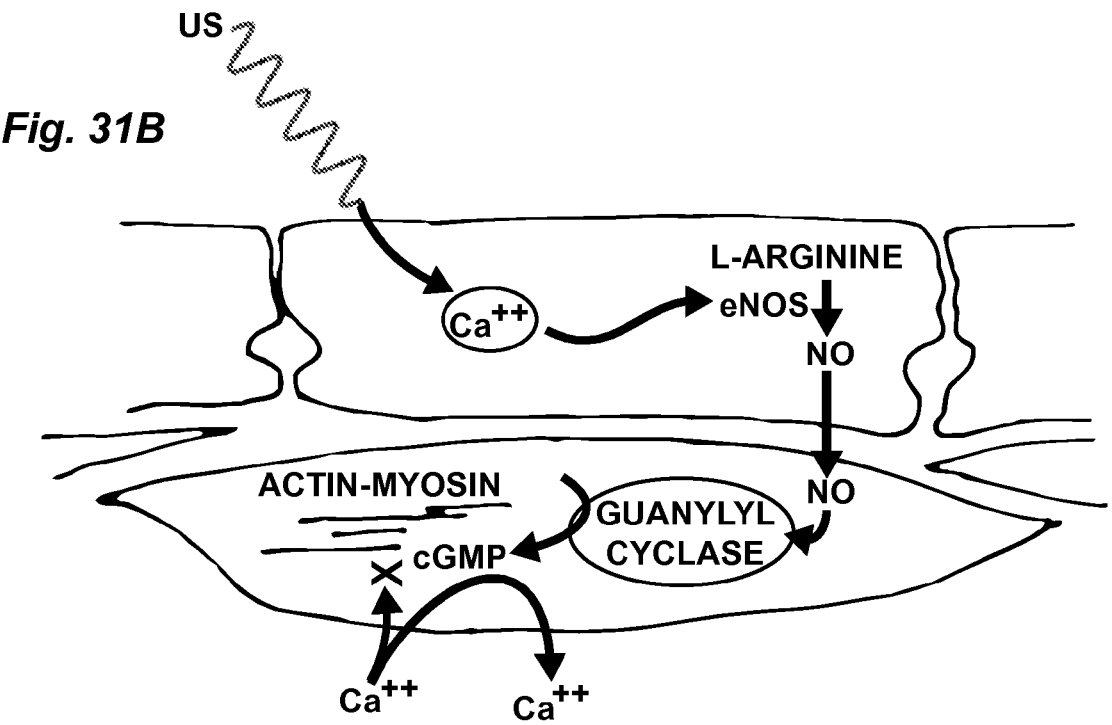

FIGS. 31A and 31B depict a model for vascular vasodilation with release of endogenous nitric oxide, where blood shear (FIG. 31A) is replaced by ultrasound (FIG. 31B).

NOTATION AND NOMENCLATURE

Certain terms throughout the following description and claims are used to refer to particular features, steps or components. As one skilled in the art will appreciate, different persons may refer to the same feature, step or component by different names. This document does not intend to distinguish between components, steps or features that differ in name but not in function or action. The drawing figures are not necessarily to scale. Certain features or components herein may be shown in somewhat schematic form and some details of conventional elements may not be shown in the interest of clarity and conciseness.

Certain meanings are defined here as intended by the inventors, i.e. they are intrinsic meanings Other words and phrases used here take their meaning as consistent with usage as would be apparent to one skilled in the relevant arts.

Acoustic Pulse—a series of sinusoidal ultrasonic pressure waves (209) forming a pulse (210), the pulse having a frequency and a pulse duration, where downfield acoustic pressure is seen to rise to a plateau as the number of pressure waves approaches fifteen.

Pulse Train—a series of pulses of emitted ultrasound, also termed an "acoustic nudge", each pulse train (211) having an ultrasonic frequency, a pulse number or count, a pulse duration, a pulse repetition frequency (PRF) and a beam centerline vector.

Acoustic "Metapulse"—a series of pulse trains of emitted ultrasound, also termed a "acoustic super-nudge". In one embodiment the pulse trains of the metapulse (212, 214, 216, 218) may be directed from spatially distributed ultrasound transducers of a plurality of transducer arrays. A "metapulse" is composed of multiple "nudges," each nudge a train of pulses, each pulse a burst of waves, and is cyclically repeated in an insonation regimen. Each "metapulse" has a metapulse cycle repetition frequency (MCRF).

Pulse repetition frequency (PRF)—for a pulsed waveform, is the number of pulses generated per second in a pulse train, typically cited as Hz or KHz.

Metapulse cycle repetition frequency (MCRF)—the frequency at which complete pulse cycles are emitted from a headset, each headset having a plurality of transducers, each firing independently and in isolation in a predetermined sequence, typically given in units of Hz.

Pulse Duration (PD)—the time of duration of a pulse, also termed the pulse width, and may be expressed in units of time or as a number of cycles at a frequency.

Pulse Interval (PI)—the time between consecutive pulses, which is commonly estimated as the inverse of the pulse repetition frequency.

Duty Cycle—in pulsed ultrasound, refers to the ratio of pulse duration to pulse interval (DC=PD/PI).

Waveform—the graphical characterization of an acoustic wave, showing time on an x-axis and pressure, amplitude or intensity on a y-axis. As used herein, also refers to a more complex pattern in which ultrasonic waves emitted by a plurality of arrays, each array having a plurality of transducers, are temporally and spatially modulated.

Peak Rarefaction Pressure ($P_r$)—The peak rarefaction pressure $P_r$ is the absolute value $|P_r|$ of the half amplitude of a sound pressure wave passing through tissue. Compression is the increase in pressure and rarefaction is the reduction in pressure of the medium during the acoustic wave cycle. Peak rarefaction pressure may be derated for losses to scattering and absorption when travelling through homogeneous and inhomogeneous matter. Peak rarefaction pressure for air-backed transducers may deviate slightly from nominal due to the effect of ringdown.

Mechanical Index (MI)—The mechanical index is an indicator of the likelihood of non-thermal bioeffects (such as cavitation). The mechanical index is defined as the peak rarefactional pressure (derated peak pressure at negative amplitude) divided by the square root of the ultrasound frequency.

$$MI = P_{r,0.3}/\sqrt{f}$$

As the mechanical index increases, the likelihood of bioeffects within tissue increases.

Regulatory limits generally allow a mechanical index of up to 1.9 to be used for therapeutic applications except ophthalmic (where the accepted maximum is 0.23). At low acoustic power, the acoustic response is generally linear.

In applications where microbubbles are present, acoustic pressure may be used to modulate the output signature of US contrast agents and to incite different microbubble responses. At a low MI (less than 0.2), microbubbles undergo oscillation with compression and rarefaction that are equal in amplitude and no special contrast enhanced signal is created. Microbubbles act as strong scattering objects due to the difference in impedance between air and liquid, and the acoustic response is optimized at the resonant frequency of a microbubble. At higher acoustic power (MI between 0.2-0.5) nonlinear oscillation occurs preferentially with the bubbles undergoing rarefaction that is greater than compression. Ultrasound waves are created at harmonics of the delivered frequency. The harmonic response frequencies are different from that of the incident wave (fundamental frequency) with subharmonics (half of the fundamental), harmonics (including the second harmonic response at twice the fundamental frequency), and ultra-harmonics obtained at 1.5 or 2.5 times the fundamental frequency. These contrast enhanced ultrasound signals are microbubble-specific. At high acoustic power (MI greater than 0.5), microbubble destruction begins with emission of high intensity transient signals very rich in nonlinear components. Intermittent imaging becomes needed to allow the capillaries to be refilled with fresh microbubbles. Microbubble destruction occurs to some degree at all mechanical indices. A mechanical index from 0.8 to 1.9 creates high microbubble destruction. The output signal is unique to the contrast agent.

Intensity, spatial-peak temporal average ($I_{spta}$)—The value of the temporal average intensity at the point in the acoustic field where the intensity is at a maximum; measured in Watts/cm$^2$. $I_{spta.0}$ is a complex function of the voltage applied to the transducer and the piezoelectric, magnetostrictive, or electrocapacitive effect on the transducer.

$$I_{spta.0} = (\rho c^{-1}) * \int_0^{PD} \frac{P_r^2(t)}{dt}$$

$$I_{spta.0} = (\rho c^{-1}) * \int_0^{PD} P_r^2(t)/dt$$

Thermal Index (TI)—is a calculated estimate of temperature increase with tissue absorption of ultrasound and is determined by the ratio of the total acoustic power to the acoustic power required to raise the tissue temperature by 1° C. Some devices further subcategorize the TI according to the insonated tissue: soft tissue thermal index (TIS) for soft homogeneous tissues, cranial bone thermal index (TIC) for bone at or near the surface, and bone thermal index (TIB) for bone after the beam has passed through soft tissue. More generally, the temperature of insonated tissue increases with increasing intensity and with increasing frequency.

Non-focused transducer—refers to a transducer producing a divergent beam exiting the near field, where beam diameter progressively increases with depth in the far field. The near field length and hence the natural divergence of an ultrasonic beam are determined by aperture (equal to element diameter in the case of conventional monolithic transducers) and wavelength (wave velocity divided by frequency). For an unfocused transducer, the near field length, beam spread angle, and beam diameter can be calculated as follows:

$$L = D^2 f_c / 4c$$

where,
L is near field length,
D is element diameter or aperture,
$f_c$ is the frequency, and
c is the sound velocity in the medium.

Focused transducer—Within its near field, a transducer can be focused to create a beam that converges rather than diverges. Narrowing the beam diameter to a focal point increases sound energy per unit area within the focal zone and thus has found use in therapeutic applications (Cintas 2002). Conventional piezoelectric slab transducers usually do this with a refractive acoustic lens, while phased arrays do it electronically by means of phased pulsing and the resulting beam shaping effects.

Phased Array—a composite transducer having physically contiguous sub-elements where the sub-elements are electronically controlled for independent actuation.

Automaton—refers to an apparatus or device that autonomously performs certain actions, here patterned emissions of ultrasound from a headset worn over the head, by executing preset controls or encoded instructions without human intervention, and is thus operable, after activation, in "hands-free" mode such that operator-independent insonation is performed. The device may include an electronic control circuit equipped with a microcontroller, non-volatile memory for storing instructions and reference data, clock functionality for generating ultrasonic pulses and for actuating individual transducers according to a timed sequence, and afferent and efferent connections for receiving and transmitting commands and signals to and from peripheral devices such as transducers, acoustic coupling circuitry, and an associated receiving and wireless transmission circuit, for example. The apparatus as defined herein is non-invasive and lacks a surgical component in a method of use. In a preferred embodiment, the automaton is operated according one or more regimens and look-up tables that define the ultrasonic waveforms of a metapulse cycle and the amplitudes to be generated by the device.

Stereotactic positioning—A method in neuroscience for locating points within the brain using an external frame of reference; as used here, relating to positioning with respect to a tissue, esp. in the brain. We have established a preferred frame of reference for sonothrombolysis using external osteology, where the cranial frame of reference is based on one or more craniological landmarks of the head selected from nasion, Lt otobasion superius, Rt otobasion superius, tragion, mandibular condyle, zygomatic arch, prosthion, and/or occipital protuberance, and most preferably a triangular frame of reference based on the nasion, and the Rt and Lt otobasion superiora landmarks, which establish the relative positions of the temporal and sub-occipital acoustic windows, the sphenoid "shelf" formed by the greater and lesser wings of the sphenoid bone, the anterior and posterior clinoid processes, dorsum sellae, and the Circle of Willis with cerebral arterial circle, bifurcations of the internal carotid artery conjoining the anterior, middle and posterior cerebral arteries, and junctures of the basilar artery with the communicating cerebral arteries and the vertebral arteries. This frame of reference has proved more robust in practice than Broca's reference plane, also termed the "neuro-ocular plane" (NOP) as used by radiologists, although the two reference planes are relatively closely aligned, and is much preferred over the Frankfurt-Virchow plane, which lies oblique to and below the target anatomy. While the NOP, which follows the orbital tracts, is slightly below and parallel to the Circle of Willis, its use requires a measurement of 3.3 cm above the tragion, and hence is not readily practiced by unskilled persons. In contrast, the reference plane established herein is readily practiced without instruction using a first embodiment of the headset of the invention. Heights above and below the foundational reference plane used here are preset by the headset geometry and transducers are angled accordingly so as to insonate a cerebrovascular target or targets of interest. Emplacing the headset is almost as simple as donning a pair of eyeglasses.

Streaming—an effect of ultrasound on the behavior of insonated liquids. Mechanisms whereby low-intensity ultrasound increases enzymatic fibrinolysis include acoustic streaming at clot/blood flow boundary and reversible changes in fibrin structure, which both result in increased plasminogen activator binding to fibrin and transport into the clot. Acoustic streaming associated with harmonic oscillation of microbubbles has also been termed microstreaming. Acoustic streaming and microstreaming also promotes flow of interstitial and blood fluids, as described for example by Eggleton and Fry (U.S. Pat. No. 3,961,140).

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, particular features, structures, or characteristics of the various embodiments of invention may be combined in any suitable manner in one or more embodiments.

Conventional—refers to a term or method designating that which is known and commonly understood in the technology to which this invention relates.

Unless the context requires otherwise, throughout the specification and claims which follow, the word "comprise" and variations thereof, such as, "comprises" and "comprising" are to be construed in an open, inclusive sense, that is as "including, but not limited to".

The appended claims are not to be interpreted as including means-plus-function limitations, unless such a limitation is explicitly recited in a given claim using the phrase "means for."

DETAILED DESCRIPTION

Although the following detailed description contains many specific details for the purposes of illustration, one of skill in the art will appreciate that many variations and alterations to the following details are within the scope of the invention. Accordingly, the exemplary embodiments of the invention described below are set forth without any loss of generality to, and without imposing limitations upon, the claimed invention.

Figure 1:
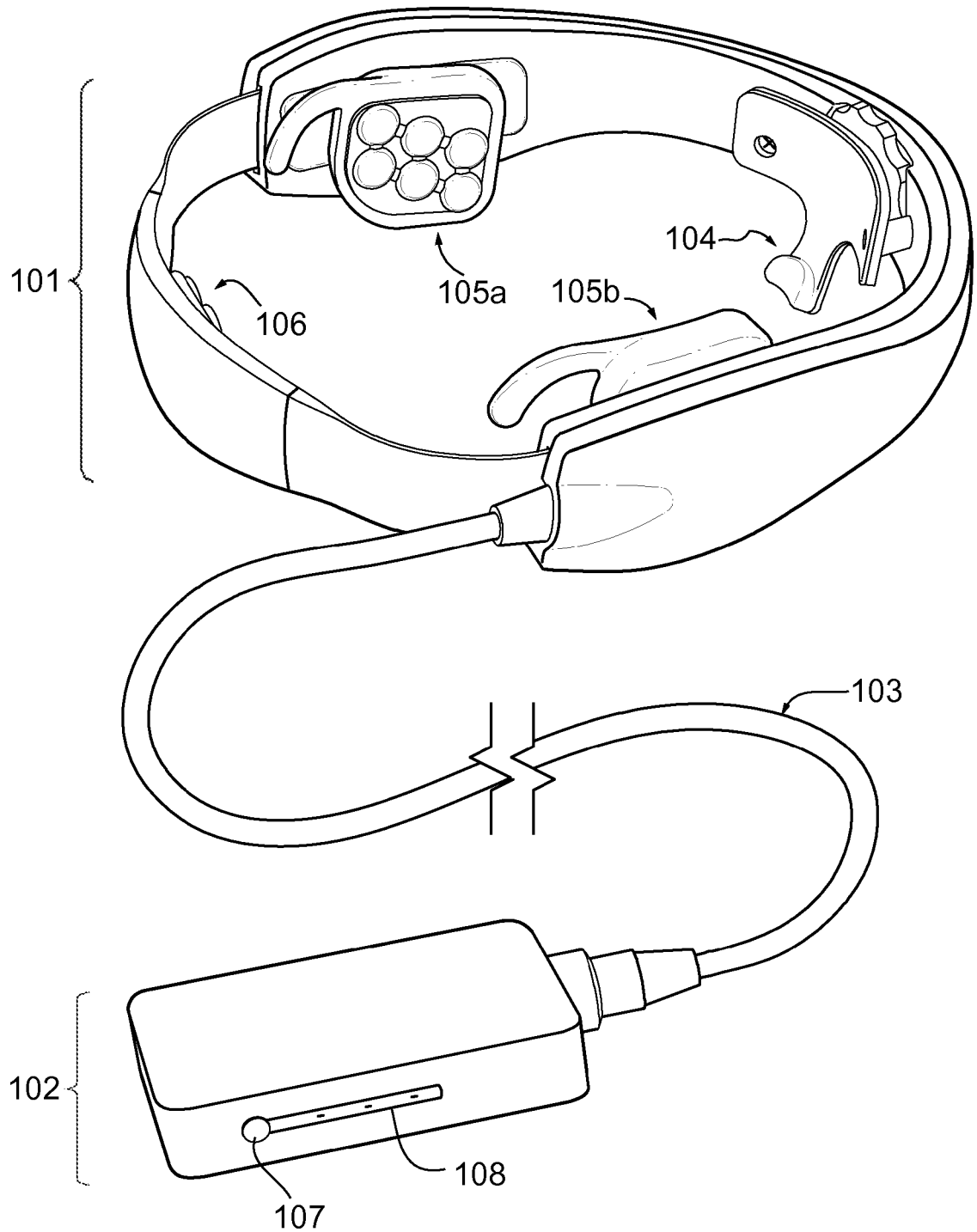
FIG. 1 is a mechanical drawing of a fully assembled device, including headset, cable or "umbilicus", and remote control with power supply unit in a pocket-sized housing.

FIG. 1 is a drawing of a fully assembled apparatus (100), including headset (101), cable or umbilicus 103, and remote control with power supply unit in a pocket-sized housing 102. The remote control is supplied with an on/off or pause actuator or button (107) and a status indicator bar (108). The headset is designed for extended periods of wear and weighs less than 500 grams; the overall apparatus weighing less than 1 kg. As configured here, three transducer arrays are mounted in the circumcranial headset and each tranducer array contains a plurality of crystals, each about 1 cm in diameter. In a first embodiment of the invention, a device having 16 transducers was built, 6 transducers each per temporal array (105a, 105b) and 4 transducers per occipital array (106). Each transducer is a piezoelectric crystal designed to operate at a particular frequency. Systems operated at 1 MHz and at 2 MHz have been built and tested. Systems having 12 or 20 transducers, and operated at one or more base or "primary" frequencies selected from a range of 500 to 3500 KHz are also contemplated, for example.

Transducers emit ultrasound in pulses, the pulses in trains of pulses, the trains of pulses modulated in time and position. Advantageously and paradoxically, this reduces insonation intensity and power draw—but increases effectiveness. In order to reproducibly orient the headset without use of an imaging study, the apparatus is fitted to selected craniological landmarks of the skull, shown here is a nasion registration brace with pad or nosepiece (104) which will be described in more detail below.

The structural shell or supporting members of the headset assembly may be constructed of plastic, the plastic a radiolucent material having a low Hounsfield density. Plastics include polycarbonate, acrylonitrile butadiene styrene (ABS), styrene-acrylonitrile, polystyrene, nylons, polyethylenes, acrylates, and so forth. For example, Bayblend (Bayer MaterialScience, Dusseldorf DE) may be used in construction of headsets of the invention, although not limited thereto. The CT translucency of various plastics has been described by Henrikson (1987, CT evaluation of plastic intraocular foreign bodies, Am J Neuroradiology 8:378-79).

Figure 2:
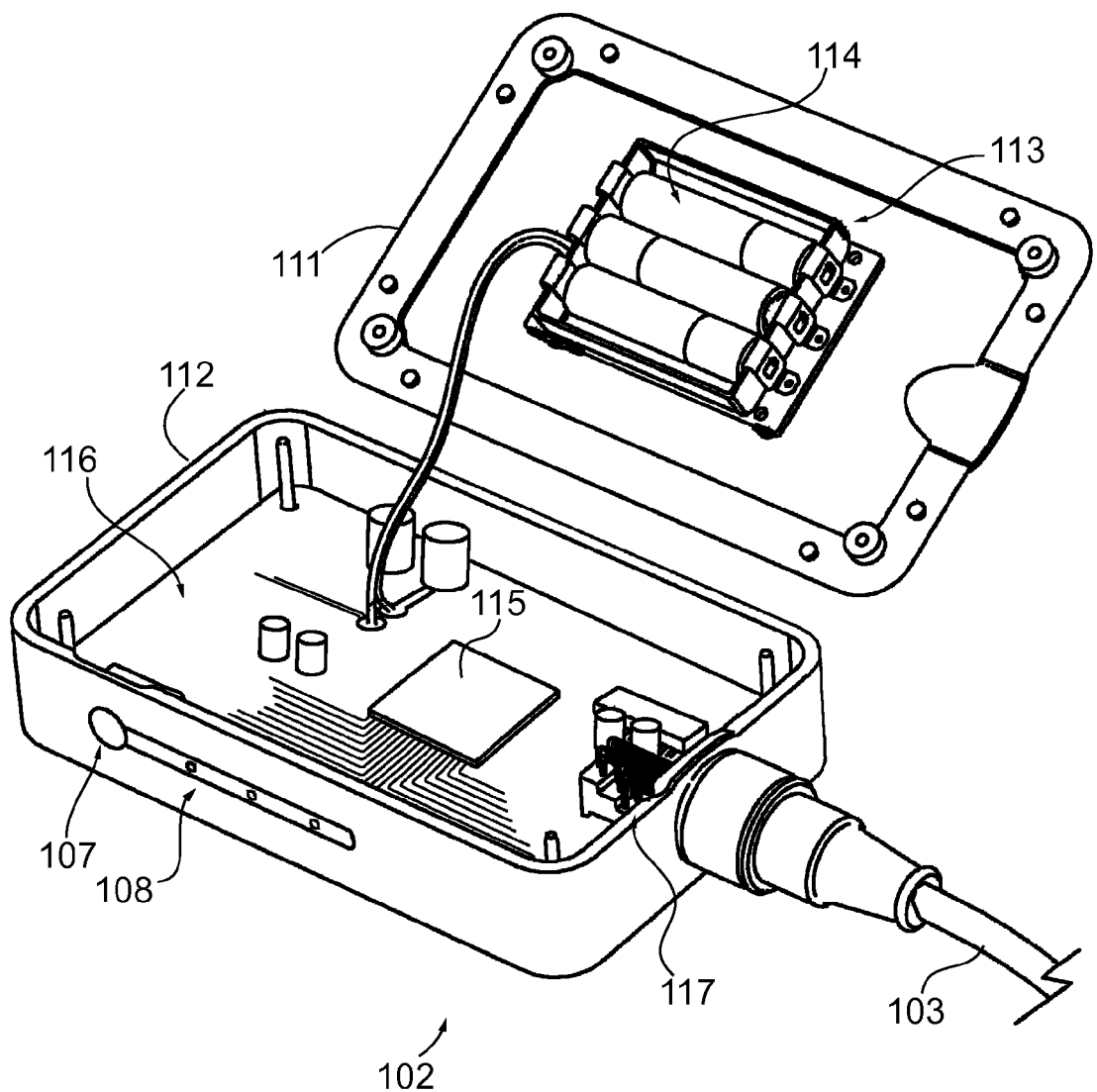
FIG. 2 is a perspective view of the contents of a remote control unit with housing, indicating generally a PCB with microcontroller and associated circuitry and a battery pack power supply; here three AAA batteries. Also shown is an on-off/pause switch.

FIG. 2 is a perspective view of the contents of the remote control unit (102) with housing case (112) and cover (111), figuratively showing a printed circuit board (116) with microcontroller (115) and generalized associated circuitry. Also shown, mounted in the cover, is a battery pack power supply (113); here three AAA batteries (114). Also shown is an on-off/pause switch (107) and at least one status indicator (108) such as an LED, or other status indicator such as a buzzer or a liquid crystal display.

The printed circuit board is supplied with leads to a junction (117) that forms a power and data bus routed through umbilicus 103 to the headset 100.

The battery pack may be selected from a number of compact batteries commercially available that can deliver about 200 mAmp-hrs, 400 mAmp-hrs if needed, without recharging for up to about 12 hours at an operating voltage of about 1.5 to about 4 VDC, most preferably about 3.5±1 VDC, but optionally about 9-12 VDC. The battery pack will thus have a capacity of 0.6 to 15 Watt-hours and preferably has a weight of less than 250 grams, more preferably less than about 100 grams, and most preferably less than about 50 grams. The battery may be generically a rechargeable battery, an insertable battery, a lithium ion battery, a lithium ion polymer battery, a lithium iron phosphate battery, a lithium-sulfur battery, a lithium-titanate battery, a nickel-zinc battery, a nickel-iron battery, a NiCd battery, a NiMH battery, an alkaline battery, a 9 V battery, a cell phone battery, or at least one AA or AAA battery, and so forth.

The battery pack is rechargeable or replaceable, and optionally where rechargeable, may include a control circuit with "fuel gauge" circuit such as is available from Benchmark (BQ2040) for use in recharging the battery pack. Cell phone batteries are typically about 3.7 V and can deliver about 1 Amp-hr or a specific power of 20 to 40 mAmp-hrs/gm or more. For example, an apparatus of the invention having a maximal power draw of 400 mAmp-hrs that is operated for 2 hrs in continuous mode and subsequently for 10 hrs in intermittent mode at 200 mAmp-hrs will require a battery pack of about 2.8 Amp-hrs capacity. An apparatus having a maximal power draw of 200 mAmp-hrs would require only 400 mAmp-hrs for operation over a 2 hr cycle, and hence could be operated with three AAA batteries in series supplying about 4 volts. New batteries could be installed if needed and the total weight of the battery pack is 50 gm or less, by way of example.

Figure 3A:
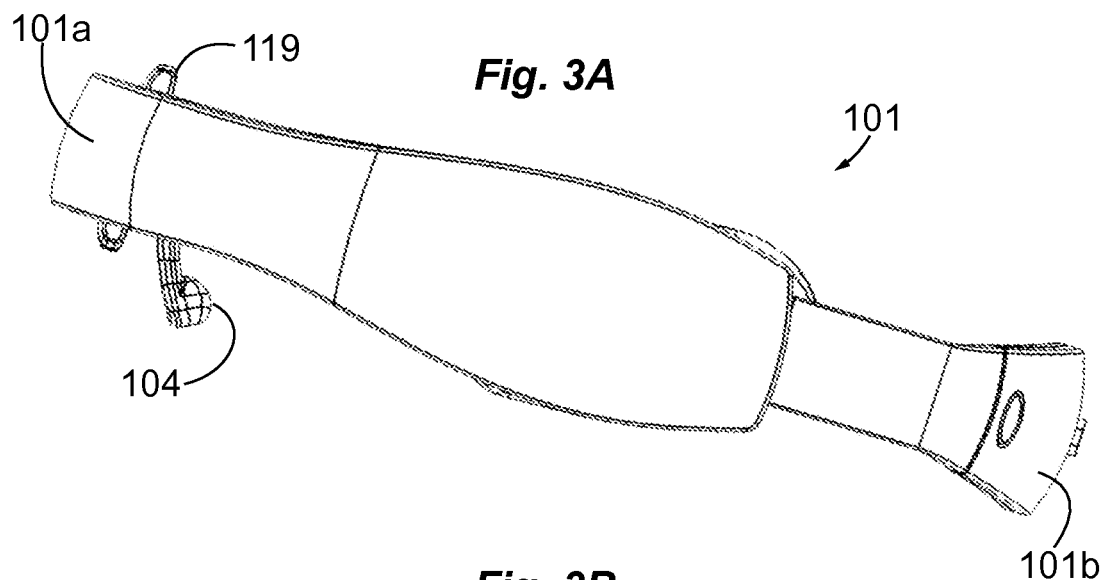
FIGS. 3A and 3B depict a mechanical headset in side and plan views.
Figure 3B:
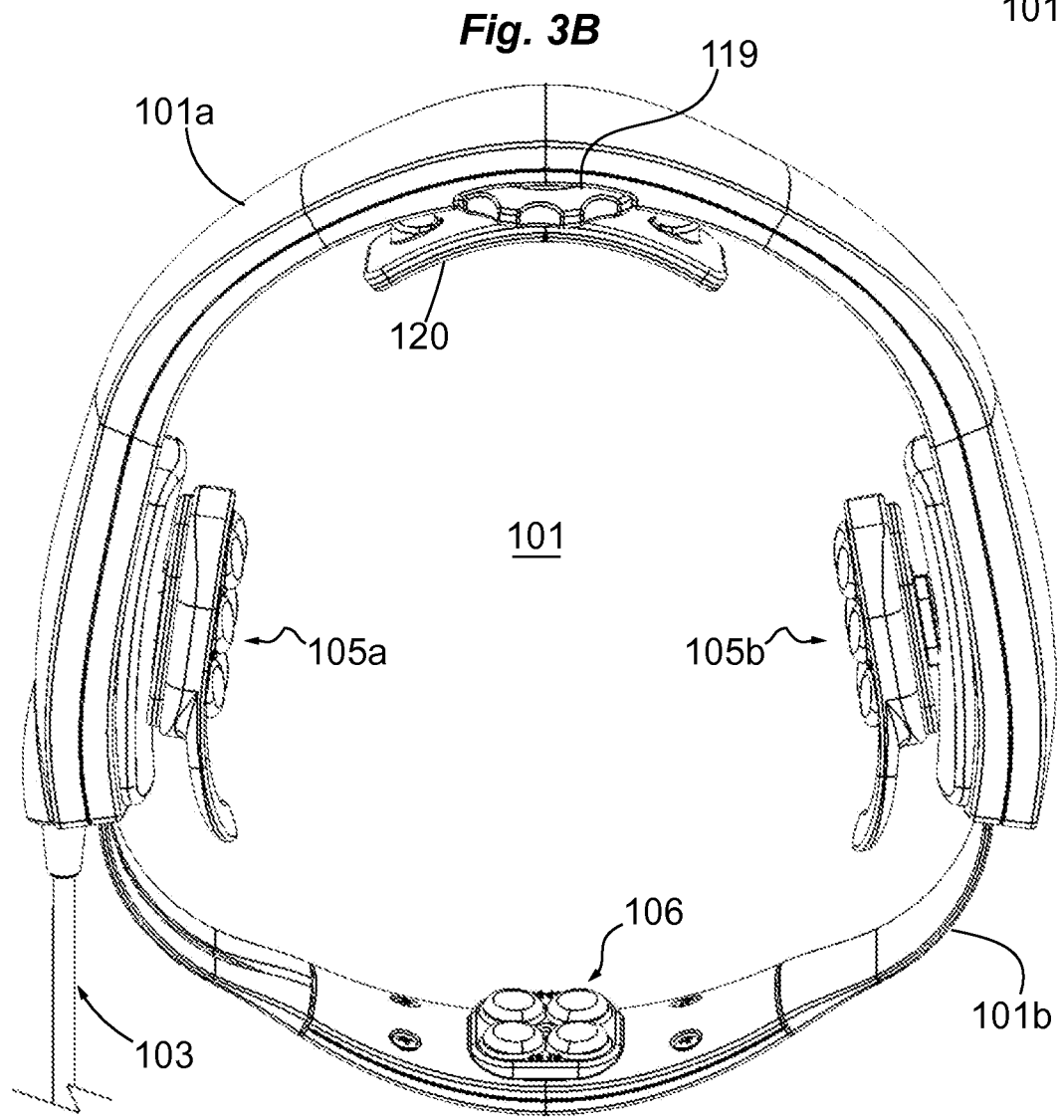

FIGS. 3A and 3B depict a headset assembly (101) from side and superior views. The inventive devices are built with multiple transducers (here shown clustered in two paired contralateral temporal transducer arrays 105a, 105b and a posterior occipital transducer array 106, each transducer array having a plurality of individually powered piezoelectric crystals) and a stereotactic registration or positioning system having nose and ear registration brackets for aligning the transducers with the corresponding acoustic windows and cerebral vasculature. External landmarks are used to position the arrays with respect to internal vascular targets in the brain, solving a problem that would otherwise potentially delay initiation of insonation. While the transducers selected for this device are non-focussed, the beams have a center axis and a width of maximal acoustic pressure, so for both efficacy and safety reasons, orientation of the beams stereotactically with respect to brain anatomy is preferred. At least three registration surfaces are used in conjunction for stereotactically positioning the headset assembly on a head of a wearer. A first registration bracket (120) is shown mounted anteriorly inside the headframe.

Many strokes are found to be strokes of the cerebral arteries associated with the circle of Willis. Thus locating the Circle of Willis with respect to external craniological landmarks proved a useful solution to the question of orienting the transducers without need for reliance on imaging studies by a skilled sonographer or radiologist.

The headset of the figure is constructed of an arcuate anterior headframe member (101a) for fitting to the front of the head and an arcuate, pliant, posterior headband member (101b) that is adjustable by means of a tightening mechanism or knob (119) within the body of the anterior headframe member, into which opposite ends of the posterior headband insert. Tightening is achieved by tensioning the posterior headband member and does not affect placement of the anterior headframe member with registration brackets, thus ensuring that the stereotactic alignment with respect to the cerebral vasculature is not disturbed.

Figure 4:
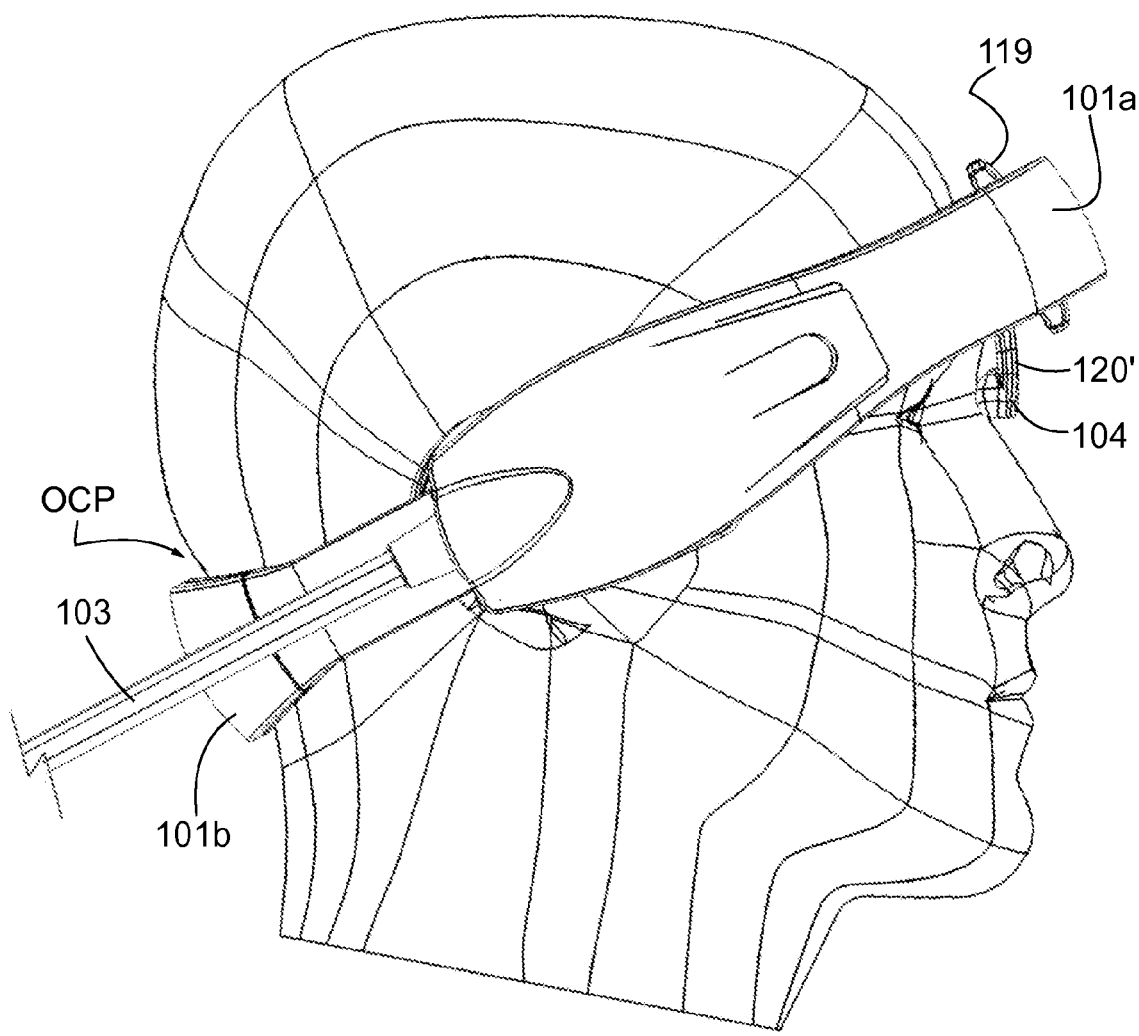
FIG. 4 is a view of the headset on a user.

FIG. 4 is a view of the headset on a user. The cable (103) is optionally detachable so that the headset is optionally disposable. Alternatively, the cable may be integrated into the headset and be detachable from the housing for the power supply and electronic controller.

The nasion registration brace (120') is part of the nasion registration bracket (120) and supports a pad (104) adapted to be fitted against the nasion on the bridge of the nose of the user. As will be shown, this is one of three registration elements used to orient the headframe with respect to transcranial acoustic windows and target vasculature.

Figure 5A:
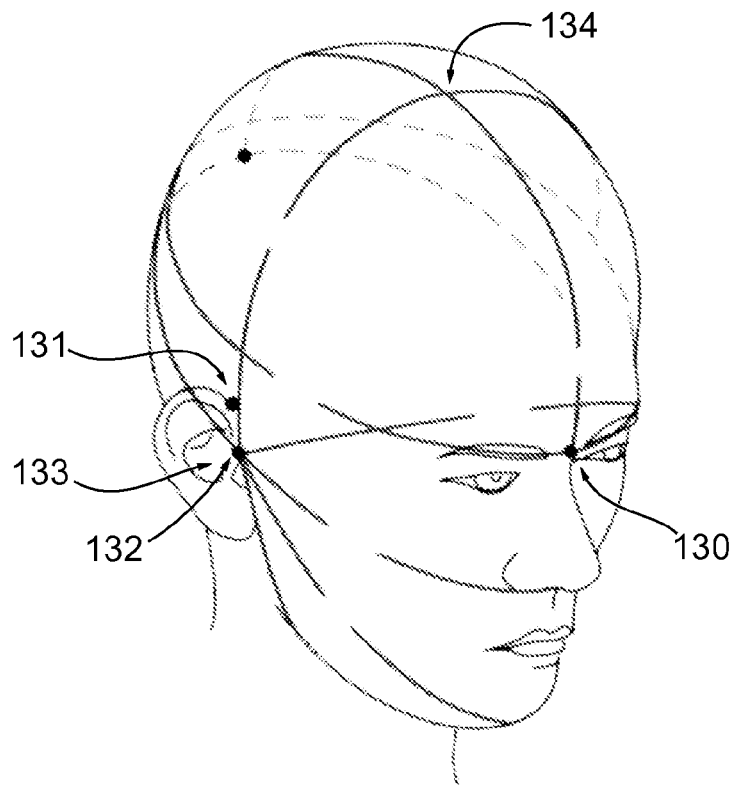
FIG. 5A is a rendering of a head with selected craniological landmarks of the skull that have a spatial relationship with the sphenoid shelf (and anterior clinoid processes) on which sits the Circle of Willis. Three such landmarks are used to stereotactically align the arrays with acoustic windows and cerebral vasculature; inset
Figure 5B:
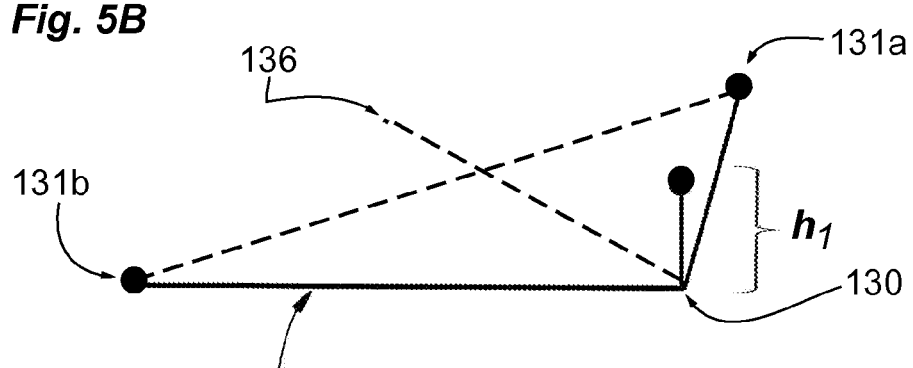
FIG. 5B illustrates the triangular foundational plane (135) of registration landmarks used for orienting the headset so that the transducer arrays are positioned and aligned in registration with the cerebral vasculature.

FIG. 5A is a rendering of a head with characteristic external craniological landmarks of the head that have a spatial relationship with the sphenoid shelf (marked by the anterior clinoid processes, see FIG. 6A) on which sits the major aspect of the Circle of Willis which is at the center of the cerebrovascular tree or nexus. Three such landmarks are used to stereotactically align the arrays with acoustic windows and cerebral vasculature; FIG. 5B illustrates a triangular plane of registration landmarks which used for orienting the headset so that the transducer arrays are positioned and aligned in registration with the cerebral vasculature. The triangle is an Isosceles triangle and has a base and is bisected by a midline that runs anteriorposteriorly through the cranial vault generally tangentially to the sphenoid shelf and parallel to and slightly above the optical tract. The reference plane described by the triangle is an external guide to the location of the cerebral vasculature most susceptible to stroke. The triangle is bisected by a midline (136) which defines the cerebral hemispheres.

Landmarks for positioning a headset may be selected from nasion (130), otobasion superior, OBS, 131), tragion (132), auditory meatus (auricular point, 133), mandibular condyle, zygomatic arch, prosthion, bregma (134), or occipital prominence (OCP). At least three are selected. The mechanical brackets are configured with surfaces for engaging the selected landmarks of the head and stereotactically orienting the transducer arrays with respect to acoustic windows onto the cerebral arterial tree of the brain.

Figure 5C:
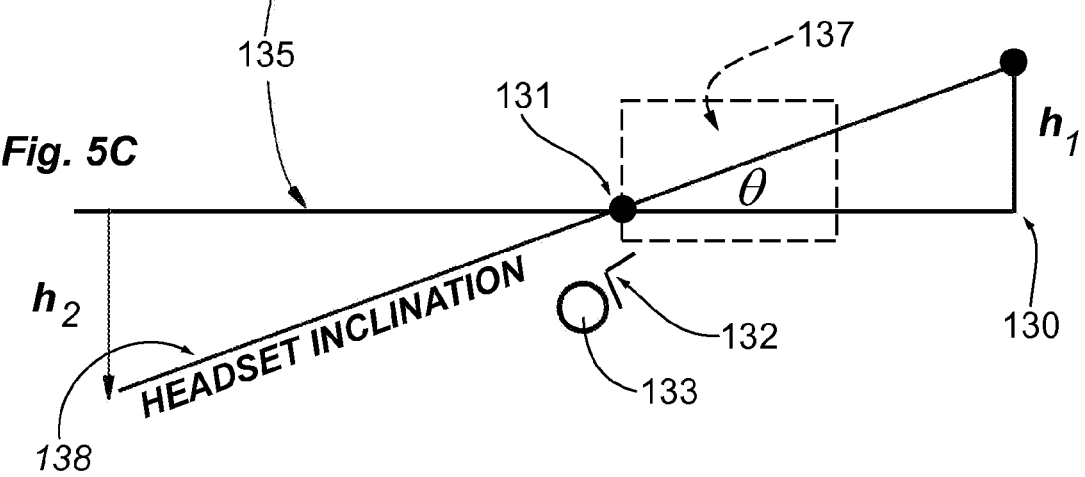
FIG. 5C illustrates a fixed inclination of the headset relative to the foundational registration plane.

In a preferred embodiment, the nasion, and left and right OBS are chosen as shown. The Alleman Plane (135) is defined by an Isosceles triangle having a base formed by a line connecting the right and left otobasion superius (OBS, 131a, 131b) and lines joining with an apex of the triangle at the nasion (130). This triangle rests on the Alleman Plane. FIG. 5C shows that the headset may be inclined from the Alleman Plane by offsetting the anterior headframe member by a height "$h_1$" above the nasion. Height $h_1$ is generally taken as about 2 centimeters. In this way the anterior aspect of the headset clears the brow of the wearer; literature citations indicate that the adult height of the glabella is 0.7 to 1.6 centimeters above the nasion. The posterior headband member is seated below the occipital protuberance by a height $h_2$. When so inclined, the headset continues to rest on the OBS registration landmarks but is now tilted as shown ("headset inclination", 138). The headset is inclined from the reference plane by height $h_1$, the inclination angle "theta" is generally taken as about or approaching 12 degrees. The temporal transducer arrays may then be slideably positioned on the headframe over the temporal acoustic window (137). Individual temporal transducers are angled superiorly and anteriorly (see FIG. 7D) to target various aspects of the cerebral arterial tree. Approximate locations of the tragion (132) and the auditory meatus (with center auricular point, 133) are shown for reference.

FIG. 6A is an exposed view of the cranium (140) showing the cranial vault (141) and bones forming the sphenoid shelf (143) and the general position of the major cerebral arteries (142, 144). FIGS. 6B and 6C are views of the major cerebral arteries (superior and lateral views respectively) and the Circle of Willis (144), herein also termed the cerebral arterial nexus, which can be seen resting partially in FIG. 6A on the shelf or ledge formed by the greater and lesser wings of the sphenoid bone, an anatomical feature termed herein the "sphenoid shelf" (143), which forms the base of the anterior fossae overlying the orbital tracts and is generally co-localized with the Alleman Plane.

Shown are the anterior cerebral artery (ACA), middle cerebral artery (MCA), posterior cerebral artery (PCA), internal carotid artery (ICA), basilar artery (BAS) and vertebral arteries (VER) and their connections to the Circle of Willis (144).

FIG. 7A shows an elevation view of the nasion registration bracket (120) for aligning the transducer arrays with the nasion and sphenoid shelf (in conjuction with the OBS registration brackets described below). The nasion registration brace (120', vertical element with height $h_1$) includes a beveled wedge or nosepiece (104) for positioning against the nasion under the glabella and is rigidly attached to the anterior headframe member (101a) of the headset assembly. The headframe also contains a tightening knob (119) that operates by a ratcheting mechanism on the right and left ends of the posterior headband member (101b, see FIG. 3B).

Also shown is an end view of the two ends of the anterior headframe member, detailing the structure of an adjustment slider track (152) for slideably repositioning the temporal transducer array assemblies (FIGS. 7B-7D). Also shown is receiving orifice for the cable junction (151) and the insertion slot (150) for insertion of the posterior headband assembly.

A temporal transducer array subassembly (105b) is now described in more detail. FIGS. 7B and C are external views showing the lateral OBS registration brackets (or earpiece, 154) with surface adapted for aligning the temporal transducer arrays with the otobasion superius (OBS) and sphenoid shelf. Also shown is a slider foot (153) that inserts into the slider track (152) of the headframe and permits fitted positioning the transducer arrays anterior to the ear of the wearer so that the transducer array engages temporal acoustic window 137. FIG. 7D shows a cross-section through a piezoelectric crystal of the temporal array and illustrates the slider that mounts in the adjustment slider track shown in FIG. 7A.

It can be seen that the Rt temporal transducer array and OBS registration bracket with registration surface for engaging the Rt otobasion superius are rigidly affixed to a Rt temporal subassembly, said Rt temporal subassembly being slideably mounted to the headset assembly on a track (152, right) for anterioposterior adjustment in relation to the midline; correspondingly the Lt temporal transducer array and the Lt OBS registration bracket with registration surface for engaging the Lt otobasion superius are rigidly affixed to a Lt temporal subassembly, the Lt temporal subassembly being slideably mounted to the headset assembly on a track (152, left) for anterioposterior adjustment in relation to the midline and base of the triangle.

As can be seen in FIG. 7D, the transducers are optionally enclosed in a housing (marked here on lower aspect 156a) with baseplate 156b shown here in cross-section. Transducers (155a) forming a hexapartite array are show. Transducers 155b and 155c are shown in cross-section. A profile view of the slider foot 153 is also shown here. The housing includes a thin overlayer 157 as a coupling layer for more efficiently coupling acoustic output to the skull. This overlayer may be a polyurethane, a polyethylene, a silicon, a rubber, and so forth, having a relatively soft and compliant modulus intermediate between the hardness of the transducer and the hardness of the skull or couplant gel. Other means for improving coupling are described by Horzewski and others and are incorporated by reference here. Couplant gels are well known in the art.

When properly positioned on the wearer, the lower aspect of the temporal transducer arrays 156a are generally aligned with and above the upper border of the zygomatic arch so that the transducers 155 are firmly engaged and acoustically coupled with gel against the temporal acoustic window.

In one embodiment of the invention, the several transducer assemblies (105a, 105b, 106) are configured to be detachable so as to be saleable as a kit, where the kit consists of a transducer array in a disposable module prefitted with a "ready-to-use" gel couplant pad in a sealed packet. A mounting receptacle is provided which is pre-attached to the anterior headframe assembly 101a and the transducer arrays themselves are removed from their sealed packets and snapped into place in the corresponding mated receptacle on the headframe prior to use. The transducer modules are provided with wiring pins that are plugged into a female socket in the mounting receptacle and the apparatus performs a functional self-check using integrated watchdog circuitry before beginning insonation. In this way, the required gel couplant is provided with the apparatus. Optionally, the apparatus may also perform a self-check to verify acoustic coupling, such as by use of the phase comparator circuitry described later in this description, prior to initiation of cyclical metapulse emission.

FIG. 8A depicts a temporal transducer array (105) as it interfaces with the temporal acoustic window on the ispilateral side of the skull, as seen from a superimposed view of the transducer arrays and central cerebral vasculature (visible are BAS and the Circle of Willis, 144). Anchoring of the occipital transducer array (106) under the OCP is also shown in this view. It can be seen that the nasion registration brace or riser (120') with nosepiece (104) and posterior strap (101b) under the OCP stabilize the anatomical position of the headset when tightenened by tensioning knob 119 during use. In this position, the head may be bent forward to open the occipital acoustic window without loss of stereotactic positioning of the Rt and Lt temporal transducer arrays.

FIG. 8B is a "see-through" perspective view showing figuratively how the (non-focused) ultrasound beams of the temporal transducer array are directed at the internal anatomy of the cerebral vasculature. The cone is shown for purposes of representation of the −6 dB radial boundary of each beam and is not intended as a literal depiction of an acoustic wavefront emanating from a transducer. The temporal acoustic window is chosen as one of the thinner of the boney plates surrounding the brain. Beams (160a, 160b) entering the temporal acoustic window from transducers 155 of the Rt temporal array (105b) are shown to continue (161) through the major nexii of the cerebral vasculature. Marked are the MCA, ACA, ICA and Circle of Willis (144). It can be seen that by alternating emissions from the Rt and Lt temporal arrays, both hemispheres of the brain receive emissions equally in the absence of an imaging study to suggest further localization of the beams.

FIG. 9A depicts a superior view of the headset assembly (101) as would be positioned on a skull, showing temporal (cones, 160) and occipital ultrasound beams (cones, 162) figuratively targeted at a central cerebral vasculature. It can be seen that the −6 dB radial boundary effectively targets the vasculature of interest in two directions (161, 163). This stereotactical aiming of the incident beams aids in the effect of the emissions. In this embodiment, the occipital transducer array 106 contains four transducers 166.

FIG. 9B is a "see through" lateral view showing how the ultrasound beams of the occipital transducer array 106 are directed at the internal cerebral vasculature. Beams are represented by −6 dB cones (162a, 162b). When properly angled and positioned using the stereotactic positioning aides of the invention, transducers in the occipital array can be directed at the basilar and vertebral artery as well as the junction of the internal carotids and anterior/posterior communicating arteries of the Circle of Willis.

FIG. 10A is a table describing the results of a Phase II human trial with a prior art device (Daffertshoffer 2005 Transcranial low-frequency ultrasound-mediated thrombolysis in brain ischemia, Stroke 36:1441-46). As would be understood by one skilled in the art, of 13 of 14 subjects treated with a combination of r-tPA and focused low frequency ultrasound (300 KHz), all but one converted to intracranial hemorrhage as a sequel to the treatment. This reference also reports that insonation through the skull at 2-4 MHz is associated with such a remarkable loss of energy that no clot degradation could be demonstrated experimentally; thus it would appear that lower frequencies are highly dangerous and higher frequencies are ineffective, in short describing a substantial and poorly understood technological barrier that was not overcome in the prior art.

FIG. 10B plots the relationship (200) between peak rarefaction pressure (KPa) and ICH conversion (%) as we have determined by retrospective analysis of data from multiple clinical trials. While the results of Daffertshoffer (FIG. 10A) could be interpreted as related to the selection of frequency, our analysis demonstrates a stronger correlation with maximal in vivo peak rarefaction pressure ($P_r$), and a threshold at about 300 KPa where increasing amplitude of ultrasound above this limit in a target tissue was associated with an increase in ICH over baseline with r-tPA alone (201) and where ultrasonic amplitudes at or below this threshold were not associated with increased ICH. It can be seen that 300 KPa represents a threshold where increases in insonation amplitude are associated with increases in ICH conversion, a technological problem not previously recognized. Based on this analysis, a device configured not to exceed the $P_r \leq 300$ KPa threshold in target tissues was built. Coincidentally, this configuration operates for longer periods of time at lower power, and is found here to improve therapeutic outcomes, a technological advance in the art.

FIG. 11A is a plot of peak rarefaction pressure versus depth (203) as a function of cranial bone thickness (range of dotted curves). Also shown is a representation of centerline acoustic pressure of an unattenuated ultrasound beam in water (202). It can be seen that significant ultrasound energy is lost in transit across the skull bone, for example at a temporal acoustic window, and that individual variation exists such that no single driving voltage can be selected without encountering patient-to-patient variation in realized $P_r$ values at depth. In short, thick skull and thin skull individuals receive significantly different ultrasound exposure at constant voltage.

Insonation can also vary because of transducer-to-transducer variation in manufacture. Thus a device that is able to correct for manufacturing variability offers a significant improvement in treatment consistency. To better understand the mechanics of attenuation so as to be able to factor out and solve for the contribution of boney layer attenuation, it is useful to construct a full physical model of attenuation along the beam path.

FIG. 11B is a plot of attenuation (A) as a function of frequency for temporal bone and is based on a compilation of studies from the literature. The data are fit to a parabolic function. By selecting a frequency, an attenuation coefficient at that frequency can be solved.

In FIGS. 12A and 12B, the outlines of a calculation of attenuation are shown pictographically. The renderings represent physical models for analysis of an attenuation profile as a function of depth for a transducer seated at a temporal acoustic window (FIG. 12A) and for a transducer apposing an occipital acoustic window (FIG. 12B), where a layer of fatty generally covers the muscles the spine that overlie the atlas and foramen magnum.

Considering first the temporal acoustic window model, it can be seen that attenuation is a product of three layers: skin, bone and brain tissue. Approximate thicknesses are shown. Developing a temporal interface model (FIG. 12A) in more detail requires information about sound velocities and attenuation in the various tissue types. Tissue-specific attenuation constants can be approximated from literature values factored for measured thickness and the combined attenuation profile can then be calculated as a function of depth, where attenuation of $P_r$ across a temporal acoustic window is given as (Eq 1):

$$|P_r(z)| = \frac{PrA_z}{PrU_z}$$

where $P_r(Z)$ is the ratio of attenuated ($P_{rAz}$) to unattenuated ($P_{rUz}$) ultrasonic pressure as a function of depth (z) in centimeters. Attenuation can be solved from Eq 2:

$$A_{TOTAL} = A_{SKIN} + A_{BONE} + A_{REFLECTION} + A_{BRAIN}$$

or, $$A_{TOTAL} = 20 \cdot \log_{10} \frac{P_{rAz}}{Pr_{Uz}}$$

And combining equations 1 and 2 yields (Eq 3), $$P_{rAz} = P_{rUz} * 10^{\frac{(A_{SKIN}) + (A_{BONE}) + (A_{REFLECTION}) + (A_{BRAIN})}{20}}$$

where, $P_{rAz}$ is the attenuated peak rarefaction pressure at depth z on the beam path;

$P_{rUz}$ is the unattenuated peak rarefaction pressure at depth z;

$A_{SKIN}$ is the acoustic attenuation in the outer skin and tissue;

$A_{BONE}$ is the acoustic attenuation through the skull bone;

$A_{REFLECTION}$ is the attenuation equivalent to reflection losses at the interface between the inner surface of the skull and the brain, nominally 3.02 dB;

$A_{BRAIN}$ is an acoustic attenuation in the brain, typically a constant at about 0.06 dB/mm-MHz;

z is a depth, the distance a ultrasonic beam wavefront has traversed;

$t_{SKIN}$ is the thickness of the outer skin and tissue layer;

$t_{SKULL}$ is the thickness of the cranial bone proximate to the transducer; and, $f_c$ is the center frequency (MHz).

Each component is now considered separately. The following attenuation coefficients, taken from the general literature, are tabulated for reference:

TABLE 1

| Tissue Type | $\alpha_{TT}$ (dB/mm-MHz) |
| --- | --- |
| Skin | 0.18 |
| Fat | 0.04 |
| Muscle | 0.09 |
| Sub-occipital brain tissue | 0.09 |
| Temporal brain tissue | 0.08 |

Skin attenuation is typically small and may be neglected, but is given by (Eq 4):

$$A_{SKIN} = (\alpha_{SKIN} \cdot f_c) \cdot t_{SKIN}$$

Bone attenuation is significant and is dependent on thickness of the bone in the path of the transducer beam, frequency and is best described by a non-linear curve fit of physiological data. The attenuation for temporal bone ($A_{TempBONE}$) was solved by parabolic curve fit of available data (FIG. 11B) and is described mathematically as (Eq 5):

$$A_{TempBONE} = (-0.186 \cdot f_c^2 + 3.257 \cdot f_c - 1.51) * t_{SKULL}$$

The regression fit ($R^2$) for this equation was 0.875.

Brain attenuation is given by (Eq 6):

$$A_{BRAIN} = \alpha_{BRAIN} \cdot t_{BRAIN}$$

Reflection attenuation at the SKULL:BRAIN interface is a function of the relative difference in acoustic impedance between the temporal bone and underlying brain tissue and is essentially a constant:

$$A_{REFLECTION} = 3.02 \text{ dB}$$

By knowing boney layer thickness and having reference values for constant terms, transducer voltage may be adjusted to achieve a target $P_r$ at a defined depth z. In a first embodiment of the device, $t_{SKULL}$ is measured and $A_{SKULL}$ is calculated, resulting in the total attenuation plus reflection ($K_{SKULL}$) in decibels for a measured skull thickness proximate to the transducer. This is based on pooled acoustic measurements as reported by others. A similar measurement and calculation may be made for skin. In most instances, the attenuation associated with the outer skin layers is negligible compared to the larger contribution of the cranial bones.

As previously indicated, acoustic reflection is given as −3.02 dB as a first approximation, so equation 3 is further simplified to (Eq 7):

$$P_{rAz} = P_{rUz} * K_{SKULL} * 10^{(A_{BRAIN} * (z - tSKIN - tSKULL) * f_c)/20}$$

where $P_{rAz}$ is the calculated peak attenuation at depth z and $P_{rUz}$ is the measured rarefaction pressure at depth z as measured in a tank of water.

This equation is readily solved by a calculating machine, such as a microcontroller with on-board math functionality when given skull layer thickness, and permits the device to predict $P_{rAZsp}$ (peak rarefaction pressure at $z_{sp}$) based on a measurement of skull layer thickness such as by CT scan.

In practice, the voltage required may be calculated from transducer calibration data such as illustrated in FIGS. 13A and B. Control of insonation intensity is achieved by adjusting or correcting the voltage applied to the transducer ($V_{p-p}$), where as shown in FIG. 13A, it can be seen that acoustic intensity is a linear function of voltage. More simply, the relationship between pressure $P_r$ and voltage is linear, as shown in FIG. 13B, where a representative curve at 1 MHz is shown. At any given frequency, for a desired peak rarefaction pressure in MPa, the voltage ($V_{p-p}$) required can readily be calculated from a linear slope and intercept. Alternatively, a simple look-up table may be used by the calculating machine to make the adjustment in voltage based on data provided for skull thickness.

Thus for a transducer situated on the temporal acoustic window, the rarefaction pressure as a function of depth in the cerebrum can be plotted as shown in FIG. 13C. Here nested curves are shown for a 1 MHz transducer excited at voltages between 30 and 80 $V_{p-p}$. Control over acoustic pressure is achieved by calibrating the voltage response for each transducer individually and then adjusting boost voltage in the pulse generator circuit accordingly, as will be described in more detail below.

Turning to FIG. 12B, a physical model for analysis of an attenuation profile as a function of depth for a transducer seated at a sub-occipital acoustic window is described. The figure depicts a sub-occipital transmission path for ultrasonic energy into the cranial vault between the spinal column and the foramen magnum. The physiology is distinguished from the temporal window by a general absence of a boney layer, and attenuation is substantially lessened.

As the ultrasound pressure waves propagate from the transducer face to the point of maximum exposure in the cranium (it is assumed the primary mode of wave transmission is transverse, i.e. waves travelling parallel to the face of the transducer), the overall model for attenuation along the suboccipital path can be approximated by evaluating the transmission characteristics across four major layers each with a tissue attenuation coefficient: Skin, fat, muscle, and brain tissue as shown in FIG. 12B.

Attenuation can be solved from Eq 8:

$$A_{TOTAL} = A_{SKIN} + A_{FAT} + A_{MUSCLE} + A_{BRAIN} = 20 \cdot \log_{10} \frac{P_{rAz}}{P_{rUz}}$$

And similarly as before (Eq 9), $$P_{rAz} = P_{rUz} * 10^{\frac{(A_{SKIN})+(A_{FAT})+(A_{MUSCLE})+(A_{BRAIN})}{20}}$$

where,
$P_{rAz}$ is the attenuated peak rarefaction pressure at depth z on the beam path;
$P_{rUz}$ is the unattenuated peak rarefaction pressure at depth z;
$A_{SKIN}$ is the acoustic attenuation in the outer skin;
$A_{FAT}$ is the acoustic attenuation through the bone;
$A_{MUSCLE}$ is the attenuation through the fat layer;
$A_{BRAIN}$ is an acoustic attenuation in the brain, typically a constant at about 0.06 dB/mm-MHz;
z is a depth, the distance a ultrasonic beam wavefront has traversed;
$t_{SKIN}$ is the thickness of the outer skin layer;
$t_{FAT}$ is the thickness of the fat layer;
$t_{MUSCLE}$ is the thickness of the muscle layer; and,
$f_c$ is the center frequency (MHz).

Each component is now considered separately. Attenuation coefficients (a), were previously tabulated (Table I).

Skin attenuation is typically small, but is given by (Eq 10):

$$A_{SKIN} = (\alpha_{SKIN} \cdot f_c) \cdot t_{SKIN}$$

where thicknesses are on the order of 1 mm.

Fat tissue attenuation is given by (Eq 11)

$$A_{FAT} = (\alpha_{FAT} \cdot f_c) \cdot t_{FAT}$$

Based on empirical observation of experienced TCD sonographers, the total tissue thickness on the back of the neck will vary between 2 to 5 cm, of which 1 cm is muscle. Thus, the fat layer can vary between 1 to 4 cm.

Muscle tissue attenuation is given by (Eq 12)

$$A_{MUSCLE} = (\alpha_{MUSCLE} \cdot f_c) \cdot t_{MUSCLE}$$

Nominal muscle thickness is taken as 10 mm for most applications.

Brain attenuation is given by (Eq 6):

$$A_{BRAIN} = \alpha_{BRAIN} \cdot t_{BRAIN}$$

Because of the large variability in the fat layer and the variability in the point of maximum pressure ($z_{sp}$) depending on transducer selection, it is possible that the actual point of maximum peak negative pressure could be in an adjacent layer to the brain instead of in the brain itself.

If the fat layer on a patient is 1 cm thick, then the point of maximum peak negative pressure will certainly be inside the brain. Mathematically, if $z_{sp}$=3 cm, and the overlying layers of tissue are 2.1 cm thick (=0.1 cm+1 cm+1 cm) (skin+fat+muscle), $P_{rAmax}$ is 0.9 cm into the brain tissue. $P_{rAmax}$ is P the point of maximum acoustic amplitude in tissue. The computation of attenuation is straightforward unless $P_{rAmax}$ is situated in the connective tissue layers.

If $z_{sp}$ is inside the fat or muscle layer, the estimate changes. In this case it is necessary to consider the total attenuation across the skin, fat, and muscle and then estimate the peak negative pressure at the muscle-brain tissue interface. This will be the estimated maximum peak negative pressure ($P_{rAmax}$) in brain tissue.

For most ultrasound systems, the peak negative pressure is conservatively assumed to decrease by about 0.5% per centimeter. Thus, the maximum peak negative pressure in the brain tissue (before accounting for the other attenuation values) can be estimated (for $z_{sp} \le t_{SKIN} + T_{FAT} + T_{MUSCLE}$) from (Eq 12):

$$P_{r(Amax)} = P_{r(Uz_{sp})} \cdot (-0.05(t_{SKIN} + t_{FAT} + T_{muscle}) + (0.05 z_{sp}) + 1)$$

And for $z_{sp} > t_{SKIN} + t_{FAT} + t_{MUSCLE}$, $$P_{r(Amax)} = P_{r(Uz_{sp})}$$

Practical uses of these equations in configuring headset electronics were described above, as for the model system described in FIG. 12A.

FIG. 14 illustrates peak rarefaction pressure as a function of depth, and is depicted schematically for thin skulled (205) and thick skulled (206) persons. A preferred zone of insonation (204, box with dotted line) is shown at depths of 4 to 7.5 cm bilaterally, where most major stroke thrombi are found. Rarefaction pressure is desirably 20 to 150 KPa in this zone, which extends on the abscissa from 4 to 11 cm. As shown here, while the invention is not limited thereto, maximal pressures obtained in the target zone are about 150 MPa, in order to cap the intensity of tissue exposures at $z_{sp}$, where the transducer beam pressure is maximal, to less than 300 KPa, as will be discussed further below. For 1 MHz transducers used in a first device of the invention, $z_{sp}$ was measured at about 1.2 cm in vitro; for 2 MHz transducers used in a second device of the invention, $z_{sp}$ was measured at about 3 cm in vitro. These results are dependent on the details of manufacture of the transducers and are not intended to limit the invention thereto. In actual use, $z_{sp}$ is typically closer to the transducer interface. Thus, although the transducers are non-focused transducers, beam amplitude has a maximum at a generally known distance from the transducer face and beyond that point soundwaves progressive weaken by divergence and spreading of the beam. Individual variation of transducer output has also been observed and is detected by calibration studies. Simultaneous insonation from multiple transducers, for example from contralateral transducers, results in additive pressures in the overlapping areas as is depicted in FIG. 14.

The transducers of the invention may be configured so that sound fully attenuates over about 15 cm, for example, so that a rebound echo from the contralateral skull wall of an adult is minimal or negligible. The pulse interval may also be widened to prevent echoes from constructively interfering with outgoing pulses and increasing local rarefaction pressures beyond the acceptable limit of 300 KPa as described here. Fortuitously, increasing the pulse interval decreases the duty cycle, so that overall energy consumption is reduced and the device can be operated for longer periods of time without recharging.

As previously alluded to, frequency, pulse modulation pattern, and pulse metacycle are factors in efficacy and safety and the patterned waveforms selected for use are features of the invention. Frequencies selected for operation of the devices of the invention are in the range of 0.5 to 3.5 MHz. As frequency is increased, mechanical index decreases, but thermal index increases inversely. Therefore a range of 0.8 or 0.9 to 3.5 MHz is a preferred range. Reduction to practice at 1 MHz and 2 MHz has been realized in clinical trials. Another preferred frequency is about 1.2 MHz. Care is taken in selecting parameters of pulse width, intensity and pulse repetition frequency not to exceed an integrated $I_{spta.3}$ limit of about 720 mW/cm², and not to exceed a physiologically compatible TI.

Cyclical metapulse repetition frequency (MCRF) and duty cycle may also be used to limit power consumption and permit heat dissipation by passive means such conductive and convective cooling from external surfaces of the headset and transducers, and is configured not to overstress the cooling capacity of the wearer.

In selected embodiments, patterned waveforms of programmed insonation comprise a train of pulses, each said pulses having a pulse duration of about 0.2 to 10 microseconds, more preferably about 1 to 8 microseconds, most preferably about 6 microseconds, in trains of pulses of 2 to 300 pulses per train, more preferably of about 100 to about 300 pulses per train, said train of pulses having a pulse repetition frequency of about 3 KHz to about 10 KHz, more preferably about 4 KHz to about 8 KHz, and most preferably about 6 KHz, with an amplitude measured as unattenuated peak rarefaction pressure of 0.5 to 1.0 MHz, and at a ultrasonic frequency of 0.5 to 3.5 MHz, more preferably about 0.8 or 0.9 to about 3.0 MHz, and most preferably about 1 MHz, or about 1.2 MHz, or about 2.0 MHz. The pulse trains are also vectored from multiple independently fired transducers, thus resulting in spatial modulation or distribution of the patterned waveforms.

FIG. 15A illustrates by way of example a typical pulse consisting of multiple sinusoidal sound waves (209) at a primary frequency $f_c$. Each pulse (210) consists of about 12 sound waves as shown. At 2 MHz, a pulse of this kind has a pulse width of about 6 microseconds. Pulses of this kind may be fired in series with a pulse repetition frequency (PRF) of about 6 KHz, for example, and are thus fired from an individual transducer at a pulse interval (PI) of about 167 microseconds, corresponding to a duty cycle of about 3.6%, while not limited thereto. Duty cycle may range from 0.1-10%, more preferably 3-5%, and most preferably about 3.5±0.5%. In other embodiments, pulse amplitude or pulse frequency modulation may also be used.

FIG. 15B describes a series of 20 pulses (210a-210n) emitted from a single transducer. Taken together, the individual pulses form a 'pulse train' (211).

FIG. 15C illustrates a pair of pulse trains (211a, 211b), each pulse train consisting of multiple pulses in series. Scale is not shown and the individual pulses are not distinguishable. For illustration, 100 to 300 pulses may be grouped in a single pulse train fired from a single transducer, the pulse train having a pulse repetition frequency (PRF). In this figure, two consecutive pulse trains are shown, a repeated cycle of consecutively fired pulse trains constitutes a "metapulse" (212), the metapulse here having two pulse trains (211a, 211b). Simultaneous firing of particular transducer pairs or triplets may be used where amplitude is not additive.

In FIG. 16A, another illustration of a metapulse is shown. Along the left margin, individual traces are labeled with designations for particular transducers of each array, for example "RT1" is right temporal #1 transducer, "OC1" is occipital #1 transducer, and so forth. The figure represents one complete firing sequence of the headset, one cyclical "metapulse" (214) with 16 pulse trains. One pulse train is fired from each of sixteen transducers in the course of a single metapulse. Thus the timeline can be viewed as a staggered chronology where a first transducer fires a first pulse train (213a), a second transducer fires a second pulse train, and so forth, . . . and finally a last transducer fires a last pulse train (213n) of the cycle, and the cycle can then begin again. By this means, selecting transducers from different arrays for consecutive actuation, the pulse trains strike the target anatomy like an "acoustic nudge", each acoustic perturbation arriving from a somewhat differing direction as the metapulse cycles. A 6 KHz pulse train of 100 pulses has a duration of about 16 milliseconds, and could be termed a "nudge" for stimulating streaming. The cyclical repeated metapulse is thus a "supernudge" composed of multiple "nudges," each nudge a train of pulses. In another sense, the about 6 KHz frequency may be considered to be a "carrier wave" frequency.

Individual transducers may be directed at particular anatomical targets, but non-focused ultrasound used here spreads along its 6 dB beamwidth and strikes a broader target area at depth. FIG. 16A thus illustrates a three-dimensional patterned cyclical emission or "metapulse" of pulse train emissions from an array of sixteen crystals, where each crystal emission is directed in a unique general direction and is fired once per cycle. It can be said that the insonation regime depicted here is a cyclically repeating metapulse comprising one or more patterns of temporally modulated and spatially distributed pulse trains, each pulse train comprising multiple ultrasonic pulses. The insonation can thus be characterized as cyclically and stereotemporally modulated insonation. While not limiting in characterizing the invention, a headset with 16 transducers firing 16 millisecond pulse trains, one at a time, will cycle sequentially about every half a second. Mutatis mutandi, other permutations are possible by theme and variation around the concept of a pattern within a pattern within a pattern of temporally modulated and spatially distributed acoustic beams.

In general, patterned waveforms of programmed insonation comprise a train of pulses, each said pulses having a pulse duration of about 0.2 to 10 microseconds, more preferably about 1 to 8 microseconds, most preferably about 6 microseconds, in trains of pulses of 2 to 300 pulses per train, more preferably of about 100 to about 300 pulses per train, said train of pulses having a pulse repetition frequency of about 3 KHz to about 10 KHz, more preferably about 4 KHz to about 8 KHz, and most preferably about 6 KHz, with an amplitude measured as unattenuated peak rarefaction pressure $P_{r0}$ of about 0.3 to about 1.0 MPa or more, and at a ultrasonic frequency of 0.5 to 3.5 MHz, more preferably about 0.8 or 0.9 to about 3.0 MHz, and most preferably about 1 MHz, or about 1.2 MHz, or about 2.0 MHz. The pulse trains are also spatially vectored from multiple independently fired transducers, thus resulting in spatial modulation or distribution of the patterned waveforms.

An apparatus of the invention has program instructions that encode for autonomously driving a plurality of ultrasound transducers to emit a cyclically repeating metapulse, the metapulse comprising a wavepattern of spatially and temporally modulated pulse trains of ultrasound having a primary frequency $f_c$, and an amplitude configured to achieve a $P_{rAZsp}$ not to exceed 300 KPa, the pulse trains having a pulse repetition frequency corresponding to a duty cycle of 0.1-10%, more preferably 2-6%, and most preferably about 3 to 5% per transducer, the metapulse having a metapulse cycle repetition frequency of 0.25 to 10 Hz, until a stop instruction is received; thereby achieving low power consumption for extended portable operation independent of operator control and not requiring assisted cooling means.

The inventive devices may be built with multiple transducers formed as transducer arrays, each transducer array having a plurality of individually controlled piezoelectric crystals, permitting the emission of patterned meta-cycles of patterned pulse trains in complex modulations made possible by multiplexing a pulse generator signal or signals, for example across multiple logic gates actuated at selected clock frequencies as shown in FIGS. 20A-D, as will be discussed below. In a preferred embodiment, the individual transducers may be about 1 cm in diameter or smaller and are spaced apart (unlike conventional phased array transducer assemblies) to permit heat dissipation between firings. The transducer crystals are not fired in pairs and the beams emitted are not convergent, but are instead fired individually in series under autonomous control of a remote controller unit, which contains a clock, pulse generator, logic circuits for transducer actuation, and optionally with control of amplitude of individual transducer output as compensation for attenuation or inter-transducer variability. This multiple mini-transducer approach has been proven to be safe, cognizant of the dangers of standing waves and heating, and is found to be surprisingly effective in sono-thrombolysis. While not bound by theory, the device is thought to stimulate diffusion of r-tPA by insonation-induced fluid streaming in response to modulated pulsed ultrasound patterns directed at a target anatomy from multiple directions, where a first transducer is fired with a pulse train or "acoustic nudge", a second transducer is then activated, and between each pulse of each pulse train, the emitted ultrasonic wavefront is allowed to fade in intensity. Taking into account a temporal-temporal or occipital-frontal beam path length of 10 to 15 cm in a typical application, the pulse interval is thus on the order of 1 to 2 microseconds, as was described in more detail in the preceding section. The overall "metapulse" may have a MCRF of about 2 Hz in the example of FIG. 16A and describes a complex modulated pattern of distributed pulses. The overall pattern or waveform is a cyclical pattern comprising spatially distributed and temporally modulated meta-pulses formed from sub-patterns of pulse trains and constitutes a therapeutic regimen.

The apparatus may be programmed using instructions in EEPROM, for example, and may have a repertoire of therapeutic regimens at its disposal that are selected in response to sensor data or altered according to predetermined criteria, and so forth. The device may be configured for diurnal use for example, or individually tailored cyclical patterns are provided for prophylactic applications which may be switched to more intensive therapeutic patterns in the event of a vascular stroke, mini-stroke, an increase in intracranial pressure, or transient ischemic attack, and so forth.

Other pulse and metapulse chronologies are readily conceived. FIG. 16B describes a metapulse sequence 216 where two metapulses are shown (repeating pattern, left to right). Each metapulse consists of pulse trains fired by various pairs of transducers simultaneously. The duplex pairs selected for simultaneous firing are generally contralateral pairs so as to minimize potential additivity in the amplitude of the peak pressures where the beams meet. However, study has shown that contralateral beams can be configured to overlap so that constructive addition of beam intensity is beneficial at target depths of 4 to 7 cm (for each hemisphere) and does not exceed safe limits at any depth. A total of 32 pulse trains are emitted in this example (215*a*-215*n*), but the invention is not limited thereto.

FIG. 16C describes a metapulse sequence (218) consisting of triplets and doublets, where three metapulses are shown (repeating pattern, left to right). Each duplex or triplet emission consists of simultaneous pulse train emissions by two or three transducers. Again these are chosen so that additive effects are most beneficial at depth. By firing three transducers at once, where the individual transducers are selected from the right temporal, left temporal and occipital arrays, amplitudes do not rise above safe levels where beams overlap. A total of 48 pulse trains are emitted in this example (217*a*-217*n*), but the invention is not limited thereto.

Individual arrays may be actuated more frequently than others, for example when it is desirable to preferably insonate a particular hemisphere of the brain or a frontal versus an occipital aspect of the cerebral vasculature. In other instances, particular transducers are chosen to fire more frequently than others so as to optimize acoustic streaming in a particular direction, such as circularly in the Circle of Willis by firing posteriorly-directed Rt temporal transducers in alternation with anteriorly-directed Lt temporal transducers in alternation, and then reversing the direction by firing anteriorly-directed Rt temporal transducers in alternation with posteriorly-directed Lt temporal transducers, so as to create clockwise and counterclockwise pressure gradients which stimulate directed acoustic streaming and flow. Also of interest are reciprocating pressure pulses, such as alternating pulse trains between matching transducers situated contralaterally in the temporal arrays, or orthogonally directed pulses in alternation from ipsilateral transducers of the temporal and occipital arrays, for example.

By firing only a few transducers at a time, and by firing individual transducers (as determined by the pulse repetition frequency) at a duty cycle in the 0.1 to 10% range, more preferably in the about 3 to 6% range, and in one embodiment with a duty cycle of about 3.6%, the need for assisted cooling is avoided. TI and thermal heating effects are limited. This approach permits use of higher frequencies, which can be advantageous because mechanical index (MI) is more easily limited. Lower power consumption also results; without loss of efficacy. The apparatus is typically passively air-cooled, avoiding power consumption by fans, circulating coolant, and so forth.

The requisite pulse interval can be achieved with a pulse repetition frequency of about 4 to 10 KHz, more preferably about 5 to 8 KHz, and most preferably about 6 KHz. Fortuitously, this PRF is more physiologically compatible than lower frequencies in that users have been observed to perceive pulsed insonation in the 2-4 KHz range, in particular, as an uncomfortable sound; paradoxically sensing, by a sort of biological demodulation, what is by definition an inaudible ultrasonic pulse. The 0.5 to 3.5 MHz primary frequency is well above the range of human hearing but can be "demodulated" when pulsed at 2-4 KHz.

FIG. 17 quantifies the threshold for audible sensation of ultrasound exposure as a function of a modulated pulse train frequency. Greater amplitudes are required to elicit a sensation outside the range of 0.2 to 4 KHz. In other words, pulse repetition frequencies greater than about 4 KHz are less likely to be perceived by the user. Frequencies in the 2-3 KHz range are most perceptible. Happily, selection of a 5 or a 6 KHz pulse repetition frequency solves this problem for most individuals and, at a duty cycle of 3 to 6% or so, poses no significant increase risk of excessive heating or overexposure as measured by TI and $I_{sppa.3}$. At greater than 10 KHz PRF, overlap of successive wave patterns can be associated with standing waves, so 4-10 KHz has proved to contain a narrow range of comfort where safety is not compromised.

FIG. 18 is a flow diagram for autonomous operation of the device. The steps form a basic method for therapeutic transcranial ultrasound, where a headset is positioned on a user's skull and positioned using the stereotactic registration brackets provided. The headset is tightened, generally with gel on the transducers to ensure good acoustic coupling. Tightening is achieved by tensioning the posterior headband member and does not shift the anterior headframe member or registration brackets, thus ensuring that the stereotactic alignment with respect to the cerebral vasculature is not disturbed. The temporal transducer array subassemblies are slid into optimal position prior to tightening.

The headset is operated via a cable to a controller unit with power supply via that is carried with the headset and permits remote operation of the power supply and on-off/pause control. The device may be monitored by the user, goes through a self-check, and will generally display a signal that all systems are green for GO. Ultrasonic headset emissions then begin. The emission is a complex pattern of spatially distributed and temporally modulated metapulses of the kind shown in FIGS. 16A-C, which continue until the device is paused or for a duration of time preset in the programming. The therapeutic regimen may be repeated if desired.

Surprisingly, power and wave patterns of the insonation regimen may be fully automated for therapeutic transcranial insonation, without user intervention or adjustment, for periods of 2, 4 or up to 12 hours or more under battery power. Physician involvement is not generally needed during this phase of treatment. Passive cooling and other energy saving means are used to achieve this extended operation, which has proven therapeutically beneficial prophylactically and during the post-stroke recovery phase, when recanalization is partial or tenuous, and re-occlusion occurs with some frequency. Cyclical metapulse repetition frequency (MCRF) and duty cycle are used to limit power consumption and permit heat dissipation by passive means such conductive and convective cooling from external surfaces of the headset and transducers, and are configured not to overstress the cooling capacity of the wearer. Battery life is also extended by eliminating the need for diagnostic imaging in placement and monitoring of the therapeutic insonation. Thus the method is an advance in the art.

FIG. 19 shows the steps of an improved method for automated operation of an apparatus where voltage is adjusted by the automaton on the fly to compensate for transducer-to-transducer variability. Following attachment of the headset circumcranially around a skull, generally with gel on the transducers to ensure good acoustic coupling, the apparatus is powered on and performs a startup self diagnostic. The apparatus then determines, for example, the appropriate calibration factor for each individual transducer from a look-up table associated with the transducers, and increments (or decrements) a voltage correction for $V_{BANG}$ as described in FIGS. 20A-B. If all systems are go, the apparatus commences an insonation metapulse cycle of the kind illustrated in FIGS. 16A-C and continues this until paused or for a duration of time preset in the programming. The cycle may be repeated if desired.

An electronic mechanism for adjusting transducer amplitude on the fly is described in the following electrical schematics, which also show the operation of the pulse generating circuit with multiplexed control and sensing of the transducer arrays. Because the device is operating independently from operator control, and is self-adjusting once properly seated on a head, variation in therapeutic delivery is significantly reduced, an advance in medical care for stroke. Because the device operates without skilled positioning and adjustment, therapy is accessible to a greater number of stroke victims. Surprisingly, the device may be used for other neurological conditions such as migraine or headache, where its non-invasive character poses little risk and significant benefit, and is also of benefit in enhanced drug delivery and dispersion of endogenous mediators, as will be discussed below.

Referring now to FIG. 20A, shown is a block diagram of a circuit schematic ("circuitry" 240) with functional blocks indicating the basic electronic components of a system operating as an automaton. A wiring harness from the headset is attached and is indicated here by a coaxial cable (COAX). Although multiple leads for powering multiple transducers may be contained in the wiring harness, only a single lead and transducer is shown here for clarity of explanation.

The microcontroller is optionally an Intel P8051 (MCS51), but is not limited thereto. Microprocessors with advanced mathematical processing capacity may also be used. The MCS51 package may contain fully integrated non-volatile memory such as EEPROM, and RAM, IO, UART and timer functionality, or optionally the accessory functions may be discrete. Shown here as independent functionalities are an EEPROM unit for providing programmable instructions and look up tables to the microcontroller, a CLOCK functionality for providing a frequency that may be used by a clock divider and by the microcontroller, and four functional blocks related to transducer send and receive functions, including a multiplexer (MUX, 245), a demultiplexer (DEMUX, 244), a voltage or "boost" regulator (VREG), and a pulse generator sub-circuit (PULSE GEN).

The pulse generator, demultiplexer and voltage regulator are used to control and direct pulsed waveforms to the transducer or transducers 241. The pulse generator circuit drives a resonant oscillating voltage signal at a primary frequency $f_c$. The voltage regulator receives a voltage $V_{BAT}$ from a battery (not shown) and outputs a higher voltage $V_{BANG}$. $V_{BANG}$ is used to control individual transducer $V_{p-p}$, i.e. transducer insonation amplitude. The voltage regulator may be an LM4510 (Natl Semiconductor) Step-Up DC/DC Converter, while not limited thereto. The LM4510 is designed to delivery up to 120 mA at 16V from a 3.6V input of a lithium ion battery at a switching frequency of 1 MHz with greater than 85% efficiency, with provision for non-synchronous operation at light load to maximize power efficiency. NMOS output is regulated by a bias voltage applied at a feedback connection. The fixed frequency is dependent on an external LC oscillator (252-253, FIG. 20B) wired to the FET transistor. No Schottky diode is required. R2 is an isolation resistor and C1 is a filter. Capacitor C2 works with transformer T1 and the piezoelectric crystal TDX to resonate at a center frequency $f_c$.

As described in FIG. 20B, a voltage regulatory circuit (250) for $V_{BANG}$ is modulated by feedback resistor bias voltage (WIPER) applied to pin FB of a LM4510 Boost Regulator (251), for example. By substituting a digital potentiometer DS1804 (254, supplied by Dallas Semiconductor (Dallas Tex.), or equivalent device, for the fixed resistance customarily used, control of $V_{BANG}$ applied to the centertap of the transformer 242 is achieved, and transducer insonation amplitude may be increased or decreased on the fly. In this way the voltage of each pulse or burst directed to an individual transistor by the DEMUX logic gates (246, FIG. 20A) is "dialed in" to produce a corresponding amplitude of transducer insonation at each individual transducer as necessary to compensate for transducer-to-transducer variability, an advance in the art.

$V_{BANG}$ may be used to control for manufacturing variation in transducer output versus applied voltage. An efficiency or rating factor for each transducer crystal stored with the headset or transducer subassembly may be accessed by the microcontroller during startup and used to separately vary the voltage applied to each crystal of the headset so as to compensate for manufacturing variation. This accomplishes an advantageous reduction in intra-headset variability of ultrasonic treatment.

The microcontroller is responsible for controlling $V_{BANG}$ via a signal (255, uC) to a digital potentiometer, which generates a WIPER voltage applied to the feedback input (FB) of the voltage regulator for controlling the voltage boost. Signal values to be applied for each transducer of an array may be stored in tables in nonvolatile memory. The non-volatile memory may be the EEPROM shown in FIG. 20A or a remote memory associated with the array subassemblies on the headset and accessed via a digital bus. Also shown by way of illustration of a working embodiment are external capacitor C3 (253) and inductor element L3 (252) used with the internal FET switch in the voltage boost functionality for boosting voltage under microcontroller control, here using the LM4510 boost regulator and digital feedback potentiometer (DS1804), while not limited thereto.

Referring again to FIG. 10A, the PULSE GEN functionality generates a waveform FREQ1 corresponding to the ultrasonic resonant frequency of the transducer TDS. FREQ1 controls switch SW1 when AND gate (246) is high and drives a resonant oscillation in transformer T1 (242). FIG. 10C describes the PULSE GEN functionality at a component level, where transformer T1 is provided with centertap for receiving $V_{BANG}$ and switches for driving the transformer at frequency $f_c$. Switches Phi1 and Phi2 are controlled by the microprocessor and clock functions. SEL is received from DEMUX as described below.

To turn on AND gate (246, FIG. 20A), DEMUX (244) output SELX is addressed under control of the microcontroller. In one embodiment, the DEMUX function is a 4:16 demultiplexer for address decoding, where each address is one of sixteen transducers and is controlled by a separate AND gate. The DEMUX function is used to gate the FREQ1 signal through a step-up center tap transformer for generating a 0 to 250 V signal applied across each transducer crystal, which in operation behaves in certain respects as a capacitor. The transformer T1 and transducer TDX pair may be viewed as a resonant LC pair having higher power efficiency. In this way, a fixed frequency (for example 1 MHz or 2 MHz) is applied to the transducer(s) in bursts or pulses, with a pulse frequency controlled by the DEMUX signal applied to the AND gate (246). More generally, a plurality of transducers (270a, 270b, 270n) are gated (246a, 246b, 246n) in this way as shown in FIG. 20D and a primary frequency signal (PULSE GEN, 271) may be selected between 500 KHz to 3.5 MHz, for example. Working in conjunction with $V_{BANG}$, the demultiplex circuit output to the transducers has an analog output with an un-derated peak rarefaction pressure $P_{r0}$. By using a second or third pulse generator circuit gated in parallel, frequencies and intensities sent to any particular transducer of an array may be customized for particular applications. The DEMUX functionality may also address multiple transducers at once if desired for simultaneous firing in pairs or triplets. Intermittent firing of the transducer allows the headset to be operated without assisted cooling and is a low power consumption feature of the circuitry. Eliminating the need for active cooling dramatically decreases overall power draw of the apparatus and is an advance in the art.

MUX (245, FIG. 20A) is used in "receive" mode to collect echo voltage generated at the transducer (TDX) surface as received on the input lead and to convey a digitized voltage signal to the microcontroller, generally as shown in FIG. 20C, where the sensed voltage is Rcv. Like DEMUX, MUX is multiplexed to collect voltages from multiple transducer leads. Multiple transducer signals from an array or arrays of transducers may be multiplexed in this way. The coaxial cables as shown (COAX) in FIGS. 20A, 20B and 20D thus may consist of multiple bundled leads and the wire harness has corresponding multiple points of attachment to the printed circuits for performing the block functions of FIG. 20A. MUX output to the microcontroller thus is a digital signal with unique address corresponding to each transducer.

FIG. 21 is a logic diagram for autonomous operation of a device configured for detection of acoustic coupling under each transducer prior to initiation of therapeutic insonation, and will default if coupling requires adjustment, and represents an improvement over the basic method of FIG. 18. This functional block verifies acoustic coupling between the transducer and the skin after the headset is positioned on the skull of the user.

FIGS. 22A and 22B describe the use of phase angle θ to verify acoustic coupling. FIG. 22B plots voltage output corresponding to phase angle for a coupling verification circuit of FIG. 23. In this application, an ultrasound pulse may be used to validate acoustic coupling between the transducer interface and the underlying tissue target. If a transducer is not acoustically coupled to the underlying skull, generally with a couplant gel, the ultrasound bounces off the intervening air layer and fails to penetrate the skull. To verify coupling, in one embodiment, a voltage comparator circuit is used to measure phase angle of the voltage pulse activating the transducer. A high phase angle is indicative of poor coupling, generally indicating the presence of air between the transducer and the target tissue. A low phase angle indicates good coupling. These circuits are practical solutions to the problem of ensuring good acoustic coupling before initiating an autonomous ultrasonic pulse treatment regime. The microcontroller will verify that the phase angle does not exceed a preset threshold before initiating insonation.

As shown in FIG. 22A, an impedance matching system may be designed to match source and load impedances when the headset is properly seated and acoustically coupled on the cranium. The signal source in this application is an amplified clock frequency emitted in pulses and the load is a piezoelectric transducer.

In considering an ultrasound transducer with a capacitive reactance, overall power load impedance is the sum of a real resistance "R" and an imaginary reactance "−jX". Current is shifted in phase by an angle θ relative to voltage.

Total impedance $Z_{mag}$ is calculated as:

$$Z_{LOAD} = R - j/\omega C$$

where R is resistance in ohms, w is frequency expressed as radians, ω=2πf, where f is the frequency in Hz, and C is capacitance expressed in Farads, which may also be written, $$Z = \sqrt{R^2 + X_C^2}$$

where $X_C$ is the capacitive reactance (ohm).

Taking the RC network and assigning the real part of the impedance to the real axis and the imaginary part to the imaginary axis, the impedance vector $Z_{mag}$ will appear as in FIG. 22A.

The Pythagorean relationships for right angle triangle geometry, relating ordinate R, abscissa $X_C$ and hypotenuse Z, allows the impedance $Z_{mag}$ to be solved from the resistance and the capacitive reactance $X_C$. However, all that is needed to determine whether the surface of the transducer is acoustically coupled to an external load is the phase angle θ. The phase angle ($θ_{OPEN}$) will be large (ie. capacitive reactance will be large) when the transducer is acoustically mismatched with air, and will be dramatically lower ($θ_{COUPLED}$) when the transducer is acoustically matched with the tissue of the skull. This observation is illustrated in FIG. 22A. Thankfully, full measurement of the change in complex impedance (in phasor notation, $Z_{mag} \angle \theta$ for $Z_1$, $Z_2$) when coupling is established is not necessary for detection of an operative level of acoustic coupling between the crystals and the head of the subject wearing the headset. A rapid check of phase angle may be made by emitting an acoustic pulse and assessing phase angle of the pulse in a transducer. A circuit for digitally reporting the phase angle to a microcontroller is sufficient to assess acoustic coupling and the microcontroller can be programmed to perform this test individually for each transducer without operator intervention. If a transducer is not coupled, the operator will have to readjust the fit of the headset on the wearer, or eliminate any air between the transducer and the skin by adding gel couplant for example.

As shown in FIG. 23 schematically, implementation of circuitry (290) for phase measurement on a transducer load (293) driven by an oscillator (292) may be performed with an integrated circuit having a phase comparator, such as the HCT2046A (Philips Semiconductor, see 1997 Datasheet), which contains an edge triggered RS-type flip-flop phase comparator (PC3).

The average output from phase comparator (291), fed to the voltage comparator via the low-pass filter and seen at the demodulator output at pin 10 (295, $V_{PHASE}$), is the result of the phase differences of $SIG_{IN}$ and $COMP_{IN}$ are generally linear between 0 and 360 degrees theta as shown in FIG. 22B.

The output from $R_{SENSE}$ (294) can be offset to produce a desirable VPHASE=0 at zero degrees. More details of the device are provided in the 74HC/HCT4046A Phase-Lock-Loop with VCO IC data sheet from Philips.

The realization of these considerations is a phase detection circuit with linear output voltage that can be digitally encoded to flag an uncoupled transducer in a headset array for corrective action, as is needed for use of the device by relatively unskilled technicians or for self-use. A simple LED may be used to indicate an uncoupled transducer, for example.

In autonomous operation of an apparatus configured for detection of acoustic coupling under each transducer prior to initiation of therapeutic insonation, the apparatus will fault if coupling requires adjustment.

A variety of watchdog circuits to verify proper function before initiating insonation may be employed. Status lights or other indicator such as sounds, buzzers, LEDs, or even a liquid crystal display may be used to communicate the readiness of the device to begin ultrasound emissions. The LCD may for example scroll a message indicating that one of the transducers is not properly seated on the head. Status displays may also include battery status indicators, temperature sensors and indicators, and the like. Circuit fault detectors within the skill of those who practice electronic arts may also be incorporated.

Generally, frequency is also known, or easily measured, permitting use of $Z_{mag} \angle \theta$ information in other calculations, such as time of flight, which may be utilized in rudimentary imaging of midline shift conditions and quantitation of total dosage (from measurement of transducer-to-transducer pulse reception).

Now, turning to the biology and the range of vascular and neurological conditions where ultrasound has a role in therapy, FIG. 24 depicts schematically the competing cycle of fibrinogenesis (coagulation) and fibrinolysis (thrombolysis). Clotting is an excess of fibrinogenesis, results in deposition of insoluble fibrin strands from fibrinogen, and requires conversion of prothrombin to thrombin. Clot lysis is initiated by the presence of fibrin strands and requires the conversion of plasminogen to plasmin.

FIG. 25 is a schematic of the major limbs of the classical coagulation model. Both the Intrinsic Pathway and the Extrinsic Pathway join as a common pathway at activation of Factors IX and X, which are involved in propagating coagulation. Formation of a fibrin clot from fibrinogen requires thrombin and also Factor XIII (von Willebrand's factor) which binds to the nascent clot and promotes clot retraction through a process of activating a transglutaminase that acts on the fibrin strands.

Deposition of fibrin also attracts binding of plasminogen activator, which recruits plasminogen for conversion to the active serine protease plasmin that is active in reducing fibrin to small fragments known as fibrin split products.

FIG. 26 is a schematic of the "cellular model" of coagulation (after Monroe 2001 Thromb Haemost 85:958-965). Earlier conceptions had focused on soluble molecules active in coagulation, as were readily studied in the test tube, but overlooked essential cellular roles played by platelets in particular as scaffolding, toolboxes, supply cabinets and workbenches for coagulation reactions, but also leukocytes, macrophages, and endothelial cells in their essential role as promoters of fibrinolysis. Shown here are three key stages of coagulation, termed "initiation", "amplification", and "propagation". In the propagation phase, large scale conversion of prothrombin (PT) to thrombin leads to rapid and overwhelming deposition of fibrin.

Clot pathobiology is the basis for ischemic stroke, leading to both embolic attacks where clots enter the circulation from elsewhere in the body and become lodged in cerebral blood vessels, and direct formation of clots locally, from atheromas for example or as lacunar strokes, in the cerebral vasculature.

However, there are two types of stroke: ischemic and hemorrhagic. Depending on the type of stroke, treatment may be different. Speed is of the essence, but conventional practice is to first diagnose the nature of the stroke before initiating specific treatment. Ischemic stroke accounts for 70 to 80% of strokes, and occurs when a blood clot forms inside one of the blood vessels in the brain, cutting off the supply of blood and oxygen. Hemorrhagic stroke is caused by a blood vessel that bursts and leaks blood into the surrounding brain tissue, causing brain damage and includes intracranial hemorrhage (ICH).

For instance, an anti-clotting medication in hemorrhagic stroke could make the hemorrhaging even worse, and possibly kill the patient. Hemorrhagic strokes almost always require emergency surgery to repair the damaged blood vessel and remove the blood from the surrounding brain tissue. However, ischemic stroke can transform or convert to hemorrhagic stroke, and thus speedy action in implementing an effective thrombolytic therapy has important benefits. On the other hand, administration of r-tPA is associated with a small but increased risk of ICH conversion.

Thus the dilemma. As described above, administration of r-tPA has risks and is not generally initiated until a clear diagnosis of ischemic stroke has been made, losing precious time. A solution is needed that provides a benefit and can be initiated during the wait for definitive diagnosis. Unfocused ultrasound, modulated temporally and spatially as described here, is more safe than r-tPA when provided alone and is found to have a therapeutic benefit without exogenous administration of r-tPA and without invasive procedures. By selecting higher frequencies (frequencies in the range of 800 or 900 KHz to 3 or 3.5 MHz, more preferably about 1 MHz, 1.2 MHz, 1.5 MHz, 1.8 MHz, 2 MHz, or 2.2 MHz), the risk of exceeding safe limits of MI or $I_{spta.3}$ is reduced. By spatially and temporally modulating the ultrasound, the risk of exceeding TI is reduced. By the apparatus and methods of the invention, modulated ultrasound is directed at the cerebral vasculature as a whole from multiple directions (i.e. spatially distributed modulation) in a series of patterned pulse trains, what is essentially a pattern within a pattern within a pattern, where pulse trains of pulses are emitted from individual non-focused transducers and a plurality of transducers of a plurality of arrays are fired in a patterned order, one at a time. Surprisingly and unexpectedly, unfocused ultrasound may be administered beneficially in this way without specific information about the presence or location of a clot. Once this paradigm shift has been accepted, an operator-independent autonomous device for consistent and reproducible delivery of patterned waveforms becomes the standard of care. The technological features of the invention thus also have application in the treatment of other clot-related or circulatory conditions, such as deep vein thrombosis, and the apparatus and methods disclosed here may be adapted to a variety of body parts.

FIG. 27 depicts fibrinolysis involving endogenous (e-tPA) and exogenous (r-tPA) tissue plasminogen activator. Recombinant tPA (r-tPA) is known to accelerate fibrinolysis when administered intravenously and is regarded as the current gold standard of therapy.

FIG. 28A depicts fibrinolysis with tPA and ultrasound. Ultrasound is believed to promote clot breakdown by inducing acoustic streaming, where fibrin strands are loosened and fluid with soluble mediators of clot lysis is brought into contact with the newly exposed fibrin surfaces.

The mechanism of action in which ultrasound accelerates thrombolysis in the absence of microspheres is thought to rest with acoustic streaming, defined as movement of fluid induced by ultrasound (Sakharov et al. 2000). This streaming is essentially a mild stirring of fluids around the clot, which accelerates diffusion of macromolecules and fibrin split products, and exposes new clot surfaces for attack. As ultrasound output power and peak negative pressures are raised, this stirring action increases. A balance is required, as has been learned through difficult and dangerous trial and error, where in vivo peak negative pressure is increased to achieve clot dissolution effects, but must be reduced to minimize adverse bioeffects.

FIG. 28B tabulates clinical results in achieving recanalization and the associated intracranial hemolysis (ICH) per Alexandrov (2004 NEJM 535:2170-78) in stroke. Baseline ICH was slightly lower than reported in larger studies, and was not increased by co-application of ultrasound. However recanalization (REC) was significantly increased: a landmark study.

Surprisingly however, pulse modulation is more effective in application of ultrasound at the molecular, cellular and tissue level, as is the use of modulated ultrasound directed in alternation at a target from multiple directions in a repeating cycle of patterned pulse trains with a distinctive MCRF. The Alexandrov study employed a single focused transducer directed to an ischemic focus by an experienced sonographer. Because experienced sonographers are not readily to be found during the critical period following onset of a stroke, the stereotactic positioning and autonomous operation of the device and methods of the present invention offer a significant improvement in sonothrombolysis therapy.

FIG. 29A depicts fibrinolysis with tPA, ultrasound and microbubbles. FIG. 29B tabulates clinical results in achieving recanalization and the associated intracranial hemolysis per Molina (2005 Stroke 37:425-29). The device of the present invention is also expected to offer significant improvement in microbubble-assisted sonothrombolysis (also generally referred to as "microstreaming") and configurations for this application have been reduced to practice. Therapeutic improvement in outcomes to be obtained using a combination of r-tPA, microbubbles, and ultrasound of the device of the present invention is expected, as is an extension of the window in which stroke therapy can be commenced from the current guideline of less than or equal to 3 hrs from onset, most often enough time to reach a facility suitably equipped for stroke patients. Other improvements in drug delivery are conceived.

FIG. 30 depicts examples of alternate therapeutic interventions to block or reverse thrombosis that are accelerated or enabled by ultrasound. Shown are inhibitors of Factor X and Factor IX, where the use of the device of the present invention is conceived to promote more rapid interaction of the inhibitors with their targets. These drugs are in clinical development, but have been found to result in minimal ICH as a side effect. Also anticipated is the use of the device of the present invention with next generation tPAs, such as a recombinant pro-urokinase (a product of Thrombolytic Sciences Intl) that is modified to reduce ICH and "monteplase" (a product of Eisai Pharmaceuticals), for example.

Exogenous drugs expected to benefit from the safe transcranial ultrasound device of the invention include exogenous plasminogen activators, plasminogen activator prodrugs, Alteplase, Reteplase, Tenecteplase, desmoteplase, monteplase, urokinase, pro-urokinase, mutant pro-urokinase, streptokinase, single-chain urokinase-type PA, recombinant streptokinase, microplasmin, V10153, DB-B99, staphylokinase, Factor IX inhibitors, Factor X inhibitors, GP IIb-IIIa antagonists, anticoagulants, prostaglandin synthase inhibitors, nitroglycerin or related NO precursors, microbubble suspensions or precursor, and the like, including standby therapies such as heparin, warfarin, coumadin, Rivaroxaban, Apixaban, Dabigatran, and aspirin, which may be used prophylactically or for the treatment of stroke.

Also of interest are pharmacological treatments for mitochondrial hypoxia and ischemia as useful to reduce morbidity following stroke. These include those cited in U.S. Pat. No. 7,807,654 and reviewed by Wallace recently (2010, Mitochondrial Energetics and Therapeutics, Ann Rev Path 5:297-348).

FIGS. 31A and 31B depict a model for vascular vasodilation with release of endogenous nitric oxide, where blood shear (FIG. 31A) is replaced by ultrasound (FIG. 31B). This model predicts that the ultrasound device of the present invention will have a positive effect as a standalone device for non-invasive treatment of a variety of conditions, including migraine, headache, intracranial hypertension, hydrocephalus, and so forth, and may increase blood flow to the brain so as to improve delivery of a variety of parenteral and oral drug formulations. An apparatus with headset of the invention has been demonstrated for use in relief of migraine.

While the above is a complete description of selected embodiments of the present invention, it is possible to practice the invention use various alternatives, modifications, combinations and equivalents. All of the U.S. patents, U.S. patent application publications, U.S. patent applications, foreign patents, foreign patent applications and non-patent publications referred to in this specification are incorporated herein by reference in their entirety. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

INDUSTRIAL APPLICABILITY

The transcranial ultrasonic device of this invention may be used for dissolving thrombi responsible for cerebral infarction by irradiating the affected tissue with repeating cycle of ultrasonic wave patterns, and finds other uses in therapy of neurological and vascular conditions.

In one embodiment, a transcranial ultrasound apparatus is configured for adjusting $V_{BANG}$ using data on transducer voltage response. Using a multiplexed driving signal or signals, ultrasound is emitted by a plurality of transducers of an array while varying voltage to each individual transducer on the fly, thus improving reproducibility and consistency of insonation, which can be irregular due to variations in transducer manufacture.

In a study in generally healthy volunteers, no safety issues were discovered, suggesting that the device may be used, in the absence of a clinical indication, for subclinical conditions not requiring medical or surgical intervention and for prophylaxis of a variety of conditions such as headache and migraine, where an attending physician is not required. By virtue of its self-contained, standalone design, it is portable and may be used by emergency medical personnel prior to a definitive diagnosis by a physician. It is not a surgical device and may be used absent any invasive therapy.

EXAMPLE I

A clinical study was conducted. In an NIH-sponsored safety trial, fifteen healthy volunteers were fitted with an apparatus of the invention. Modulated ultrasonic insonation was initiated according to the invention and continued for two hours while monitoring vascular and neurological status. No adverse effects were reported in any of the test subjects.

EXAMPLE II

In a second NIH-sponsored study, efficacy was addressed. The method and apparatus of the invention was used to treat ischemic stroke patients in a single-arm, nonrandomized study with r-tPA as cotherapy. Thirteen subjects have been enrolled to date. Based on the interim results obtained thus far, 3 of 13, or 23% of subjects have achieved complete recanalization at 2 hours. This represents a 4% increase over the rate of complete recanalization at 2 hours in subjects treated with tPA alone in a parallel study conducted without ultrasound, i.e., using r-tPA alone. At this time, 90-day functional outcome data is available for 9 of the 13 subjects. Of the 9 subjects in which 90-day mRS scores are currently available, 3 or 33% have achieved scores of 0-1. These data include patients with severe deficit on initial evaluation (baseline NIHSS score>20). The recanalization rates demonstrate that the headset of the invention is more effective than r-tPA alone in restoring blood flow to occluded arteries.

EXAMPLE III

In one aspect of the invention, a headset is realized that permits users to target critical vasculature without special imaging studies: i.e., simply by fitting the headset onto the skull according to craniological landmarks that define a reference plane and the location of the major arteries. Studies were undertaken to determine what level of targeting was achieved. Transducer arrays of the headsets of the invention were modified to permit transcranial Doppler monitoring, where the "on-target" aim of the therapeutic insonation was scored by detection of Doppler signals from the target vasculature. In a preliminary study, a review of case reports revealed that 86% of patients had detectable Doppler waveforms in the MCA and related cerebral vasculature. An average of 4.1 transducers received a return signal, indicating that multiple transducers were on target. In a second study, MCA-localized Doppler was detected in 100% of all subjects; on average, 5.8 of the 12 temporally disposed transducers received Doppler return signals from the targeted MCA region and 2.7 of 4 transducers in the suboccipital array received Doppler return signals from the targeted Basilar Artery. Combining the studies, 91% of the subjects showed evidence that the headset transducer arrays were correctly targeting the cerebral vasculature nexus most closely associated with thromboembolic stroke. The device is thus demonstrated to be more effective than r-tPA alone for treatment of underlying ischemic stroke associated with the MCA and associated arteries. The function of the headset to achieve rapid, unassisted, "passive" stereotactic targeting of the ultrasonic transducers onto key vascular targets is a factor in this success.

While representative, the data of these examples is not intended to limit the invention to a particular wavelength, modulated insonation pattern, intensity, or one particular transducer array geometry. One skilled in the art will discover that certain insonation patterns or frequencies are more effective than others and that modifying the geometry or number of transducers in the arrays will achieve incremental improvements. Also, while clinical studies have not been approved for testing of the headset as a stand-alone therapy in ischemic disease, studies will show that incremental improvements in 90 day outcomes are obtained by periodic follow-up treatment with ultrasound (without r-tPA) over a period of several days or weeks following an ischemic attack, and in fact the headset can be use prophylactically if needed absent co-administered enzyme because of its demonstrated capacity to actuate endogenous mediators of thrombolysis.

INCORPORATION BY REFERENCE

All of the U.S. patents, U.S. patent application publications, U.S. patent applications, foreign patents, foreign patent applications and non-patent publications referred to in this specification and related filings are incorporated herein by reference in their entirety.

While the above is a complete description of selected embodiments of the present invention, it is possible to practice the invention use various alternatives, modifications, combinations and equivalents. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. An apparatus for non-invasive therapeutic application of transcranial ultrasound, which comprises:
    a) an adjustably tightenable circumcranial headset assembly configured with registration surfaces for engaging at least three external craniological landmarks of a skull so as to stereotactically position a headset assembly on said skull with respect to an intracranial target or targets;
    said headset assembly including anterior and posterior headframe members configured to mate at corresponding ends of said members such as to define, when the headset assembly is positioned on the subject's head for transcranial sonothrombolysis, a headset plane that is inclined with respect to a horizontal reference plane and is parallel to a plane of a subject's Circle of Willis, so that said headset is raised above the eyes of said skull, has clearance around the ears of said skull, and engages an underside of a occipital protuberance of said skull when stereotactically positioned thereon, said headset assembly including
  a nasion mounting registration bracket having a fixed end affixed to the headset assembly anteriorly at a midpoint at the front and a second end and protruding transversely to the headset plane and along the subject's forehead such as to offset said midpoint of the headset by a height $h_1$ with respect to the nasion, and
  a left (Lt) transducer-array registration bracket and a right (Rt) array-registration bracket slidably disposed contralaterally and removably on an internal surface of said headset assembly;

b) a plurality of transducer arrays, each said transducer array comprising a plurality of non-focused ultrasound transducers, wherein said transducers are mounted on said headset so as to be stereotactically directed at said target or targets without need for diagnostic imaging guidance;

said transducer arrays including
  left (Lt) and right (Rt) temporal transducer arrays aligned, respectively, by the Lt and Rt transducer-array registration brackets with an otobasion superior and a sphenoid shelf on the opposite sides of the subject's head such as to optimize a degree of insonation of a target central cerebral vasculature with an ultrasound (US) beam emitted by said first transducer array, the insonation being directed substantially along the headset plane, and
  a posterior occipital transducer array disposed at a back portion of the headset such as to direct corresponding US beams at the basilar and vertebral artery and a junction of an internal carotids of the Circle of Willis, and c) operatively attached to said headset, an electronic circuit with microcontroller, clock, memory, instruction set, a portable power and voltage supply, and on/off control for actuating said plurality of transducers in a repeating cycle, each cycle a metapulse comprising a plurality of trains of pulses, each train of pulses emitted intermittently and alternately at low duty cycle from selected transducers in a programmed sequence, whereby said skull is insonated with a stereotemporally modulated pattern of ultrasound without operator intervention and with low power consumption, the low duty cycle eliminating the need for assisted cooling.

2. The apparatus of claim 1, wherein said at least three external craniological landmarks are nasion, Rt otobasion superius, and Lt otobasion superius, said craniological landmarks forming an Isosceles triangle which defines a foundational reference plane containing the sphenoid shelf and the Circle of Willis of said skull, said triangle having a base, an apex, and a midline, said triangle for stereotactically positioning said headset and for stereotactically aligning said non-focused ultrasound transducers to insonate the vasculature of said Circle of Willis, the branches and junctions of the internal carotid and basilar arteries conjoined thereto, and the cerebral arteries projecting therefrom, thereby directing said insonation to said vasculature without need for diagnostic imaging guidance; and further wherein said plurality of transducer arrays comprise arrays selected from i) a right temporal transducer array and a left temporal transducer array or ii) a right temporal transducer array, a left temporal array, and an occipital transducer array, and wherein each transducer of said plurality of transducer arrays is independently operable.

3. The apparatus of claim 2, wherein said headset assembly comprises:
  a) an anterior headframe member configured for spanning ear to ear across the brow of said skull; said anterior headframe member generally "U-shaped" in form, with first end and second end contralaterally disposed thereon;
  b) a posterior headband member configured for spanning ear to ear under the occipital protuberance of said skull, said posterior headband having two ends, wherein each said end is configured for inserted into one apposing end of said anterior headframe member, said anterior headframe member further comprising a tensioning mechanism for engaging said ends of said posterior headband member and tightening said headset circumcranially around said skull;
  wherein the left an right transducer-array registration brackets each has a registration surface configured for engaging one each said Rt otobasion superius craniological landmark and said Lt otobasion superius craniological landmark.

4. The apparatus of claim 3, wherein each said registration surface of the left and right transducer-array registration brackets is an earpiece, and said Rt earpiece is fixedly mounted in relation to said Rt temporal transducer array and said Lt earpiece is fixedly mounted in relation to said Lt temporal transducer array, said earpieces each having dimensions for stereotactically positioning said each temporal transducer array in acoustic contact with a temporal acoustic window when said nasion registration pad is seated on said nasion and said each earpiece is seated on one said otobasion superius.

5. The apparatus of claim 4, wherein said occipital transducer is seated proximate to an occipital acoustic window when said posterior headband is circumcranially tightened around said skull.

6. The apparatus of claim 1, wherein said circuit with portable power and voltage supply are operatively attached to said headset by a detachable electromagnetically shielded umbilicus.

7. The apparatus of claim 1, wherein said circuit with microcontroller and memory comprise digitally encoded instructions in non-volatile memory for autonomously driving at least one therapeutic or prophylactic ultrasonic treatment regimen until a stop instruction is executed; said ultrasonic treatment regimen comprising metapulses of stereotemporally modulated ultrasound having:
  a) a metapulse cycle repetition frequency of 0.25 to 20 Hz, wherein each metapulse comprises a plurality of pulse trains emitted intermittently and asynchronously from said plurality of transducers;
  b) wherein each pulse train comprises 2 to 300 pulses of ultrasound per train at a pulse repetition frequency of 4 kHz to 10 kHz;
  c) wherein each pulse comprises ultrasound at a primary frequency $f_c$ and has a pulse duration of 0.2 to 10 microseconds; and,
  d) further wherein each transducer of said plurality of arrays has a duty cycle of 0.1 to 10% per metapulse, thereby achieving low power consumption and passive cooling for extended autonomous portable operation.

8. The apparatus of claim 7, wherein said ultrasound pulses are emitted at a primary frequency $f_c$ selected from a group of frequency ranges consisting of frequencies a) from about 0.8 MHz to about 2.2 MHz; b) from about 0.5 MHz to about 3.5 MHz; c) from about 1 to about 2 MHz; d) about 1 MHz; e) about 2 MHz; f) about 1.2 MHz, and g) about 0.8 MHz.

9. The apparatus of claim 7, wherein each said pulse at said frequency $f_c$ is driven by a voltage (V.sub.p-p) configured such that a maximum attenuated peak rarefaction pressure $P_{rA}$ delivered at depth $z_{sp}$ in a head does not exceed 300 KPa and does not exceed pressure corresponding to a physiologically compatible thermal index.

10. The apparatus of claim 9, wherein said therapeutic or prophylactic insonation regimen is configured for self-administration at the press of a button.

11. The apparatus of claim 9, where said therapeutic or prophylactic insonation regimen is configured for: a) non-invasively dispersing or generating an endogenous mediator of a physiological state; b) non-invasively accelerating activity of a drug having an effect on a neurological or vascular condition; c) non-invasively controlling or preventing ischemic stroke of a cerebral vasculature; d) non-invasively controlling or preventing atheroma or microatheroma of a cerebral vasculature; e) non-invasively controlling or preventing headache, migraine, or hydrocephaly; f) non-invasively applying transcranial ultrasound following administration of a recombinant tPA or other plasminogen activator in treatment of ischemic stroke; g) non-invasively applying transcranial ultrasound outside a 3 hour window post onset of stroke, said 3 hour window being a generally recognized window for efficacious administration of r-tPA; h) non-invasively applying transcranial ultrasound for treatment or control of stroke without co-therapy; i) non-invasively applying transcranial ultrasound for treatment or control of stroke in combination with administration of a microbubble suspension or microbubble suspension precursor; j) non-invasively applying transcranial ultrasound for treatment of cerebrovascular ischemia, where said ischemia is caused by ischemic stroke or by hemorrhagic stroke; and/or, k) non-invasively applying transcranial ultrasound following administration of an exogenous plasminogen activator, a plasminogen activator prodrug, a urokinase, a pro-urokinase, a mutant pro-urokinase a streptokinase, a staphylokinase, an anisolated plasminogen-streptokinase activator complex (APSAC), a single-chain urokinase-type PA, a monteplase, an Alteplase, a Reteplase, a Tenecteplase, and a desmoteplase, a Factor IX inhibitor, a Factor X inhibitor, an anticoagulant, a prostaglandin synthase inhibitor, a GP IIb-IIIa antagonist, a nitrone, an Edaravone, a heparin, a warfarin, a coumadin, a nitroglycerin or related NO precursors, a microbubble suspension or precursor, and the like; l. non-invasively applying transcranial ultrasound before obtaining a diagnosis of ischemic versus hemorrhagic stroke; m. non-invasive application of transcranial ultrasound by a first responder, an emergency technician, or a patient prior to a confirmation of a diagnosis of stroke by imaging means.

12. The apparatus of claim 1, wherein said portable power and voltage supply is battery pack, said battery pack having weight of less than 250 grams, and said battery pack includes at least one of a rechargeable battery, an insertable battery, a lithium ion battery, a lithium ion polymer battery, a lithium iron phosphate battery, a lithium-sulfur battery, a lithium-titanate battery, a nickel-zinc battery, a nickel-iron battery, a NiCd battery, a NiMH battery, an alkaline battery, a 9 V battery, a cell phone battery, or at least one AA or AAA battery, and a portable power source.

13. The apparatus of claim 1, said headset assembly and operating circuit having a power consumption of less than about 400 mAmp-hr, more preferably less than about 300 mAmp-hr, and thereby having an operating life on battery power without recharging of more than 2 hours but not limited to up to about 12 hours at an operating voltage of about 3 to about 9 VDC, more preferably about 3.5.+−0.1 VDC, thereby permitting transport, ambulation, or carrying without interruption of a programmable continuous or intermittent therapeutic or prophylactic insonation regimen.

14. The apparatus of claim 1, wherein said headset assembly weighs less than 500 grams, or wherein said apparatus with headset, microcontroller and power supply weighs less than 1 kilogram.

15. The apparatus of claim 1, wherein said apparatus is configured an autonomon for operator-independent use, said operator interface comprising only an on-off/pause control surface and at least one status indicator selected from green LED, red LED, LCD display, touch screen, buzzer, vibrator, or speaker.

16. The apparatus claim 1, further comprising a subcircuit selected from: a) a watchdog subcircuit for safe operation; b) an acoustic coupling subcircuit for verifying acoustic coupling; c) a voltage regulation subcircuit with digital resistor feedback means and non-volatile data storage means for adjusting transducer boost voltage according to calibration data stored therein, thereby compensating for transducer-to-transducer variability; and d) a fuel gauge subcircuit for optimizing battery life.

17. The apparatus of claim 1, wherein a peak amplitude $P_{r0}$ of said pulse or train of pulses emitted from said each ultrasonic transducer is adjusted in amplitude on the fly to reduce intertransducer manufacturing variability, thereby improving insonation consistency.

18. An apparatus for transcranial sonothrombolysis of a targeted cerebral vasculature of a subject's head, the apparatus comprising:
  a set of transducer arrays; and
  a headset supporting said set of transducer arrays and mountable on the subject's head, said headset including anterior and posterior headframe members configured to mate at corresponding ends of said members such as to define, when the headset is positioned on the subject's head for transcranial sonothrombolysis, (i) a headset plane that is inclined with respect to a horizontal reference plane and is parallel to a plane of the subject's Circle of Willis, and (ii) a circumcranial loop of said headset, wherein mutual positioning of the anterior and posterior headframe members is tensionally adjustable,
  said headset and including one or more mounting registration brackets adapted
    to stereotactically cooperate with the subject's head such as to align transducer arrays from said set of transducer arrays with corresponding transcranial acoustic windows of the subject's head when the headset is positioned on the subject's head for transcranial sonothrombolysis, and
    to optimize an insonation of a targeted cerebral vasculature through said transcranial acoustic windows with ultrasound (US) beams emitted by said transducer arrays in such stereotactically cooperated position,
  wherein a nasion mounting registration bracket, from one or more mounting registration brackets, has a fixed end affixed to the headset at the front and a second end and protrudes transversely to the headset plane and along the subject's forehead, wherein a first transducer-array registration bracket and a second array-registration bracket align, respectively, first and second temporal transducer arrays, from the set of transducer arrays, with an otobasion superior and a sphenoid shelf on the opposite sides of the subject's head such as to optimize a degree of insonation of a target central cerebral vasculature with an ultrasound (US) beam emitted by said first transducer array, the insonation being directed substantially along the headset plane, wherein a posterior occipital transducer array, from the set of transducer arrays, is disposed at a back portion of the headset such as to direct corresponding US beams at the basiliar and vertebral artery and a junction of an internal carotids of the Circle of Willis, and wherein said nasion and first transducer-array registration brackets are configured such that, when the headset is positioned on the subject's head for transcranial sonothrombolysis, said first transducer-array registration bracket aligns said first temporal transducer array with an otobasion superior and a sphenoid shelf without a need for measuring or locating of said otobasion superior and sphenoid shelf prior to positioning of the headset on the subject's head.

19. An apparatus according to claim 18, wherein said chosen external craniological marks include a left otobasion superior (OBS), a right OBS, and a nasion of the subject's head.

20. An apparatus according to claim 19, wherein said temporal transducer array registration bracket is slidably and removably mounted on an internal surface of said headset.

21. An apparatus according to claim 18, wherein the headset plane passes through said left and right OBS when the headset is positioned on the subject's head for transcranial sonothrombolysis.

22. An apparatus according to claim 18, wherein said one or more mounting registration brackets includes a registration bracket configured to contact one of a nasion, left otobasion superior (OBS), right OBS, tragion, mandibular condyle, zygomatic arch, prosthion, and occipital prominence when the headset is positioned on the subject's head for transcranial sonothrombolysis.

23. An apparatus according to claim 18, wherein said headset includes anterior and posterior headframe members configured to mate at corresponding ends of said members such as to define a circumcranial loop of said headset.

24. An apparatus according to claim 23, wherein mutual positioning of the anterior and posterior headframe members is tensionably adjustable.

25. A headset apparatus for providing transcranial sonothrombolysis of a target cerebral vasculature of a subject's head, comprising
(i) a processor;
(ii) a non-transitory tangible computer-readable medium;
(iii) computer-readable program code encoded in said computer-readable medium;
(iv) an ultrasound (US) device that has a headset plane and includes mounting registration brackets, defined with respect to corresponding external craniological marks of the subject's head, and a set of transducer arrays, said ultrasound device being positionable onto the subject's head such that the mounting registration brackets are brought into contact with respectively corresponding external craniological marks and the headset plane is placed at an angle with respect to a horizontal reference plane that is defined by said external craniological marks and parallel to a plane of the subject's Circle of Willis,
wherein
a nasion mounting registration bracket has a fixed end affixed to the headset at the front and a second end and protrudes transversely to the headset plane and along the subject's forehead,
a first transducer-array registration bracket and a second array-registration bracket align, respectively, first and second temporal transducer arrays, from the set of transducer arrays, with an otobasion superior and a sphenoid shelf on the opposite sides of the subject's head such as to optimize a degree of insonation of a target central cerebral vasculature with an ultrasound (US) beam emitted by said first transducer array, the insonation being directed substantially along the headset plane,
and
a posterior occipital transducer array, from the set of transducer arrays, is disposed at a back portion of the headset such as to direct corresponding US beams at the basiliar and vertebral artery and a junction of an internal carotids of the Circle of Willis,
wherein said nasion and first transducer-array registration brackets are configured such that, when the headset is positioned on the subject's head for transcranial sonothrombolysis, said first transducer-array registration bracket aligns said first temporal transducer array with the otobasion superior and the sphenoid shelf without a need for measuring or locating of said otobasion superior and sphenoid shelf prior to positioning of the headset on the subject's head;
wherein the computer readable program code comprises a series of computer readable program steps to effect:
insonating, in the headset plane, the target cerebral vasculature; and
defining a regime of operation of the at least one of said transducer arrays.

26. An apparatus according to claim 25, wherein said insonating includes insonating with at least one of a temporal transducer array and an occipital transducer array.

27. An apparatus according to claim 25, wherein said defining includes defining at least one of temporal and amplitude sequence of pulses of US beams.

* * * * *